(12) United States Patent
Sigurdsson et al.

(10) Patent No.: US 9,777,056 B2
(45) Date of Patent: Oct. 3, 2017

(54) IMMUNOTHERAPY FOR CLEARING PATHOLOGICAL TAU CONFORMERS

(71) Applicant: New York University, New York, NY (US)

(72) Inventors: Einar M. Sigurdsson, Scarsdale, NY (US); Ayodeji Asuni, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 14/833,679

(22) Filed: Aug. 24, 2015

(65) Prior Publication Data

US 2015/0368328 A1   Dec. 24, 2015

Related U.S. Application Data

(62) Division of application No. 13/225,148, filed on Sep. 2, 2011, now Pat. No. 9,139,643, which is a division of application No. 11/693,375, filed on Mar. 29, 2007, now Pat. No. 8,012,936.

(60) Provisional application No. 60/787,051, filed on Mar. 29, 2006.

(51) Int. Cl.
| | |
|---|---|
| *C07K 16/18* | (2006.01) |
| *A61K 39/00* | (2006.01) |
| *A61K 38/00* | (2006.01) |
| *A61K 9/00* | (2006.01) |
| *C07K 14/47* | (2006.01) |
| *A61K 39/395* | (2006.01) |

(52) U.S. Cl.
CPC ............ *C07K 16/18* (2013.01); *A61K 9/0019* (2013.01); *A61K 39/3955* (2013.01); *C07K 14/4711* (2013.01); *A61K 38/00* (2013.01); *A61K 2039/505* (2013.01); *A61K 2039/507* (2013.01)

(58) Field of Classification Search
None
See application file for complete search history.

(56) References Cited

U.S. PATENT DOCUMENTS

| | | | |
|---|---|---|---|
| 5,492,812 A | 2/1996 | Vooheis | |
| 6,238,892 B1 | 5/2001 | Mercken et al. | |
| 7,446,180 B2 | 11/2008 | Novak | |
| 2002/0197258 A1* | 12/2002 | Ghanbari | C07K 16/18 424/146.1 |
| 2005/0037013 A1* | 2/2005 | Schenk | A61K 38/1709 424/185.1 |
| 2008/0050383 A1 | 2/2008 | Sigurdsson et al. | |

FOREIGN PATENT DOCUMENTS

| | | |
|---|---|---|
| WO | WO 93/11231 | 6/1993 |
| WO | WO 98/22120 | 5/1998 |
| WO | WO 02/064084 | 8/2002 |
| WO | WO 03/045128 | 6/2003 |

OTHER PUBLICATIONS

Paul 2013 "Chapter 7: antigen-antibody interactions and monoclonal antibodies" Fundamental Immunology 7th ed p. 199.*
Asuni, A.A. et al. (2006) "*Tau-Based Immunotherapy for Dementia*," Program and Abstracts of the 10th Int'l Conference on Alzheimer's Disease and Related Disorders, Madrid, Spain. Abstract O2-05-04.
Bibl, M. et al. (2012) "*Neurochemical Biomarkers in Alzheimer's Disease and Related Disorders*," Ther. Adv. Neorolog. Disorders 5(6):335-348.
Bramblett, G.T. et al. (1993) "*Abnormal Tau Phosphorylation at Ser$^{396}$ in Alzheimer's Disease Recapitulates Development and Contributes to Reduced Microtubule Binding*," Neuron 10:1089-1099.
Daly, N.L. et al. (2000)"*Role of Phosphorylation in the Confirmation of τ Peptides Implicated in Alzheimer's Disease*," Biochemistry 39:9039-9046.
Eurasian Patent Search Report Application No. 201171397 (2012) (4 pages).
Fagen, A.M. et al. (2012) "*Upcoming Candidate Cerebrospinal Fluid Biomarkers of Alzheimer's Disease*," Biomarkers Med. 6(4):455-476.
Frieden, C. et al. (2013) "*Concerning the Structure of apoE*," Protein Science 22:1820-1825.
Goedert, M. et al. (1994) "*Epitope Mapping of Monoclonal Antibodies to the Paired Helical Filaments of Alzheimer's Disease: Identification of Phosphorylation Sites in Tau Protein*," Biochem. J. 301:871-877.
Gu, J. and Sigurdsson, E. (2011) "*Immunotherapy for Tauopathy*," J. Molec. Neurosci. 45(3):690-695.
Gustaw-Rothenberg, K. et al. (2010) "*Biomarkers in Alzheimer's Disease: Past, Present and Future*," Biomark Med. 4(1):15-26.
Himmelstein, D.S. et al. (2012) "*Tau as a Therapeutic Target in Neurodegenerative Disease*," Pharmacol. Therap. 136:8-22.
Hoffmann, R. et al. (1997)"*Unique Alzheimer's Disease Paired Helical Filament Specific Epitopes Involve Double Phosphorylation at Specific Sites*," Biochemistry 36(26):8114-8124.
Ishiguro, K. et al. (1992) "*Prosphorylation Sites on Tau by Tau Protein Kinase I, a Bovine Derived Kinase Generating an Epitope of Paired Helical Filaments*," Neuroscience Lett. 148:202-206.
Jicha, G.A. et al. (1997) "*A Conformation- and Phosphorylation-Dependent Antibody Recognizing the Paired Helical Filaments of Alzheimer's Disease*," J. Neurochem. 69:2087-2095.
Jicha, G.A. et al. (1999) "*Sequence Requirements for Formation of Conformational Variants of Tau Similar to Those Found in Alzheimer's Disease*," J. Neurosci. Res. 55(6):713-723.
Johnson, G.V. et al. (2004) "*Tau Phosphorylation in Neuronal Cell Function and Dysfunction*," J. Cell Sci. 117(24):5721-5729.

(Continued)

*Primary Examiner* — Adam D Weidner
(74) *Attorney, Agent, or Firm* — AuerbachSchrot LLC; Jeffrey I. Auerbach

(57) ABSTRACT

The present invention relates to methods of treating and preventing Alzheimer's Disease or other tauopathies in a subject by administering a tau protein, its immunogenic epitopes, or antibodies recognizing the tau protein or its immunogenic epitopes under conditions effective to treat or prevent Alzheimer's Disease of other tauopathies. Also disclosed are methods of promoting clearance of from the brain of the subject and of slowing progression of tangle-related behavioral phenotype in a subject.

15 Claims, 15 Drawing Sheets

(56) References Cited

OTHER PUBLICATIONS

Kenessey, A. et al. (1993) "*The Extent of Phosphorylation of Fetal tau is Comparable to That of PHF-Tau from Alzheimer Paired Helical Filaments,*" Brain Research 629:40-46.

Knopman, D.S. et al. (2001) "*Practice Parameter: Diagnosis of Dementia (an Evidence-Based Review) Report of the Quality Standard Subcommitte of the American Academy of Neurology,*" Neurology 56:1143-1153.

Lang, E. et al. (1992) "*Immunological and Conformational Characterization of a Phosphorylated Immunodominant Epitope on the Paired Helical Filaments Found in Alzheimer's Disease,*" Biochem. Biophys. Res. Commun. 187(2):783-790.

Maupetit, J. et al. (2009) "*PEP-FOLD: An Online Resounrce for De Novo Peptide Structure Prediction,*" Nucleic Acids Res. 37(Web Server Issue):W498-W503.

Maupetit, J. et al. (2010) "*A Fast and Accurate Method for Large-Scale De Novo Peptide Structure Prediction,*" J. Comput. Chem. 31:726-738.

Novak, M. (1994) "*Truncated Tau Protein as a New Marker for Alzheimer's Disease,*" Acta Virol. 38:173-189.

Novak, M. et al. (1993) "*Molecular Characterization of the Minimal Protease Resistant Tau Unit of the Alzheimer's Disease Paired Helical Filament,*" EMBO J. 12(1):365-370.

Otvos, L. et al. (1994) "*Monoclonal Antibody PHF4 Recognized Tau Protein Phosphorylated at Serine Residues 396 and 404,*" J. Neurosci. Res. 39:669-673.

Park, S.Y. et al. (2005) "*The Generation of a 17 kDa Neurotoxic Fragment: An Alternative Mechanism by Which Tau Mediates Beta-Amyloid-Induced Neurodegneration,*" J. Neurosci. 25(22):5365-5375.

Percy, M. et al. (2014) "*Risk Factors for Development of Dementia in a Unique Six-Yeawr Cohort Study. I. An Exploratory, Pilot Study of Involvement of the E4 Allele of Apolipoprotein E, Mutations of the Hemochromatosis-HFE Gene, Type 2 Diabetes, and Stroke,*" J. Alzheimer's Disease 38(4):907-922.

Porzig, R. et al. (2007) "*Epitope Mapping of Mabs AT8 and Tau5 Directed Against Hyperphosphorylated Regions of the Human Tau Protein,*" Biochem. Biophys. Res. Commun. 358:644-649.

Ringman, J.M. et al. (2013) "*New Genes and New Insights from Old Genes: Update on Alzheime Disease,*" Coninuum 19(2):358-371.

Rosenmann, H. et al. (2006) "*Tauopathy-Like Abnormalities and Neurologic Deficits in Mice Immunized with Neuronal Tau Protein,*" Arch. Neurol. 63:1459-1467.

Schenk, D et al. (1999) "*Immunization with Amyloid-Beta Attenuates Alzheimer-Disease-Like Pathology in the PDAPP Mouse,*" Nat. 400:173-177.

Singer, D. et al. (2006) "*Neighbored Phosphorylation Sites as PHF-Tau Specific Markers in Alzheimer's Disease,*" Biochem. Biophys. Res. Commun. 346:819-828.

Skrabana, R. et al. (2004) "*Folding of Alzheimer's Core PHF Subunit Revealed by Monoclonal Antibody 423,*" FEBS Left. 568:178-182.

Taniguchi, T et al. (2005) "*Effects of Different Anti-Tau Antibodies on Tau Fibrillogenesis: RTA-1 and RTA-2 Counteract Tau Aggregation,*" FEBS Left. 579(6):1399-1404.

Thévenet, P. et al. (2012) "*PEP-FOLD: An Updated De Novo Structure Prediction Server for Both Linear and Disulfide Bonded Cyclic Peptides,*" Nucleic Acids Res. 40:W288-W293.

Vickers, J.C. (2002) "*A Vaccine Against Alzheimer's Disease,*" Drugs & Aging 19(7):487-494.

Yanamandra, K. et al. (2013) "*Anti-Tau Antibodies That Block Tau Aggregate Seeding In Vitro Markedly Decrease Pathology and Improve Cognition In Vivo,*" Neuron 80(2):402-414.

Anderson, D.C. et al. (1990) "*Use of Flanking Sequences to Study Secondary, Structure Activity Correlations of a Mycobacterium leprae T Cell Epitope,*" Eur. J. Immunol. 20:2691-2697.

Anfinsen, C.B. (1973) "*Principles That Govern the Folding of Protein Chains,*" Science 181(4096):223-230.

Bergmann C.C. et al. (1994) "*Differential Effects of Flanking Residues on Presentation of Epitopes from Chimeric Peptides,*" J. Virol. 68(8):5306-5310.

Bergmann C.C. et al. (1996) "*Flanking Residues Alter Antigenicity and Immunogenicity of Multi-Unit CTL Epitopes,*" J. Immunol. 157:3242-3249.

Billingsley, M.L. et al. (1997) "*Regulated Phosphorylation and Dephosphorylation of Tau Protein: Effects on Microtubule Interaction, Intracellular Trafficking and Neurodegeneration,*" Biochem. J. 323:577-591.

Briggs, S. et al. (1993) "*Fine Specificity of Antibody Recognition of Carcinoma-Associated Epithelial Mucins: Antibody Binding to Synthetic Peptide Epitopes,*" Eur. J. Cancer 29A(2):230-237.

Craig, L. et al. (1998) "*The Role of Structure in Antibody Cross-reactivity Between Peptides and Folded Proteins,*" J. Mol. Biol. 281:183-201.

Dyson, H.J. (1988) "*Folding of Immunogenic Peptide Fragments of Proteins in Water Solution; I. Sequence Requirements for the Formation of a Reverse Turn,*" J. Mol. Biol. 201:161-200.

Fieser, T.M. et al. (1987) "*Influence of Protein Flexibility and Peptide Conformation on Reactivity of Monoclonal Anti-Peptide Antibodies With a Protein α-Helix,*" Proc. Natl. Acad. Sci. (U.S.A.) 84:8568-8572.

Furie, B. et al. (1974) "*Antibodies to the Unfolded Form of a Helix-Rich Region in Staphylococcal Nuclease,*" Biochemistry 13(8):1561-1566.

Ghillani, P. et al. (1988) "*Monoclonal Antipeptide Antibodies as Tools to Dissect Closely Related Gene Products. A Model Using Peptides Encoded by the Calcitonin Gene,*" J. Immunol. 141:3156-3163.

Gokhale, A.S. et al. (2014) "*Peptides and Peptidomimetics as Immunomodulators,*" Immunotherapy 6(6):755-774.

Heemskerk, M. H. M. et al. (1995) "*Differential Activation of Mouse Hepatitis Virus-Specific CD4+ Cytotoxic T Cells Is Defined by Peptide Length,*" Immunology 85:517-522.

Hunt, J.C. et al. (1990) "*Mouse Monoclonal Antibody 5-21-3 Recognizes a Contiguous, Conformation-Dependent Epitope and Maps to a Hydrophilic Region in HIV-1 gp41,*" Aids Res. Hum. Retrovir. 6(5):587-598.

Jackson, D.C. et al. (2000) "*Preparation and Properties of Totally Synthetic Immunogens,*" Vaccine 18:355-361.

Nyberg, L. (2014) "Alzheimer's Research: 3 Reasons for Hope," http://journalstar.com/niche/neighborhood-extra/senior-scene/alzheimer-s-research-reasons-for-hope/article_a1fcc704-c3ab-5a70-aa8d-ea7bcaa481c6.html [redacted to remove advertisements]; 2 pages.

Raman, C.S. et al. (2000) "*Antibody-Detected Folding: Kinetics of Surface Epitope Formation Are Distinct From Other Folding Phases,*" Polymer Sci. 9:129-137.

Sachs, D.H. et al. (1972) "*Antibodies to a Distinct Antigenic Determinant of Staphyloccocus Nuclease,*" J. Immunol. 109(6):1300-1310.

Sachs, D.H. et al. (1972) "*An Immunologic Approach to the Conformational Equilibria of Polypeptides,*" Proc. Natl. Acad. Sci. (U.S.A.) 69:3790-3794.

Steers, N.J. et al. (2014) "*Designing the Epitope Flanking Regions for Optimal Generation of CTL Epitopes,*" Vaccine 32:3509-3516.

Vignali, D.A.A. et al. (1994) "*Amino Acid Residues that Flank Core Peptide Epitopes and the Extracellular Domains of CD4 Modulate Differential Signaling through the T Cell Receptor,*" J. Exp. Med. 179:1945-1956.

Zichel, R et al. (2012) "Aptamers as a Sensitive Tool to Detect Subtle Modifications in Therapeutic Proteins," PLoS One 7(2):e31948; pp. 1-11.

* cited by examiner

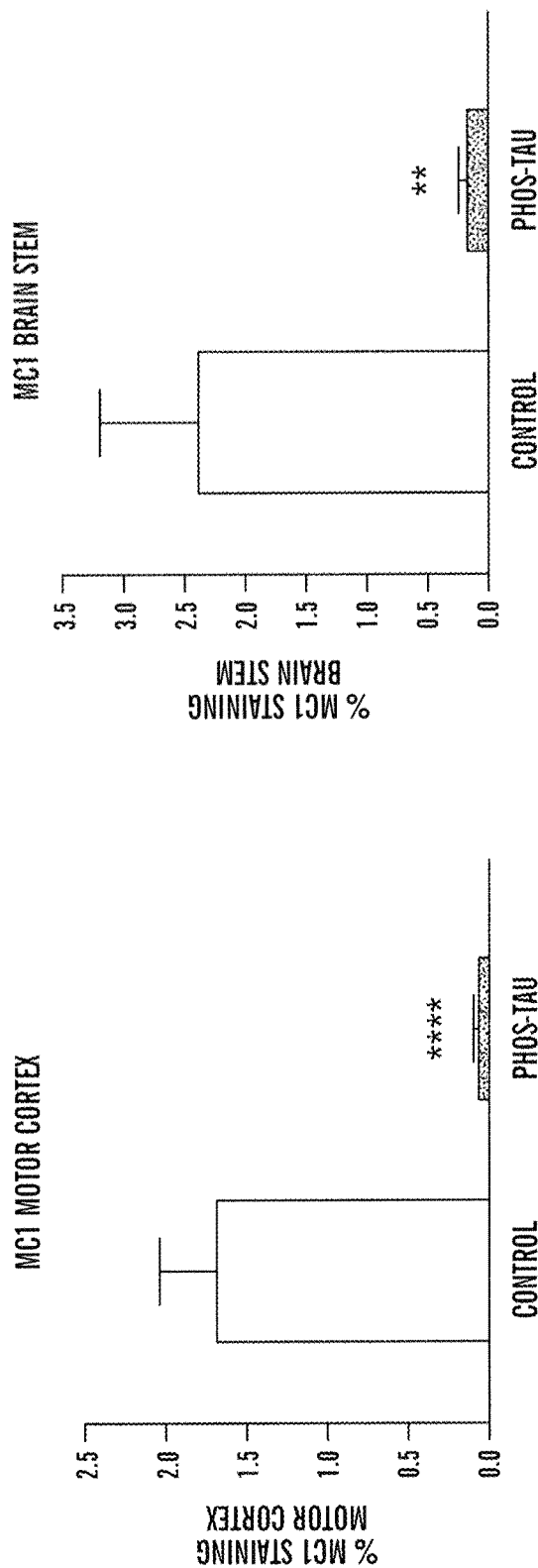

SEQUENCE LISTING

```
<160> NUMBER OF SEQ ID NOS: 26

<210> SEQ ID NO 1
<211> LENGTH: 30
<212> TYPE: PRT
<213> ORGANISM: Artificial
<220> FEATURE:
<223> OTHER INFORMATION: Tau 133-162

<400> SEQUENCE: 1

Asp Gly Thr Gly Ser Asp Lys Lys Ala Lys Gly Ala Asp Gly Lys
1               5                   10                  15

Thr Lys Ile Ala Thr Pro Arg Gly Ala Ala Pro Pro Gly Gln
            20                  25                  30

<210> SEQ ID NO 2
<211> LENGTH: 30
<212> TYPE: PRT
<213> ORGANISM: Artificial
<220> FEATURE:
<223> OTHER INFORMATION: Tau 379-409[P-Ser396,404]
<220> FEATURE:
<221> NAME/KEY: MOD_RES
<222> LOCATION: (18)..(18)
<223> OTHER INFORMATION: PHOSPHORYLATION
<220> FEATURE:
<221> NAME/KEY: MOD_RES
<222> LOCATION: (26)..(26)
<223> OTHER INFORMATION: PHOSPHORYLATION

<400> SEQUENCE: 2

Arg Glu Asn Ala Lys Ala Lys Thr Asp His Gly Ala Glu Ile Val Tyr
1               5                   10                  15

Lys Ser Pro Val Val Ser Gly Asp Thr Ser Pro Arg His Leu
```

```
                    20                  25                  30

<210> SEQ ID NO 3
<211> LENGTH: 30
<212> TYPE: PRT
<213> ORGANISM: Artificial
<220> FEATURE:
<223> OTHER INFORMATION: Tau 192-221 [P-Ser199,202,214,-Thr205,212]
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (14)..(14)
<223> OTHER INFORMATION: PHOSPHORYLATION
<220> FEATURE:
<221> NAME/KEY: MOD_RES
<222> LOCATION: (21)..(21)
<223> OTHER INFORMATION: PHOSPHORYLATION
<220> FEATURE:
<221> NAME/KEY: MOD_RES
<222> LOCATION: (23)..(23)
<223> OTHER INFORMATION: PHOSPHORYLATION

<400> SEQUENCE: 3

Gly Asp Arg Ser Gly Tyr Ser Ser Pro Gly Ser Pro Gly Thr Pro Gly
 1               5                  10                  15

Ser Arg Ser Arg Thr Pro Ser Leu Pro Thr Pro Pro Thr Arg
            20                  25                  30

<210> SEQ ID NO 4
<211> LENGTH: 30
<212> TYPE: PRT
<213> ORGANISM: Artificial
<220> FEATURE:
<223> OTHER INFORMATION: Tau221-250 [P-Thr231,-Ser235]
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (15)..(15)
<223> OTHER INFORMATION: PHOSPHORYLATION

<400> SEQUENCE: 4

Arg Glu Pro Lys Lys Val Ala Val Val Arg Thr Pro Pro Lys Ser Pro
 1               5                  10                  15

Ser Ser Ala Lys Ser Arg Leu Gln Thr Ala Pro Val Pro Met
            20                  25                  30

<210> SEQ ID NO 5
<211> LENGTH: 29
<212> TYPE: PRT
<213> ORGANISM: Artificial
<220> FEATURE:
<223> OTHER INFORMATION: Tau184-213

<400> SEQUENCE: 5

Ser Ser Gly Glu Pro Pro Lys Ser Gly Asp Arg Ser Gln Tyr Ser Ser
 1               5                  10                  15

Pro Gly Ser Pro Gly Thr Pro Gly Ser Arg Ser Arg Thr
            20                  25
```

```
<210> SEQ ID NO 6
<211> LENGTH: 30
<212> TYPE: PRT
<213> ORGANISM: Artificial
<220> FEATURE:
<223> OTHER INFORMATION: Tau1-30
<220> FEATURE:
<221> NAME/KEY: MOD_RES
<222> LOCATION: (18)..(18)
<223> OTHER INFORMATION: PHOSPHORYLATION
<220> FEATURE:
<221> NAME/KEY: MOD_RES
<222> LOCATION: (29)..(29)
<223> OTHER INFORMATION: PHOSPHORYLATION

<400> SEQUENCE: 6

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr
            20                  25                  30

<210> SEQ ID NO 7
<211> LENGTH: 31
<212> TYPE: PRT
<213> ORGANISM: Artificial
<220> FEATURE:
<223> OTHER INFORMATION: Tau30-60

<400> SEQUENCE: 7

Thr Met His Gln Asp Gln Glu Gly Asp Thr Asp Ala Gly Leu Lys Glu
1               5                   10                  15

Ser Pro Leu Gln Thr Pro Thr Glu Asp Gly Ser Glu Glu Pro Gly
            20                  25                  30

<210> SEQ ID NO 8
<211> LENGTH: 31
<212> TYPE: PRT
<213> ORGANISM: Artificial
<220> FEATURE:
<223> OTHER INFORMATION: Tau60-90

<400> SEQUENCE: 8

Gly Ser Glu Thr Ser Asp Ala Lys Ser Thr Pro Thr Ala Glu Asp Val
1               5                   10                  15

Thr Ala Pro Leu Val Asp Glu Gly Ala Pro Gly Lys Gln Ala Ala
            20                  25                  30

<210> SEQ ID NO 9
<211> LENGTH: 31
<212> TYPE: PRT
<213> ORGANISM: Artificial
<220> FEATURE:
<223> OTHER INFORMATION: Tau90-120

<400> SEQUENCE: 9

Ala Ala Gln Pro His Thr Glu Ile Pro Glu Gly Thr Thr Ala Glu Glu
1               5                   10                  15

Ala Gly Ile Gly Asp Thr Pro Ser Leu Glu Asp Glu Ala Ala Gly
            20                  25                  30

<210> SEQ ID NO 10
<211> LENGTH: 31
<212> TYPE: PRT
<213> ORGANISM: Artificial
<220> FEATURE:
<223> OTHER INFORMATION: Tau120-150
```

```
<400> SEQUENCE: 10

Gly His Val Thr Gln Ala Arg Met Val Ser Lys Ser Lys Asp Gly Thr
1               5                   10                  15

Gly Ser Asp Asp Lys Lys Ala Lys Gly Ala Asp Gly Lys Thr Lys
            20                  25                  30

<210> SEQ ID NO 11
<211> LENGTH: 31
<212> TYPE: PRT
<213> ORGANISM: Artificial
<220> FEATURE:
<223> OTHER INFORMATION: Tau150-180
<220> FEATURE:
<221> NAME/KEY: MOD_RES
<222> LOCATION: (26)..(26)
<223> OTHER INFORMATION: PHOSPHORYLATION

<400> SEQUENCE: 11

Lys Ile Ala Thr Pro Arg Gly Ala Ala Pro Pro Gly Gln Lys Gly Gln
1               5                   10                  15

Ala Asn Ala Thr Arg Ile Pro Ala Lys Thr Pro Ala Pro Lys
            20                  25                  30

<210> SEQ ID NO 12
<211> LENGTH: 31
<212> TYPE: PRT
<213> ORGANISM: Artificial
<220> FEATURE:
<223> OTHER INFORMATION: Tau180-210
<220> FEATURE:
<221> NAME/KEY: MOD_RES
<222> LOCATION: (2)..(2)
<223> OTHER INFORMATION: PHOSPHORYLATION
<220> FEATURE:
<221> NAME/KEY: MOD_RES
<222> LOCATION: (5)..(6)
<223> OTHER INFORMATION: PHOSPHORYLATION
<220> FEATURE:
<221> NAME/KEY: MOD_RES
<222> LOCATION: (18)..(20)
<223> OTHER INFORMATION: PHOSPHORYLATION
<220> FEATURE:
<221> NAME/KEY: MOD_RES
<222> LOCATION: (23)..(23)
<223> OTHER INFORMATION: PHOSPHORYLATION
<220> FEATURE:
<221> NAME/KEY: MOD_RES
<222> LOCATION: (26)..(26)
<223> OTHER INFORMATION: PHOSPHORYLATION
<220> FEATURE:
<221> NAME/KEY: MOD_RES
<222> LOCATION: (29)..(29)
<223> OTHER INFORMATION: PHOSPHORYLATION

<400> SEQUENCE: 12

Lys Thr Pro Pro Ser Ser Gly Glu Pro Pro Lys Ser Gly Asp Arg Ser
1               5                   10                  15

Gly Tyr Ser Ser Pro Gly Ser Pro Gly Thr Pro Gly Ser Arg Ser
            20                  25                  30

<210> SEQ ID NO 13
<211> LENGTH: 31
<212> TYPE: PRT
<213> ORGANISM: Artificial
<220> FEATURE:
<223> OTHER INFORMATION: Tau210-240
<220> FEATURE:
<221> NAME/KEY: MOD_RES
<222> LOCATION: (3)..(3)
<223> OTHER INFORMATION: PHOSPHORYLATION
```

```
<220> FEATURE:
<221> NAME/KEY: MOD_RES
<222> LOCATION: (5)..(5)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (22)..(22)
<223> OTHER INFORMATION: PHOSPHORYLATION
<220> FEATURE:
<221> NAME/KEY: MOD_RES
<222> LOCATION: (26)..(26)
<223> OTHER INFORMATION: PHOSPHORYLATION
<220> FEATURE:
<221> NAME/KEY: MOD_RES
<222> LOCATION: (28)..(29)
<223> OTHER INFORMATION: PHOSPHORYLATION

<400> SEQUENCE: 13

Ser Arg Thr Pro Ser Leu Pro Thr Pro Pro Thr Arg Glu Pro Lys Lys
1               5                   10                  15

Val Ala Val Val Arg Thr Pro Pro Lys Ser Pro Ser Ser Ala Lys
                20                  25                  30

<210> SEQ ID NO 14
<211> LENGTH: 31
<212> TYPE: PRT
<213> ORGANISM: Artificial
<220> FEATURE:
<223> OTHER INFORMATION: Tau240-270
<220> FEATURE:
<221> NAME/KEY: MOD_RES
<222> LOCATION: (23)..(23)
<223> OTHER INFORMATION: PHOSPHORYLATION

<400> SEQUENCE: 14

Lys Ser Arg Leu Gln Thr Ala Pro Val Pro Met Pro Asp Leu Lys Asn
1               5                   10                  15

Val Lys Ser Lys Ile Gly Ser Thr Glu Asn Leu Lys His Gln Pro
                20                  25                  30

<210> SEQ ID NO 15
<211> LENGTH: 31
<212> TYPE: PRT
<213> ORGANISM: Artificial
<220> FEATURE:
<223> OTHER INFORMATION: Tau270-300
<220> FEATURE:
<221> NAME/KEY: MOD_RES
<222> LOCATION: (24)..(24)
<223> OTHER INFORMATION: PHOSPHORYLATION

<400> SEQUENCE: 15

Pro Gly Gly Gly Lys Val Gln Ile Ile Asn Lys Lys Leu Asp Leu Ser
1               5                   10                  15

Asn Val Gln Ser Lys Cys Gly Ser Lys Asp Asn Ile Lys His Val
                20                  25                  30

<210> SEQ ID NO 16
<211> LENGTH: 31
<212> TYPE: PRT
<213> ORGANISM: Artificial
<220> FEATURE:
<223> OTHER INFORMATION: Tau300-330
<220> FEATURE:
<221> NAME/KEY: MOD_RES
<222> LOCATION: (11)..(11)
```

```
<223> OTHER INFORMATION: PHOSPHORYLATION
<220> FEATURE:
<221> NAME/KEY: MOD_RES
<222> LOCATION: (25)..(25)
<223> OTHER INFORMATION: PHOSPHORYLATION

<400> SEQUENCE: 16

Val Pro Gly Gly Gly Ser Val Gln Ile Val Tyr Lys Pro Val Asp Leu
1               5                   10                  15

Ser Lys Val Thr Ser Lys Cys Gly Ser Leu Gly Asn Ile His His
            20                  25                  30

<210> SEQ ID NO 17
<211> LENGTH: 31
<212> TYPE: PRT
<213> ORGANISM: Artificial
<220> FEATURE:
<223> OTHER INFORMATION: Tau330-360
<220> FEATURE:
<221> NAME/KEY: MOD_RES
<222> LOCATION: (27)..(27)
<223> OTHER INFORMATION: PHOSPHORYLATION

<400> SEQUENCE: 17

His Lys Pro Gly Gly Gly Gln Val Glu Val Lys Ser Glu Lys Leu Asp
1               5                   10                  15

Phe Lys Asp Arg Val Gln Ser Lys Ile Gly Ser Leu Asp Asn Ile
            20                  25                  30

<210> SEQ ID NO 18
<211> LENGTH: 31
<212> TYPE: PRT
<213> ORGANISM: Artificial
<220> FEATURE:
<223> OTHER INFORMATION: Tau360-390

<400> SEQUENCE: 18

Ile Thr His Val Pro Gly Gly Gly Asn Lys Lys Ile Glu Thr His Lys
1               5                   10                  15

Leu Thr Phe Arg Glu Asn Ala Lys Ala Lys Thr Asp His Gly Ala
            20                  25                  30

<210> SEQ ID NO 19
<211> LENGTH: 31
<212> TYPE: PRT
<213> ORGANISM: Artificial
<220> FEATURE:
<223> OTHER INFORMATION: Tau390-420
<220> FEATURE:
<221> NAME/KEY: MOD_RES
<222> LOCATION: (5)..(5)
<223> OTHER INFORMATION: PHOSPHORYLATION
<220> FEATURE:
<221> NAME/KEY: MOD_RES
<222> LOCATION: (7)..(7)
<223> OTHER INFORMATION: PHOSPHORYLATION
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (14)..(15)
<223> OTHER INFORMATION: PHOSPHORYLATION
<220> FEATURE:
<221> NAME/KEY: MOD_RES
<222> LOCATION: (20)..(20)
<223> OTHER INFORMATION: PHOSPHORYLATION
<220> FEATURE:
<221> NAME/KEY: MOD_RES
```

```
<222> LOCATION: (23)..(24)
<223> OTHER INFORMATION: PHOSPHORYLATION

<400> SEQUENCE: 19

Ala Glu Ile Val Tyr Lys Ser Pro Val Val Ser Gly Asp Thr Ser Pro
1               5                   10                  15

Arg His Leu Ser Asn Val Ser Ser Thr Gly Ser Ile Asp Met Val
            20                  25                  30

<210> SEQ ID NO 20
<211> LENGTH: 31
<212> TYPE: PRT
<213> ORGANISM: Artificial
<220> FEATURE:
<223> OTHER INFORMATION: Tau411-441
<220> FEATURE:
<221> NAME/KEY: MOD_RES
<222> LOCATION: (2)..(3)
<223> OTHER INFORMATION: PHOSPHORYLATION
<220> FEATURE:
<221> NAME/KEY: MOD_RES
<222> LOCATION: (12)..(12)
<223> OTHER INFORMATION: PHOSPHORYLATION

<400> SEQUENCE: 20

Val Ser Ser Thr Gly Ser Ile Asp Met Val Asp Ser Pro Gln Leu Ala
1               5                   10                  15

Thr Leu Ala Asp Glu Val Ser Ala Ser Leu Ala Lys Gln Gly Leu
            20                  25                  30

<210> SEQ ID NO 21
<211> LENGTH: 441
<212> TYPE: PRT
<213> ORGANISM: Artificial
<220> FEATURE:
<223> OTHER INFORMATION: Human Tau 2N4R
<220> FEATURE:
<221> NAME/KEY: MOD_RES
<222> LOCATION: (18)..(18)
<223> OTHER INFORMATION: PHOSPHORYLATION
<220> FEATURE:
<221> NAME/KEY: MOD_RES
<222> LOCATION: (29)..(29)
<223> OTHER INFORMATION: PHOSPHORYLATION
<220> FEATURE:
<221> NAME/KEY: MOD_RES
<222> LOCATION: (175)..(175)
<223> OTHER INFORMATION: PHOSPHORYLATION
<220> FEATURE:
<221> NAME/KEY: MOD_RES
<222> LOCATION: (181)..(181)
<223> OTHER INFORMATION: PHOSPHORYLATION
<220> FEATURE:
<221> NAME/KEY: MOD_RES
<222> LOCATION: (184)..(185)
<223> OTHER INFORMATION: PHOSPHORYLATION
<220> FEATURE:
<221> NAME/KEY: MOD_RES
<222> LOCATION: (197)..(199)
<223> OTHER INFORMATION: PHOSPHORYLATION
<220> FEATURE:
<221> NAME/KEY: MOD_RES
<222> LOCATION: (202)..(202)
<223> OTHER INFORMATION: PHOSPHORYLATION
<220> FEATURE:
<221> NAME/KEY: MOD_RES
<222> LOCATION: (205)..(205)
<223> OTHER INFORMATION: PHOSPHORYLATION
<220> FEATURE:
<221> NAME/KEY: MOD_RES
<222> LOCATION: (208)..(208)
<223> OTHER INFORMATION: PHOSPHORYLATION
<220> FEATURE:
```

```
<221> NAME/KEY: MOD_RES
<222> LOCATION: (212)..(212)
<223> OTHER INFORMATION: PHOSPHORYLATION
<220> FEATURE:
<221> NAME/KEY: MOD_RES
<222> LOCATION: (214)..(214)
<223> OTHER INFORMATION: PHOSPHORYLATION
<220> FEATURE:
<221> NAME/KEY: MOD_RES
<222> LOCATION: (217)..(217)
<223> OTHER INFORMATION: PHOSPHORYLATION
<220> FEATURE:
<221> NAME/KEY: MOD_RES
<222> LOCATION: (231)..(231)
<223> OTHER INFORMATION: PHOSPHORYLATION
<220> FEATURE:
<221> NAME/KEY: MOD_RES
<222> LOCATION: (235)..(235)
<223> OTHER INFORMATION: PHOSPHORYLATION
<220> FEATURE:
<221> NAME/KEY: MOD_RES
<222> LOCATION: (237)..(238)
<223> OTHER INFORMATION: PHOSPHORYLATION
<220> FEATURE:
<221> NAME/KEY: MOD_RES
<222> LOCATION: (262)..(262)
<223> OTHER INFORMATION: PHOSPHORYLATION
<220> FEATURE:
<221> NAME/KEY: MOD_RES
<222> LOCATION: (293)..(293)
<223> OTHER INFORMATION: PHOSPHORYLATION
<220> FEATURE:
<221> NAME/KEY: MOD_RES
<222> LOCATION: (310)..(310)
<223> OTHER INFORMATION: PHOSPHORYLATION
<220> FEATURE:
<221> NAME/KEY: MOD_RES
<222> LOCATION: (324)..(324)
<223> OTHER INFORMATION: PHOSPHORYLATION
<220> FEATURE:
<221> NAME/KEY: MOD_RES
<222> LOCATION: (356)..(356)
<223> OTHER INFORMATION: PHOSPHORYLATION
<220> FEATURE:
<221> NAME/KEY: MOD_RES
<222> LOCATION: (394)..(394)
<223> OTHER INFORMATION: PHOSPHORYLATION
<220> FEATURE:
<221> NAME/KEY: MOD_RES
<222> LOCATION: (396)..(396)
<223> OTHER INFORMATION: PHOSPHORYLATION
<220> FEATURE:
<221> NAME/KEY: MOD_RES
<222> LOCATION: (400)..(400)
<223> OTHER INFORMATION: PHOSPHORYLATION
<220> FEATURE:
<221> NAME/KEY: MOD_RES
<222> LOCATION: (403)..(404)
<223> OTHER INFORMATION: PHOSPHORYLATION
<220> FEATURE:
<221> NAME/KEY: MOD_RES
<222> LOCATION: (409)..(409)
<223> OTHER INFORMATION: PHOSPHORYLATION
<220> FEATURE:
<221> NAME/KEY: MOD_RES
<222> LOCATION: (412)..(413)
<223> OTHER INFORMATION: PHOSPHORYLATION
<220> FEATURE:
<221> NAME/KEY: MOD_RES
<222> LOCATION: (422)..(422)
<223> OTHER INFORMATION: PHOSPHORYLATION

<400> SEQUENCE: 21

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30
```

-continued

```
Gln Asp Gln Glu Gly Asp Thr Asp Ala Gly Leu Lys Glu Ser Pro Leu
         35                  40                  45

Gln Thr Pro Thr Glu Asp Gly Ser Glu Glu Pro Gly Ser Glu Thr Ser
 50                  55                  60

Asp Ala Lys Ser Thr Pro Thr Ala Glu Asp Val Thr Ala Pro Leu Val
 65                  70                  75                  80

Asp Glu Gly Ala Pro Gly Lys Gln Ala Ala Gln Pro His Thr Glu
                 85                  90                  95

Ile Pro Glu Gly Thr Thr Ala Glu Glu Ala Gly Ile Gly Asp Thr Pro
             100                 105                 110

Ser Leu Glu Asp Glu Ala Ala Gly His Val Thr Gln Ala Arg Met Val
         115                 120                 125

Ser Lys Ser Lys Asp Gly Thr Gly Ser Asp Asp Lys Lys Ala Lys Gly
     130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                 165                 170                 175

Pro Ala Pro Lys Thr Pro Pro Ser Ser Gly Glu Pro Pro Lys Ser Gly
             180                 185                 190

Asp Arg Ser Gly Tyr Ser Ser Pro Gly Ser Pro Gly Thr Pro Gly Ser
         195                 200                 205

Arg Ser Arg Thr Pro Ser Leu Pro Thr Pro Pro Thr Arg Glu Pro Lys
     210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                 245                 250                 255

Lys Ser Lys Ile Gly Ser Thr Glu Asn Leu Lys His Gln Pro Gly Gly
             260                 265                 270

Gly Lys Val Gln Ile Ile Asn Lys Lys Leu Asp Leu Ser Asn Val Gln
         275                 280                 285

Ser Lys Cys Gly Ser Lys Asp Asn Ile Lys His Val Pro Gly Gly Gly
     290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                 325                 330                 335

Val Glu Val Lys Ser Glu Lys Leu Asp Phe Lys Asp Arg Val Gln Ser
             340                 345                 350

Lys Ile Gly Ser Leu Asp Asn Ile Thr His Val Pro Gly Gly Gly Asn
         355                 360                 365

Lys Lys Ile Glu Thr His Lys Leu Thr Phe Arg Glu Asn Ala Lys Ala
     370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                 405                 410                 415

Ile Asp Met Val Asp Ser Pro Gln Leu Ala Thr Leu Ala Asp Glu Val
             420                 425                 430

Ser Ala Ser Leu Ala Lys Gln Gly Leu
         435                 440
```

```
<210> SEQ ID NO 22
<211> LENGTH: 410
<212> TYPE: PRT
<213> ORGANISM: Artificial
<220> FEATURE:
<223> OTHER INFORMATION: Human Tau 2N3R
<220> FEATURE:
<221> NAME/KEY: MOD_RES
<222> LOCATION: (18)..(18)
<223> OTHER INFORMATION: PHOSPHORYLATION
<220> FEATURE:
<221> NAME/KEY: MOD_RES
<222> LOCATION: (29)..(29)
<223> OTHER INFORMATION: PHOSPHORYLATION
<220> FEATURE:
<221> NAME/KEY: MOD_RES
<222> LOCATION: (175)..(175)
<223> OTHER INFORMATION: PHOSPHORYLATION
<220> FEATURE:
<221> NAME/KEY: MOD_RES
<222> LOCATION: (181)..(181)
<223> OTHER INFORMATION: PHOSPHORYLATION
<220> FEATURE:
<221> NAME/KEY: MOD_RES
<222> LOCATION: (184)..(185)
<223> OTHER INFORMATION: PHOSPHORYLATION
<220> FEATURE:
<221> NAME/KEY: MOD_RES
<222> LOCATION: (197)..(199)
<223> OTHER INFORMATION: PHOSPHORYLATION
<220> FEATURE:
<221> NAME/KEY: MOD_RES
<222> LOCATION: (202)..(202)
<223> OTHER INFORMATION: PHOSPHORYLATION
<220> FEATURE:
<221> NAME/KEY: MOD_RES
<222> LOCATION: (205)..(205)
<223> OTHER INFORMATION: PHOSPHORYLATION
<220> FEATURE:
<221> NAME/KEY: MOD_RES
<222> LOCATION: (208)..(208)
<223> OTHER INFORMATION: PHOSPHORYLATION
<220> FEATURE:
<221> NAME/KEY: MOD_RES
<222> LOCATION: (212)..(212)
<223> OTHER INFORMATION: PHOSPHORYLATION
<220> FEATURE:
<221> NAME/KEY: MOD_RES
<222> LOCATION: (214)..(214)
<223> OTHER INFORMATION: PHOSPHORYLATION
<220> FEATURE:
<221> NAME/KEY: MOD_RES
<222> LOCATION: (217)..(217)
<223> OTHER INFORMATION: PHOSPHORYLATION
<220> FEATURE:
<221> NAME/KEY: MOD_RES
<222> LOCATION: (231)..(231)
<223> OTHER INFORMATION: PHOSPHORYLATION
<220> FEATURE:
<221> NAME/KEY: MOD_RES
<222> LOCATION: (235)..(235)
<223> OTHER INFORMATION: PHOSPHORYLATION
<220> FEATURE:
<221> NAME/KEY: MOD_RES
<222> LOCATION: (237)..(238)
<223> OTHER INFORMATION: PHOSPHORYLATION
<220> FEATURE:
<221> NAME/KEY: MOD_RES
<222> LOCATION: (262)..(262)
<223> OTHER INFORMATION: PHOSPHORYLATION
<220> FEATURE:
<221> NAME/KEY: MOD_RES
<222> LOCATION: (279)..(279)
<223> OTHER INFORMATION: PHOSPHORYLATION
<220> FEATURE:
<221> NAME/KEY: MOD_RES
<222> LOCATION: (293)..(293)
<223> OTHER INFORMATION: PHOSPHORYLATION
```

```
<220> FEATURE:
<221> NAME/KEY: MOD_RES
<222> LOCATION: (325)..(325)
<223> OTHER INFORMATION: PHOSPHORYLATION
<220> FEATURE:
<221> NAME/KEY: MOD_RES
<222> LOCATION: (363)..(363)
<223> OTHER INFORMATION: PHOSPHORYLATION
<220> FEATURE:
<221> NAME/KEY: MOD_RES
<222> LOCATION: (365)..(365)
<223> OTHER INFORMATION: PHOSPHORYLATION
<220> FEATURE:
<221> NAME/KEY: MOD_RES
<222> LOCATION: (369)..(369)
<223> OTHER INFORMATION: PHOSPHORYLATION
<220> FEATURE:
<221> NAME/KEY: MOD_RES
<222> LOCATION: (372)..(373)
<223> OTHER INFORMATION: PHOSPHORYLATION
<220> FEATURE:
<221> NAME/KEY: MOD_RES
<222> LOCATION: (378)..(378)
<223> OTHER INFORMATION: PHOSPHORYLATION
<220> FEATURE:
<221> NAME/KEY: MOD_RES
<222> LOCATION: (381)..(382)
<223> OTHER INFORMATION: PHOSPHORYLATION
<220> FEATURE:
<221> NAME/KEY: MOD_RES
<222> LOCATION: (391)..(391)
<223> OTHER INFORMATION: PHOSPHORYLATION

<400> SEQUENCE: 22

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240
```

```
Ser Arg Leu Gln Thr Ala Pro Val Pro Met Pro Asp Leu Lys Asn Val
            245                 250                 255

Lys Ser Lys Ile Gly Ser Thr Glu Asn Leu Lys His Gln Pro Gly Gly
        260                 265                 270

Gly Lys Val Gln Ile Val Tyr Lys Pro Val Asp Leu Ser Lys Val Thr
        275                 280                 285

Ser Lys Cys Gly Ser Leu Gly Asn Ile His His Lys Pro Gly Gly Gly
290                 295                 300

Gln Val Glu Val Lys Ser Glu Lys Leu Asp Phe Lys Asp Arg Val Gln
305                 310                 315                 320

Ser Lys Ile Gly Ser Leu Asp Asn Ile Thr His Val Pro Gly Gly Gly
            325                 330                 335

Asn Lys Lys Ile Glu Thr His Lys Leu Thr Phe Arg Glu Asn Ala Lys
            340                 345                 350

Ala Lys Thr Asp His Gly Ala Glu Ile Val Tyr Lys Ser Pro Val Val
            355                 360                 365

Ser Gly Asp Thr Ser Pro Arg His Leu Ser Asn Val Ser Ser Thr Gly
        370                 375                 380

Ser Ile Asp Met Val Asp Ser Pro Gln Leu Ala Thr Leu Ala Asp Glu
385                 390                 395                 400

Val Ser Ala Ser Leu Ala Lys Gln Gly Leu
            405                 410

<210> SEQ ID NO 23
<211> LENGTH: 412
<212> TYPE: PRT
<213> ORGANISM: Artificial
<220> FEATURE:
<223> OTHER INFORMATION: Human Tau 1N4R
<220> FEATURE:
<221> NAME/KEY: MOD_RES
<222> LOCATION: (18)..(18)
<223> OTHER INFORMATION: PHOSPHORYLATION
<220> FEATURE:
<221> NAME/KEY: MOD_RES
<222> LOCATION: (29)..(29)
<223> OTHER INFORMATION: PHOSPHORYLATION
<220> FEATURE:
<221> NAME/KEY: MOD_RES
<222> LOCATION: (146)..(146)
<223> OTHER INFORMATION: PHOSPHORYLATION
<220> FEATURE:
<221> NAME/KEY: MOD_RES
<222> LOCATION: (152)..(152)
<223> OTHER INFORMATION: PHOSPHORYLATION
<220> FEATURE:
<221> NAME/KEY: MOD_RES
<222> LOCATION: (155)..(156)
<223> OTHER INFORMATION: PHOSPHORYLATION
<220> FEATURE:
<221> NAME/KEY: MOD_RES
<222> LOCATION: (168)..(170)
<223> OTHER INFORMATION: PHOSPHORYLATION
<220> FEATURE:
<221> NAME/KEY: MOD_RES
<222> LOCATION: (173)..(173)
<223> OTHER INFORMATION: PHOSPHORYLATION
<220> FEATURE:
<221> NAME/KEY: MOD_RES
<222> LOCATION: (176)..(176)
<223> OTHER INFORMATION: PHOSPHORYLATION
<220> FEATURE:
<221> NAME/KEY: MOD_RES
<222> LOCATION: (179)..(179)
<223> OTHER INFORMATION: PHOSPHORYLATION
<220> FEATURE:
<221> NAME/KEY: MOD_RES
```

```
<222> LOCATION: (183)..(183)
<223> OTHER INFORMATION: PHOSPHORYLATION
<220> FEATURE:
<221> NAME/KEY: MOD_RES
<222> LOCATION: (185)..(185)
<223> OTHER INFORMATION: PHOSPHORYLATION
<220> FEATURE:
<221> NAME/KEY: MOD_RES
<222> LOCATION: (188)..(188)
<223> OTHER INFORMATION: PHOSPHORYLATION
<220> FEATURE:
<221> NAME/KEY: MOD_RES
<222> LOCATION: (202)..(202)
<223> OTHER INFORMATION: PHOSPHORYLATION
<220> FEATURE:
<221> NAME/KEY: MOD_RES
<222> LOCATION: (206)..(206)
<223> OTHER INFORMATION: PHOSPHORYLATION
<220> FEATURE:
<221> NAME/KEY: MOD_RES
<222> LOCATION: (208)..(209)
<223> OTHER INFORMATION: PHOSPHORYLATION
<220> FEATURE:
<221> NAME/KEY: MOD_RES
<222> LOCATION: (233)..(233)
<223> OTHER INFORMATION: PHOSPHORYLATION
<220> FEATURE:
<221> NAME/KEY: MOD_RES
<222> LOCATION: (264)..(264)
<223> OTHER INFORMATION: PHOSPHORYLATION
<220> FEATURE:
<221> NAME/KEY: MOD_RES
<222> LOCATION: (281)..(281)
<223> OTHER INFORMATION: PHOSPHORYLATION
<220> FEATURE:
<221> NAME/KEY: MOD_RES
<222> LOCATION: (295)..(295)
<223> OTHER INFORMATION: PHOSPHORYLATION
<220> FEATURE:
<221> NAME/KEY: MOD_RES
<222> LOCATION: (327)..(327)
<223> OTHER INFORMATION: PHOSPHORYLATION
<220> FEATURE:
<221> NAME/KEY: MOD_RES
<222> LOCATION: (365)..(365)
<223> OTHER INFORMATION: PHOSPHORYLATION
<220> FEATURE:
<221> NAME/KEY: MOD_RES
<222> LOCATION: (367)..(367)
<223> OTHER INFORMATION: PHOSPHORYLATION
<220> FEATURE:
<221> NAME/KEY: MOD_RES
<222> LOCATION: (371)..(371)
<223> OTHER INFORMATION: PHOSPHORYLATION
<220> FEATURE:
<221> NAME/KEY: MOD_RES
<222> LOCATION: (374)..(375)
<223> OTHER INFORMATION: PHOSPHORYLATION
<220> FEATURE:
<221> NAME/KEY: MOD_RES
<222> LOCATION: (380)..(380)
<223> OTHER INFORMATION: PHOSPHORYLATION
<220> FEATURE:
<221> NAME/KEY: MOD_RES
<222> LOCATION: (383)..(384)
<223> OTHER INFORMATION: PHOSPHORYLATION
<220> FEATURE:
<221> NAME/KEY: MOD_RES
<222> LOCATION: (393)..(393)
<223> OTHER INFORMATION: PHOSPHORYLATION

<400> SEQUENCE: 23

Met Ala Glu Pro Arg Gln Glu Phe Glu Val Met Glu Asp His Ala Gly
 1               5                  10                  15

Thr Tyr Gly Leu Gly Asp Arg Lys Asp Gln Gly Gly Tyr Thr Met His
            20                  25                  30
```

-continued

Gln Asp Gln Glu Gly Asp Thr Asp Ala Gly Leu Lys Glu Ser Pro Leu
             35                  40                  45

Gln Thr Pro Thr Glu Asp Gly Ser Glu Pro Gly Ser Glu Thr Ser
 50                  55                  60

Asp Ala Lys Ser Thr Pro Thr Ala Glu Ala Glu Glu Ala Gly Ile Gly
 65                  70                  75                  80

Asp Thr Pro Ser Leu Glu Asp Glu Ala Ala Gly His Val Thr Gln Ala
                 85                  90                  95

Arg Met Val Ser Lys Ser Lys Asp Gly Thr Gly Ser Asp Asp Lys Lys
            100                 105                 110

Ala Lys Gly Ala Asp Gly Lys Thr Lys Ile Ala Thr Pro Arg Gly Ala
        115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
        195                 200                 205

Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240

Pro Gly Gly Gly Lys Val Gln Ile Ile Asn Lys Lys Leu Asp Leu Ser
                245                 250                 255

Asn Val Gln Ser Lys Cys Gly Ser Lys Asp Asn Ile Lys His Val Pro
            260                 265                 270

Gly Gly Gly Ser Val Gln Ile Val Tyr Lys Pro Val Asp Leu Ser Lys
        275                 280                 285

Val Thr Ser Lys Cys Gly Ser Leu Gly Asn Ile His His Lys Pro Gly
    290                 295                 300

Gly Gly Gln Val Glu Val Lys Ser Glu Lys Leu Asp Phe Lys Asp Arg
305                 310                 315                 320

Val Gln Ser Lys Ile Gly Ser Leu Asp Asn Ile Thr His Val Pro Gly
                325                 330                 335

Gly Gly Asn Lys Lys Ile Glu Thr His Lys Leu Thr Phe Arg Glu Asn
            340                 345                 350

Ala Lys Ala Lys Thr Asp His Gly Ala Glu Ile Val Tyr Lys Ser Pro
        355                 360                 365

Val Val Ser Gly Asp Thr Ser Pro Arg His Leu Ser Asn Val Ser Ser
    370                 375                 380

Thr Gly Ser Ile Asp Met Val Asp Ser Pro Gln Leu Ala Thr Leu Ala
385                 390                 395                 400

Asp Glu Val Ser Ala Ser Leu Ala Lys Gln Gly Leu
                405                 410

<210> SEQ ID NO 24
<211> LENGTH: 383
<212> TYPE: PRT
<213> ORGANISM: Artificial
<220> FEATURE:
<223> OTHER INFORMATION: Human Tau 0N4R -continued

```
<220> FEATURE:
<221> NAME/KEY: MOD_RES
<222> LOCATION: (18)..(18)
<223> OTHER INFORMATION: PHOSPHORYLATION
<220> FEATURE:
<221> NAME/KEY: MOD_RES
<222> LOCATION: (29)..(29)
<223> OTHER INFORMATION: PHOSPHORYLATION
<220> FEATURE:
<221> NAME/KEY: MOD_RES
<222> LOCATION: (117)..(117)
<223> OTHER INFORMATION: PHOSPHORYLATION
<220> FEATURE:
<221> NAME/KEY: MOD_RES
<222> LOCATION: (123)..(123)
<223> OTHER INFORMATION: PHOSPHORYLATION
<220> FEATURE:
<221> NAME/KEY: MOD_RES
<222> LOCATION: (126)..(127)
<223> OTHER INFORMATION: PHOSPHORYLATION
<220> FEATURE:
<221> NAME/KEY: MOD_RES
<222> LOCATION: (139)..(141)
<223> OTHER INFORMATION: PHOSPHORYLATION
<220> FEATURE:
<221> NAME/KEY: MOD_RES
<222> LOCATION: (144)..(144)
<223> OTHER INFORMATION: PHOSPHORYLATION
<220> FEATURE:
<221> NAME/KEY: MOD_RES
<222> LOCATION: (147)..(147)
<223> OTHER INFORMATION: PHOSPHORYLATION
<220> FEATURE:
<221> NAME/KEY: MOD_RES
<222> LOCATION: (150)..(150)
<223> OTHER INFORMATION: PHOSPHORYLATION
<220> FEATURE:
<221> NAME/KEY: MOD_RES
<222> LOCATION: (154)..(154)
<223> OTHER INFORMATION: PHOSPHORYLATION
<220> FEATURE:
<221> NAME/KEY: MOD_RES
<222> LOCATION: (156)..(156)
<223> OTHER INFORMATION: PHOSPHORYLATION
<220> FEATURE:
<221> NAME/KEY: MOD_RES
<222> LOCATION: (159)..(159)
<223> OTHER INFORMATION: PHOSPHORYLATION
<220> FEATURE:
<221> NAME/KEY: MOD_RES
<222> LOCATION: (173)..(173)
<223> OTHER INFORMATION: PHOSPHORYLATION
<220> FEATURE:
<221> NAME/KEY: MOD_RES
<222> LOCATION: (177)..(177)
<223> OTHER INFORMATION: PHOSPHORYLATION
<220> FEATURE:
<221> NAME/KEY: MOD_RES
<222> LOCATION: (179)..(180)
<223> OTHER INFORMATION: PHOSPHORYLATION
<220> FEATURE:
<221> NAME/KEY: MOD_RES
<222> LOCATION: (204)..(204)
<223> OTHER INFORMATION: PHOSPHORYLATION
<220> FEATURE:
<221> NAME/KEY: MOD_RES
<222> LOCATION: (235)..(235)
<223> OTHER INFORMATION: PHOSPHORYLATION
<220> FEATURE:
<221> NAME/KEY: MOD_RES
<222> LOCATION: (252)..(252)
<223> OTHER INFORMATION: PHOSPHORYLATION
<220> FEATURE:
<221> NAME/KEY: MOD_RES
<222> LOCATION: (266)..(266)
<223> OTHER INFORMATION: PHOSPHORYLATION
<220> FEATURE:
<221> NAME/KEY: MOD_RES
<222> LOCATION: (298)..(298)
```

```
<223> OTHER INFORMATION: PHOSPHORYLATION
<220> FEATURE:
<221> NAME/KEY: MOD_RES
<222> LOCATION: (336)..(336)
<223> OTHER INFORMATION: PHOSPHORYLATION
<220> FEATURE:
<221> NAME/KEY: MOD_RES
<222> LOCATION: (338)..(338)
<223> OTHER INFORMATION: PHOSPHORYLATION
<220> FEATURE:
<221> NAME/KEY: MOD_RES
<222> LOCATION: (342)..(342)
<223> OTHER INFORMATION: PHOSPHORYLATION
<220> FEATURE:
<221> NAME/KEY: MOD_RES
<222> LOCATION: (345)..(346)
<223> OTHER INFORMATION: PHOSPHORYLATION
<220> FEATURE:
<221> NAME/KEY: MOD_RES
<222> LOCATION: (351)..(351)
<223> OTHER INFORMATION: PHOSPHORYLATION
<220> FEATURE:
<221> NAME/KEY: MOD_RES
<222> LOCATION: (354)..(355)
<223> OTHER INFORMATION: PHOSPHORYLATION
<220> FEATURE:
<221> NAME/KEY: MOD_RES
<222> LOCATION: (364)..(364)
<223> OTHER INFORMATION: PHOSPHORYLATION

<400> SEQUENCE: 24

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Ile Asn Lys Lys Leu
    210                 215                 220

Asp Leu Ser Asn Val Gln Ser Lys Cys Gly Ser Lys Asp Asn Ile Lys
225                 230                 235                 240

His Val Pro Gly Gly Gly Ser Val Gln Ile Val Tyr Lys Pro Val Asp
                245                 250                 255
```

-continued

```
Leu Ser Lys Val Thr Ser Lys Cys Gly Ser Leu Gly Asn Ile His His
            260                 265                 270

Lys Pro Gly Gly Gly Gln Val Glu Val Lys Ser Glu Lys Leu Asp Phe
        275                 280                 285

Lys Asp Arg Val Gln Ser Lys Ile Gly Ser Leu Asp Asn Ile Thr His
290                 295                 300

Val Pro Gly Gly Gly Asn Lys Lys Ile Glu Thr His Lys Leu Thr Phe
305                 310                 315                 320

Arg Glu Asn Ala Lys Ala Lys Thr Asp His Gly Ala Glu Ile Val Tyr
                325                 330                 335

Lys Ser Pro Val Val Ser Gly Asp Thr Ser Pro Arg His Leu Ser Asn
            340                 345                 350

Val Ser Ser Thr Gly Ser Ile Asp Met Val Asp Ser Pro Gln Leu Ala
        355                 360                 365

Thr Leu Ala Asp Glu Val Ser Ala Ser Leu Ala Lys Gln Gly Leu
    370                 375                 380

<210> SEQ ID NO 25
<211> LENGTH: 381
<212> TYPE: PRT
<213> ORGANISM: Artificial
<220> FEATURE:
<223> OTHER INFORMATION: Human Tau 1N3R
<220> FEATURE:
<221> NAME/KEY: MOD_RES
<222> LOCATION: (18)..(18)
<223> OTHER INFORMATION: PHOSPHORYLATION
<220> FEATURE:
<221> NAME/KEY: MOD_RES
<222> LOCATION: (29)..(29)
<223> OTHER INFORMATION: PHOSPHORYLATION
<220> FEATURE:
<221> NAME/KEY: MOD_RES
<222> LOCATION: (146)..(146)
<223> OTHER INFORMATION: PHOSPHORYLATION
<220> FEATURE:
<221> NAME/KEY: MOD_RES
<222> LOCATION: (152)..(152)
<223> OTHER INFORMATION: PHOSPHORYLATION
<220> FEATURE:
<221> NAME/KEY: MOD_RES
<222> LOCATION: (155)..(156)
<223> OTHER INFORMATION: PHOSPHORYLATION
<220> FEATURE:
<221> NAME/KEY: MOD_RES
<222> LOCATION: (168)..(170)
<223> OTHER INFORMATION: PHOSPHORYLATION
<220> FEATURE:
<221> NAME/KEY: MOD_RES
<222> LOCATION: (173)..(173)
<223> OTHER INFORMATION: PHOSPHORYLATION
<220> FEATURE:
<221> NAME/KEY: MOD_RES
<222> LOCATION: (176)..(176)
<223> OTHER INFORMATION: PHOSPHORYLATION
<220> FEATURE:
<221> NAME/KEY: MOD_RES
<222> LOCATION: (179)..(179)
<223> OTHER INFORMATION: PHOSPHORYLATION
<220> FEATURE:
<221> NAME/KEY: MOD_RES
<222> LOCATION: (183)..(183)
<223> OTHER INFORMATION: PHOSPHORYLATION
<220> FEATURE:
<221> NAME/KEY: MOD_RES
<222> LOCATION: (185)..(185)
<223> OTHER INFORMATION: PHOSPHORYLATION
<220> FEATURE:
<221> NAME/KEY: MOD_RES
<222> LOCATION: (188)..(188)
```

```
<223> OTHER INFORMATION: PHOSPHORYLATION
<220> FEATURE:
<221> NAME/KEY: MOD_RES
<222> LOCATION: (202)..(202)
<223> OTHER INFORMATION: PHOSPHORYLATION
<220> FEATURE:
<221> NAME/KEY: MOD_RES
<222> LOCATION: (206)..(206)
<223> OTHER INFORMATION: PHOSPHORYLATION
<220> FEATURE:
<221> NAME/KEY: MOD_RES
<222> LOCATION: (208)..(209)
<223> OTHER INFORMATION: PHOSPHORYLATION
<220> FEATURE:
<221> NAME/KEY: MOD_RES
<222> LOCATION: (233)..(233)
<223> OTHER INFORMATION: PHOSPHORYLATION
<220> FEATURE:
<221> NAME/KEY: MOD_RES
<222> LOCATION: (250)..(250)
<223> OTHER INFORMATION: PHOSPHORYLATION
<220> FEATURE:
<221> NAME/KEY: MOD_RES
<222> LOCATION: (264)..(264)
<223> OTHER INFORMATION: PHOSPHORYLATION
<220> FEATURE:
<221> NAME/KEY: MOD_RES
<222> LOCATION: (296)..(296)
<223> OTHER INFORMATION: PHOSPHORYLATION
<220> FEATURE:
<221> NAME/KEY: MOD_RES
<222> LOCATION: (334)..(334)
<223> OTHER INFORMATION: PHOSPHORYLATION
<220> FEATURE:
<221> NAME/KEY: MOD_RES
<222> LOCATION: (336)..(336)
<223> OTHER INFORMATION: PHOSPHORYLATION
<220> FEATURE:
<221> NAME/KEY: MOD_RES
<222> LOCATION: (340)..(340)
<223> OTHER INFORMATION: PHOSPHORYLATION
<220> FEATURE:
<221> NAME/KEY: MOD_RES
<222> LOCATION: (343)..(344)
<223> OTHER INFORMATION: PHOSPHORYLATION
<220> FEATURE:
<221> NAME/KEY: MOD_RES
<222> LOCATION: (349)..(349)
<223> OTHER INFORMATION: PHOSPHORYLATION
<220> FEATURE:
<221> NAME/KEY: MOD_RES
<222> LOCATION: (352)..(353)
<223> OTHER INFORMATION: PHOSPHORYLATION
<220> FEATURE:
<221> NAME/KEY: MOD_RES
<222> LOCATION: (362)..(362)
<223> OTHER INFORMATION: PHOSPHORYLATION

<400> SEQUENCE: 25
```

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Ala Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys

-continued

```
                 100                 105                 110
Ala Lys Gly Ala Asp Gly Lys Thr Lys Ile Ala Thr Pro Arg Gly Ala
            115                 120                 125
Ala Pro Pro Gly Gln Lys Gly Gln Ala Asn Ala Thr Arg Ile Pro Ala
        130                 135                 140
Lys Thr Pro Pro Ala Pro Lys Thr Pro Pro Ser Ser Gly Glu Pro Pro
145                 150                 155                 160
Lys Ser Gly Asp Arg Ser Gly Tyr Ser Ser Pro Gly Ser Pro Gly Thr
                165                 170                 175
Pro Gly Ser Arg Ser Arg Thr Pro Ser Leu Pro Thr Pro Pro Thr Arg
            180                 185                 190
Glu Pro Lys Lys Val Ala Val Val Arg Thr Pro Pro Lys Ser Pro Ser
        195                 200                 205
Ser Ala Lys Ser Arg Leu Gln Thr Ala Pro Val Pro Met Pro Asp Leu
    210                 215                 220
Lys Asn Val Lys Ser Lys Ile Gly Ser Thr Glu Asn Leu Lys His Gln
225                 230                 235                 240
Pro Gly Gly Gly Lys Val Gln Ile Val Tyr Lys Pro Val Asp Leu Ser
                245                 250                 255
Lys Val Thr Ser Lys Cys Gly Ser Leu Gly Asn Ile His His Lys Pro
            260                 265                 270
Gly Gly Gly Gln Val Glu Val Lys Ser Glu Lys Leu Asp Phe Lys Asp
        275                 280                 285
Arg Val Gln Ser Lys Ile Gly Ser Leu Asp Asn Ile Thr His Val Pro
    290                 295                 300
Gly Gly Gly Asn Lys Lys Ile Glu Thr His Lys Leu Thr Phe Arg Glu
305                 310                 315                 320
Asn Ala Lys Ala Lys Thr Asp His Gly Ala Glu Ile Val Tyr Lys Ser
                325                 330                 335
Pro Val Val Ser Gly Asp Thr Ser Pro Arg His Leu Ser Asn Val Ser
            340                 345                 350
Ser Thr Gly Ser Ile Asp Met Val Asp Ser Pro Gln Leu Ala Thr Leu
        355                 360                 365
Ala Asp Glu Val Ser Ala Ser Leu Ala Lys Gln Gly Leu
    370                 375                 380

<210> SEQ ID NO 26
<211> LENGTH: 352
<212> TYPE: PRT
<213> ORGANISM: Artificial
<220> FEATURE:
<223> OTHER INFORMATION: Human Tau 0N3R
<220> FEATURE:
<221> NAME/KEY: MOD_RES
<222> LOCATION: (18)..(18)
<223> OTHER INFORMATION: PHOSPHORYLATION
<220> FEATURE:
<221> NAME/KEY: MOD_RES
<222> LOCATION: (29)..(29)
<223> OTHER INFORMATION: PHOSPHORYLATION
<220> FEATURE:
<221> NAME/KEY: MOD_RES
<222> LOCATION: (117)..(117)
<223> OTHER INFORMATION: PHOSPHORYLATION
<220> FEATURE:
<221> NAME/KEY: MOD_RES
<222> LOCATION: (123)..(123)
<223> OTHER INFORMATION: PHOSPHORYLATION
<220> FEATURE:
<221> NAME/KEY: MOD_RES
<222> LOCATION: (126)..(127)
```

```
<223> OTHER INFORMATION: PHOSPHORYLATION
<220> FEATURE:
<221> NAME/KEY: MOD_RES
<222> LOCATION: (139)..(141)
<223> OTHER INFORMATION: PHOSPHORYLATION
<220> FEATURE:
<221> NAME/KEY: MOD_RES
<222> LOCATION: (144)..(144)
<223> OTHER INFORMATION: PHOSPHORYLATION
<220> FEATURE:
<221> NAME/KEY: MOD_RES
<222> LOCATION: (147)..(147)
<223> OTHER INFORMATION: PHOSPHORYLATION
<220> FEATURE:
<221> NAME/KEY: MOD_RES
<222> LOCATION: (150)..(150)
<223> OTHER INFORMATION: PHOSPHORYLATION
<220> FEATURE:
<221> NAME/KEY: MOD_RES
<222> LOCATION: (154)..(154)
<223> OTHER INFORMATION: PHOSPHORYLATION
<220> FEATURE:
<221> NAME/KEY: MOD_RES
<222> LOCATION: (156)..(156)
<223> OTHER INFORMATION: PHOSPHORYLATION
<220> FEATURE:
<221> NAME/KEY: MOD_RES
<222> LOCATION: (159)..(159)
<223> OTHER INFORMATION: PHOSPHORYLATION
<220> FEATURE:
<221> NAME/KEY: MOD_RES
<222> LOCATION: (173)..(173)
<223> OTHER INFORMATION: PHOSPHORYLATION
<220> FEATURE:
<221> NAME/KEY: MOD_RES
<222> LOCATION: (177)..(177)
<223> OTHER INFORMATION: PHOSPHORYLATION
<220> FEATURE:
<221> NAME/KEY: MOD_RES
<222> LOCATION: (179)..(180)
<223> OTHER INFORMATION: PHOSPHORYLATION
<220> FEATURE:
<221> NAME/KEY: MOD_RES
<222> LOCATION: (204)..(204)
<223> OTHER INFORMATION: PHOSPHORYLATION
<220> FEATURE:
<221> NAME/KEY: MOD_RES
<222> LOCATION: (221)..(221)
<223> OTHER INFORMATION: PHOSPHORYLATION
<220> FEATURE:
<221> NAME/KEY: MOD_RES
<222> LOCATION: (235)..(235)
<223> OTHER INFORMATION: PHOSPHORYLATION
<220> FEATURE:
<221> NAME/KEY: MOD_RES
<222> LOCATION: (267)..(267)
<223> OTHER INFORMATION: PHOSPHORYLATION
<220> FEATURE:
<221> NAME/KEY: MOD_RES
<222> LOCATION: (305)..(305)
<223> OTHER INFORMATION: PHOSPHORYLATION
<220> FEATURE:
<221> NAME/KEY: MOD_RES
<222> LOCATION: (307)..(307)
<223> OTHER INFORMATION: PHOSPHORYLATION
<220> FEATURE:
<221> NAME/KEY: MOD_RES
<222> LOCATION: (311)..(311)
<223> OTHER INFORMATION: PHOSPHORYLATION
<220> FEATURE:
<221> NAME/KEY: MOD_RES
<222> LOCATION: (314)..(315)
<223> OTHER INFORMATION: PHOSPHORYLATION
<220> FEATURE:
<221> NAME/KEY: MOD_RES
<222> LOCATION: (320)..(320)
<223> OTHER INFORMATION: PHOSPHORYLATION
<220> FEATURE:
<221> NAME/KEY: MOD_RES
```

```
<222> LOCATION: (323)..(324)
<223> OTHER INFORMATION: PHOSPHORYLATION
<220> FEATURE:
<221> NAME/KEY: MOD_RES
<222> LOCATION: (333)..(333)
<223> OTHER INFORMATION: PHOSPHORYLATION

<400> SEQUENCE: 26

Met Ala Glu Pro Arg Gln Glu Phe Glu Val Met Glu Asp His Ala Gly
  1               5                  10                  15

Thr Tyr Gly Leu Gly Asp Arg Lys Asp Gln Gly Gly Tyr Thr Met His
             20                  25                  30

Gln Asp Gln Glu Gly Asp Thr Asp Ala Gly Leu Lys Ala Glu Glu Ala
         35                  40                  45

Gly Ile Gly Asp Thr Pro Ser Leu Glu Asp Glu Ala Ala Gly His Val
     50                  55                  60

Thr Gln Ala Arg Met Val Ser Lys Ser Lys Asp Gly Thr Gly Ser Asp
 65                  70                  75                  80

Asp Lys Lys Ala Lys Gly Ala Asp Gly Lys Thr Lys Ile Ala Thr Pro
                 85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Val Tyr Lys Pro Val
    210                 215                 220

Asp Leu Ser Lys Val Thr Ser Lys Cys Gly Ser Leu Gly Asn Ile His
225                 230                 235                 240

His Lys Pro Gly Gly Gly Gln Val Glu Val Lys Ser Glu Lys Leu Asp
                245                 250                 255

Phe Lys Asp Arg Val Gln Ser Lys Ile Gly Ser Leu Asp Asn Ile Thr
            260                 265                 270

His Val Pro Gly Gly Gly Asn Lys Lys Ile Glu Thr His Lys Leu Thr
        275                 280                 285

Phe Arg Glu Asn Ala Lys Ala Lys Thr Asp His Gly Ala Glu Ile Val
    290                 295                 300

Tyr Lys Ser Pro Val Val Ser Gly Asp Thr Ser Pro Arg His Leu Ser
305                 310                 315                 320

Asn Val Ser Ser Thr Gly Ser Ile Asp Met Val Asp Ser Pro Gln Leu
                325                 330                 335

Ala Thr Leu Ala Asp Glu Val Ser Ala Ser Leu Ala Lys Gln Gly Leu
            340                 345                 350
```

IMMUNOTHERAPY FOR CLEARING PATHOLOGICAL TAU CONFORMERS

CROSS-REFERENCE TO RELATED APPLICATIONS

This application is a divisional application of U.S. patent application Ser. No. 13/225,148, which was filed on Sep. 2, 2011, and issued as U.S. Pat. No. 9,139,643 on Sep. 22, 2015, which application is a divisional application of U.S. patent application Ser. No. 11/693,375, which was filed on Mar. 29, 2007, and issued as U.S. Pat. No. 8,012,936 on Sep. 6, 2011, and which claims the benefit of U.S. Provisional Patent Application Ser. No. 60/787,051, which was filed Mar. 29, 2006 and is now expired, each of which applications is hereby incorporated by reference herein in its entirety.

STATEMENT REGARDING FEDERALLY SPONSORED RESEARCH OR DEVELOPMENT

The subject matter of this application was made with support from the United States Government under NIH/NIA, Grant No. AG20197. The U.S. Government may have certain rights.

REFERENCE TO SEQUENCE LISTING

This application includes one or more Sequence Listings pursuant to 37 C.F.R. 1.821 et seq., which are disclosed in both paper and computer-readable media in the files of U.S. patent application Ser. No. 13/225,148, and which paper and computer-readable disclosures are herein incorporated by reference in their entireties.

FIELD OF THE INVENTION

The present invention is directed to a method of preventing and treating Alzheimer's disease and inhibiting accumulation of tau neurofibrillary tangles in a subject.

BACKGROUND OF THE INVENTION

An emerging treatment for Alzheimer's disease (AD) is immunotherapy to clear amyloid-β (Aβ). Another important target in AD and frontotemporal dementia is the neurofibrillary tangles and/or their pathological tau protein conformers, whose presence correlates well with the degree of dementia (Terry, R., "Neuropathological Changes in Alzheimer Disease," *Prog. Brain Res.* 101:383-390 (1994); Goedert, M., "Tau Protein and Neurodegeneration," *Semin. Cell Dev. Biol.* 15:45-49 (2004)). The objective of immunotherapy for tau pathology is that anti-tau antibodies can clear tau aggregates that may affect neuronal viability. Tau is a soluble protein that promotes tubulin assembly, microtubule stability, and cytoskeletal integrity. Although tau pathology is likely to occur following Aβ aggregation based on Down syndrome studies, analyses of AD brains and mouse models indicate that these pathologies are likely to be synergistic (Sigurdsson, et al., "Local and Distant Histopathological Effects of Unilateral Amyloid-beta 25-35 Injections into the Amygdala of Young F344 Rats," *Neurobiol Aging* 17:893-901 (1996); Sigurdsson, et al., "Bilateral Injections of Amyloid-β 25-35 into the Amygdala of Young Fischer Rats: Behavioral, Neurochemical, and Time Dependent Histopathological Effects," *Neurobiol Aging* 18:591-608 (1997); Lewis, et al., "Neurofibrillary Tangles, Amyotrophy and Progressive Motor Disturbance in Mice Expressing Mutant (P301L) Tau Protein," *Nat Genet.* 25:402-405 (2000); Gotz, et al., "Formation of Neurofibrillary Tangles in P301L Tau Transgenic Mice Induced by A-beta 42 Fibrils," *Science* 293:1491-1495 (2001); Delacourte, et al., "Nonoverlapping but Synergetic Tau and APP Pathologies in Sporadic Alzheimer's Disease," *Neurology.* 59:398-407 (2002); Oddo, et al., "Abeta Immunotherapy Leads to Clearance of Early, But Not Late, Hyperphosphorylated Tau Aggregates via the Proteasome," *Neuron* 43:321-332 (2004); Ribe, et al., "Accelerated Amyloid Deposition, Neurofibrillary Degeneration and Neuronal Loss in Double Mutant APP/Tau Transgenic Mice," *Neurobiol Dis.* (2005)). Hence, targeting both pathologies may substantially increase treatment efficacy. To date, no tau mutations have been observed in AD, however, in frontotemporal dementia, mutations in the tau protein on chromosome 17 (FTDP-17) are a causative factor in the disease, which further supports tau-based therapeutic approaches (Poorkaj, et al., "Tau is a Candidate Gene for Chromosome 17 Frontotemporal Dementia," *Ann Neurol.* 43:815-825 (1998); Spillantini, et al., "Frontotemporal Dementia and Parkinsonism Linked to Chromosome 17: A New Group of Tauopathies," *Brain Pathol.* 8:387-402 (1998)). Transgenic mice expressing these mutations have modeled many aspects of the disease and are valuable tools to study the pathogenesis of tangle-related neurodegeneration and to assess potential therapies. One of these models, the P301L mouse model (Lewis, et al., "Neurofibrillary Tangles, Amyotrophy and Progressive Motor Disturbance in Mice Expressing Mutant (P301L) Tau Protein," *Nat Genet.* 25:402-405 (2000)), recapitulates many of the features of frontotemporal dementia although the CNS distribution of the tau aggregates results primarily in sensorimotor abnormalities which complicates cognitive assessment. Homozygous lines of this mouse model have an early onset of CNS pathology and associated functional impairments which make them ideal for the initial assessment of the feasibility of immunotherapy, targeting pathological tau conformers.

Other tau-related therapeutic approaches include: (1) drugs that inhibit the kinases or activate the phosphatases that affect the state of tau phosphorylation (Iqbal, et al., "Inhibition of Neurofibrillary Degeneration: A Promising Approach to Alzheimer's Disease and Other Tauopathies," *Curr Drug Targets* 5:495-502 (2004); Noble, et al., Inhibition of Glycogen Synthase Kinase-3 by Lithium Correlates with Reduced Tauopathy and Degeneration In Vivo," *Proc Natl Acad Sci USA* 102:6990-6995 (2005)); (2) microtubule stabilizing drugs (Michaelis, et al., {beta}-Amyloid-Induced Neurodegeneration and Protection by Structurally Diverse Microtubule-Stabilizing Agents," *J Pharmacol Exp Ther.* 312:659-668 (2005); Zhang, et al., "Microtubule-Binding Drugs Offset Tau Sequestration by Stabilizing Microtubules and Reversing Fast Axonal Transport Deficits in a Tauopathy Model," *Proc Natl Acad Sci USA* 102:227-231 (2005)); (3) compounds that interfere with tau aggregation (Pickhardt, et al., "Anthraquinones Inhibit Tau Aggregation and Dissolve Alzheimer's Paired Helical Filaments In Vitro and in Cells," *J Biol Chem.* 280:3628-3635 (2005)); and (4) drugs that promote heat shock protein mediated clearance of tau (Dickey, et al., "Development of a High Throughput Drug Screening Assay for the Detection of Changes in Tau Levels—Proof of Concept with HSP90 Inhibitors," *Curr Alzheimer Res.* 2:231-238 (2005)). While all these approaches are certainly worth pursuing, target specificity and toxicity are of a concern, which emphasizes the importance of concurrently developing other types of tau-targeting treatments, such as immunotherapy.

The present invention is directed to overcoming these and other deficiencies in the art.

SUMMARY OF THE INVENTION

One aspect of the present invention includes a method of preventing or treating Alzheimer's Disease or other tauopathies in a subject. The method includes administering a tau protein, its immunogenic epitopes, or antibodies recognizing the tau protein or its immunogenic epitopes under conditions effective to prevent or treat Alzheimer's Disease or other tauopathies.

Another aspect of the present invention includes a method of promoting clearance of aggregates from the brain of a subject. This method includes administering a tau protein, its immunogenic epitopes, or antibodies recognizing the tau protein or its immunogenic epitopes under conditions effective to promote clearance of aggregates from the brain of a subject.

A third aspect of the present invention includes a method of slowing progression of a tangle-related behavioral phenotype in a subject. This method includes administering a tau protein, its immunogenic epitopes, or antibodies recognizing the tau protein or its immunogenic epitopes under conditions effective to slow a tangle-related behavioral phenotype in a subject.

A fourth aspect of the present invention includes a peptide comprising an immunogenic epitope of a tau protein. The amino acid sequence of the peptide can be any one of SEQ ID NOs: 1-20. The immunogenic epitope is effective in preventing and treating Alzheimer's Disease or other tauopathies in a subject, promoting the clearance of aggregates from the brain of a subject, and slowing the progression of a tangle-related behavioral phenotype in a subject.

It is hypothesized that clearance of extracellular tangles may reduce associated pathology, and numerous reports of neuronal uptake of antibodies suggest that intracellular tangles and pre-tangles may also be affected (Fabian, et al., "Intraneuronal IgG in the Central Nervous System," *J Neurol Sci.* 73:257-267 (1986); Fabian, et al., "Intraneuronal IgG in the Central Nervous System: Uptake by Retrograde Axonal Transport," *Neurology* 37:1780-1784 (1987); Liu, et al., "Immunohistochemical Localization of Intracellular Plasma Proteins in the Human Central Nervous System," *Acta Neuropathol* (*Berl*) 78:16-21 (1989); Dietzschold, et al., "Delineation of Putative Mechanisms Involved in Antibody-Mediated Clearance of Rabies Virus from the Central Nervous System," *Proc Natl Acad Sci USA* 89:7252-7256 (1992) (published erratum appears in *Proc Natl Acad Sci USA* 89(19):9365 (1992)); Aihara, et al., "Immunocytochemical Localization of Immunoglobulins in the Rat Brain: Relationship to the Blood-Brain Barrier," *J Comp Neurol.* 342:481-496 (1994); Mohamed, et al., "Immunoglobulin Fc Gamma Receptor Promotes Immunoglobulin Uptake, Immunoglobulin-Mediated Calcium Increase, and Neurotransmitter Release in Motor Neurons," *J Neurosci Res.* 69:110-116 (2002), which are hereby incorporated by reference in their entirety). In the present invention, the effectiveness of active immunization directed against phosphorylated tau conformers in the CNS was determined. Towards this end, homozygous P301L mice were immunized with a phosphorylated tau epitope with subsequent analysis of tau pathology and associated functional impairments. While these studies were underway, the feasibility of this approach was strengthened by findings, indicating that vaccination with recombinant α-synuclein in transgenic mice reduces intraneuronal α-synuclein aggregates (Masliah, et al., "Effects of Alpha-Synuclein Immunization in a Mouse Model of Parkinson's Disease," *Neuron* 46:857-868 (2005), which is hereby incorporated by reference in its entirety)

BRIEF DESCRIPTION OF THE DRAWINGS

FIG. 1A shows that the tau derivative does not form fibrils compared to Aβ1-42 that is very fibrillogenic as depicted by a Thioflavin T assay. FIG. 1B shows the generation of IgG antibodies (1:200 plasma dilution) against the immunogen at various time points (T0, T1, T2, T3=0, 6, 10, and 14 weeks) as determined by phos-tau peptide ELISA assay. Control mice had low levels of autoantibodies that recognized the immunogen and those increased with age. FIG. 1C shows that autoantibodies which recognize both P301L and wild-type human tau were observed both in controls and immunized mice but the levels did not differ significantly between the groups.

FIGS. 2A-E show that the vaccine reduces tau aggregates in the brains of P301L tangle mice at 5 months of age. In FIG. 2A, quantitative analysis of MC1 immunoreactivity within the granular layer of the dentate gyrus revealed a 74% reduction (**p<0.01) in immunized mice compared to control Tg mice that received adjuvant alone. Likewise, in FIG. 2B, PHF1 immunoreactivity within the granular layer of the dentate gyrus was reduced by 52% (*p<0.05) in immunized mice compared to controls. In FIG. 2C, further confirmation of a therapeutic effect was obtained by analysis of the motor cortex, in which MC1 neuronal staining was reduced by 96% (*p<0.0001) compared to control Tg mice. Likewise, in FIG. 2D, in the brainstem, MC1 neuronal staining was reduced by 93% (p=0.01) compared to control Tg mice. FIG. 2E shows the densitometric analysis of PHF1 blots. This analysis revealed a strong trend for reduction in insoluble tau (28% reduction, p=0.09) and a significant increase in soluble tau (77% increase, p=0.01) in the immunized mice compared to control Tg mice, relative to total tau levels. Further analysis of the ratio of soluble tau to insoluble tau indicated a significant increase in the immunized group on PHF1 blots (89% increase, p=0.01), suggesting a mobilization of tau from its insoluble form to soluble form in these treated animals. The right panel of FIG. 2E shows representative blots from control- and Phostau immunized mice. The PHF1 antibody recognizes phosphorylated serines 396 and 404 located within the microtubule-binding repeat on the C-terminal of paired helical fragment (PHF) tau protein. An antibody against total tau (3G6) was used as a control. The same amount of protein was loaded in each lane. Mean values are presented with standard error of the mean.

FIGS. 3A and 3B show MC1-stained coronal sections through the dentate gyrus in control (FIG. 3A) vs. immunized (FIG. 3B) Tg mouse (original magnification: 200×). FIGS. 3C and 3D show PHF1-stained coronal sections through the dentate gyrus in a control (FIG. 3C) vs. immunized (FIG. 3D) Tg mouse (original magnification: 200×). FIGS. 3E and 3F show MC1-stained coronal sections through the motor cortex in a control (FIG. 3E) vs. immunized (FIG. 3F) Tg mouse (original magnification: 100×). FIGS. 3G and 3H show MC1-stained coronal sections through the brain stem below the aqueduct of Sylvius in a control (FIG. 3G) vs. immunized (FIG. 3H) Tg mouse (original magnification: 100×). These magnifications were used for the quantitative analysis (Dentate gyrus: 200×, Motor cortex: 100×, Brain Stem: 100×).

FIG. 4A shows the generation of antibodies (1:200 plasma dilution) against the immunogen at various time points (T0, T1, T2, T3, T4=0, 4, 8, 14, and 26 weeks) as determined by phospho tau peptide ELISA assay. FIG. 4B shows that autoantibodies that recognize both P301L and wild-type human tau were observed in controls and immunized mice, but the levels did not differ significantly between the groups.

FIG. 5A shows the performance of Tg P301L immunized and Tg control mice, trained to remain on a rotarod, and the speed attained during the task. The immunization increased the time the animals were able to stay on the rotarod both at 5 months (trials 1-3, $p<0.02$) and 8 months (trials 4-6, $p<0.05$). FIG. 5B shows the number of foot slips the animals had during the traverse beam task. The immunization greatly reduced the number of foot slips during the performance of the task at 5 months ($p<0.001$) and at 8 months ($p=0.05$). As set forth in FIG. 5C, there was an increase in the maximum velocity (Vmax) attained by the phospho tau immunized Tg animals ($p=0.004$) at 5 months, compared to Tg controls. Vmax did not differ between the groups at 8 months There was no significant difference in the distance traveled, average speed (Vmean) or the resting time at 5 and 8 months. As shown in FIG. 5D, no difference was observed between the groups in the Object Recognition Task that measures short term memory. Both the immunized P301L mice and their transgenic controls spent a comparable time exploring the novel object that differed substantially from the time they spent with the old object. This finding indicates that both groups had normal short term memory at 8 months of age.

As shown in FIG. 6A, quantitative analysis of MC1 immunoreactivity within the granular layer of the dentate gyrus revealed a 47% reduction (*$p<0.05$) in immunized mice compared to control Tg mice that received adjuvant alone. As shown in FIG. 6B, there was a strong trend for a diminished PHF1 immunoreactivity within the granular layer of the dentate gyms (40% reduction; $p<0.12$) in immunized mice compared to controls. FIG. 6C shows that as at 5 months of age (see FIG. 3E-F), MC1 neuronal staining of the motor cortex revealed a more pronounced therapeutic effect (76%, $p=0.02$) than in the dentate gyms. Likewise, as depicted in FIG. 6D, neuronal MC1 staining was substantially reduced in the brain stem of immunized mice compared to controls (78%, $p=0.005$, FIG. 6D). Mean values are presented with standard error of the mean.

In FIG. 7A, the PHF1 antibody reveals the typical staining of tau aggregates/tangles in neuronal cell bodies as previously reported in this model (Lewis, et al., "Neurofibrillary Tangles, Amyotrophy and Progressive Motor Disturbance in Mice Expressing Mutant (P301L) Tau Protein," *Nat Genet.* 25:402-405 (2000), which is hereby incorporated by reference in its entirety). As shown in FIG. 7C, antibodies from mice immunized with the Phos-tau peptide, which contains the PHF epitope, stain primarily neuronal cell bodies within the dentate gyms and the pattern is similar although not identical to the PHF1 staining. A similar staining pattern as in FIGS. 7A and 7C was observed in the motor cortex (FIGS. 7E and 7G) and brain stem (FIGS. 7I and 7K) following immunoreactivity with the PHF1 antibody and the polyclonal antibodies from an immunized mouse, respectively. However, this particular polyclonal antibody stained neurons in the brain stem less intensely than in the dentate gyrus and motor cortex. FIGS. 7B, 7D, 7F, 7H, 7J, and 7L depict adjacent coronal sections to those shown in FIGS. 7A, 7C, 7E, 7G, 7I, and 7K, that were stained with purified antibodies from Tg control mice that received adjuvant alone (control IgG) or pooled mouse IgG [wild-type (Wt) IgG (Sigma)]. Staining with those antibodies resulted in minimal or no staining. Additionally, no immunostaining was observed in wild-type mice with the antibodies purified from immunized mice. These findings indicate that the immunized mice generate antibodies that specifically recognize pathological tau aggregates in the P301L mouse. Staining was performed as detailed infra with PHF1 and purified IgG used at a 1:250 and 10 µg/ml dilution, respectively. Original magnification: 400×.

FIG. 8A shows that PHF staining of the entorhinal cortex from an Alzheimer's brain reveals the typical staining of cell bodies and dystrophic neurites as previously described for this antibody. In FIG. 8B, the polyclonal IgG antibodies derived from an immunized mouse stain neuronal cell bodies in a similar manner as the PHF1 antibody but dystrophic neurites are not prominent. FIG. 5C shows that antibodies purified from a control mouse that received adjuvant alone do not result in appreciable staining. Overall, the staining pattern with these different antibodies is comparable to that observed in the P301L mouse (see FIG. 7).

FIG. 9A shows a coronal brain section stained with an anti-IgG secondary antibody (1:50, Vectastain Elite Kit) through the dentate gyrus of the hippocampus of a Phos-tau immunized P301L mouse. Note the staining of neuronal cell bodies (arrows) and processes (arrows) indicating the presence of IgG. No immunostaining is observed in a non-immunized P301L of a similar age (FIG. 9B) or in a wild-type mouse under these staining conditions. Original magnification: 400×.

In FIGS. 11A-C, a coronal brain section through the pyramidal layer of the hippocampus are shown. Note the FITC-labeled neurons in FIG. 11A that stain with PHF antibody that was applied to the section (FIG. 11B; Texas red tagged secondary antibody). The section was counterstained with DAPI that stains nuclei in blue and double labeled neurons are orange (FIG. 11C). Original magnification: 200×. FIG. 11D-F show a coronal brain section through the nucleus of the brachium inferior colliculus (BIC). Note the FITC-labeled neurons in FIG. 11A that stain with MC1 antibody that was applied to the section (FIG. 11B; Texas red tagged secondary antibody). The section was counterstained with DAPI that stains nuclei in blue and double labeled neurons are orange (FIG. 11C). Original magnification: 200×. For clarification, the labeled neurons in the center of each panel are shown magnified in the inserted boxes.

DETAILED DESCRIPTION OF THE INVENTION

Figure 1A:
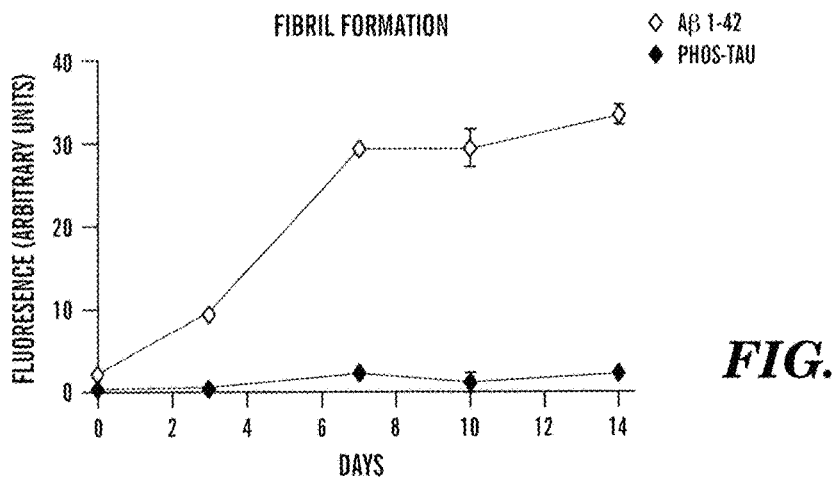
FIGS. 1A-C show that phospho-tau-derivative peptide is not fibrillogenic. It is highly immunogenic in mice treated from 2 to 5 months of age, but autoantibodies against tau are detected. Homozygous transgenic (Tg) P301L mice were immunized from 2 months of age with a phosphorylated tau peptide (Phos-tau=Tau379-408 [P-Ser$_{396,404}$]; n=12). Control Tg P301L animals received aluminum adjuvant alone (n=13). Plasma samples from the animals were analyzed by ELISA, and the brains were analyzed biochemically and immunohistochemically at 5 months of age.

One aspect of the present invention includes a method of treating or preventing Alzheimer's Disease or other tauopathies in a subject. This method includes administering a tau protein, its immunogenic epitopes, or antibodies recognizing the tau protein or its immunogenic epitopes under conditions effective to treat or prevent Alzheimer's Disease or other tauopathies.

Another aspect of the present invention includes a method of promoting clearance of aggregates from the brain of a subject. This method includes administering a tau protein, its immunogenic epitopes, or antibodies recognizing the tau protein or its immunogenic epitopes under conditions effective to promote clearance of aggregates from the brain of a subject. The aggregates to be cleared include neurofibrillary tangles or their pathological tau precursors. Neurofibrillary tangles are often associated with neurodegenerative diseases including, for example, Alzheimer's disease, hereditary frontotemporal dementia and parkinsonism linked to chromosome 17 (FTDP-17), Pick's disease, sporadic corticobasal degeneration, and progressive supranuclear palsy.

Another aspect of the present invention includes a method of slowing the progression of a tangle-related behavioral phenotype in a subject. This method includes administering a tau protein, its immunogenic epitopes, or antibodies recognizing the tau protein or its immunogenic epitopes under conditions effective to slow a tangle-related behavioral phenotype in a subject.

The tau protein or immunogenic fragment described above can include any one of the six isoforms of the human tau protein or a segment thereof. Tau has 0, 1, or 2 N-terminal inserts resulting from the splicing of exons two and three, and either 3 or 4 microtubule-binding domains resulting from the splicing of exon ten. The amino acid sequences corresponding to the isoforms of the human tau protein of the present invention are given in SEQ ID NOs:21-26 below.

SEQ ID NO:21, the longest tau isoform (441a.a), containing two N-terminal inserts and four microtubule binding (2N4R) domains is as follows:

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
                100                 105                 110

Ser Leu Glu Asp Glu Ala Ala Gly His Val Thr Gln Ala Arg Met Val
            115                 120                 125

Ser Lys Ser Lys Asp Gly Thr Gly Ser Asp Asp Lys Lys Ala Lys Gly
        130                 135                 140

Ala Asp Gly Lys Thr Lys Ile Ala Thr Pro Arg Gly Ala Ala Pro Pro
145                 150                 155                 160
```

-continued

```
Gly Gln Lys Gly Gln Ala Asn Ala Thr Arg Ile Pro Ala Lys Thr Pro
                165                 170                 175
Pro Ala Pro Lys Thr Pro Ser Ser Gly Glu Pro Pro Lys Ser Gly
            180                 185                 190
Asp Arg Ser Gly Tyr Ser Ser Pro Gly Ser Pro Gly Thr Pro Gly Ser
            195                 200                 205
Arg Ser Arg Thr Pro Ser Leu Pro Thr Pro Pro Thr Arg Glu Pro Lys
    210                 215                 220
Lys Val Ala Val Val Arg Thr Pro Pro Lys Ser Pro Ser Ser Ala Lys
225                 230                 235                 240
Ser Arg Leu Gln Thr Ala Pro Val Pro Met Pro Asp Leu Lys Asn Val
                245                 250                 255
Lys Ser Lys Ile Gly Ser Thr Glu Asn Leu Lys His Gln Pro Gly Gly
                260                 265                 270
Gly Lys Val Gln Ile Ile Asn Lys Lys Leu Asp Leu Ser Asn Val Gln
            275                 280                 285
Ser Lys Cys Gly Ser Lys Asp Asn Ile Lys His Val Pro Gly Gly Gly
    290                 295                 300
Ser Val Gln Ile Val Tyr Lys Pro Val Asp Leu Ser Lys Val Thr Ser
305                 310                 315                 320
Lys Cys Gly Ser Leu Gly Asn Ile His His Lys Pro Gly Gly Gly Gln
                325                 330                 335
Val Glu Val Lys Ser Glu Lys Leu Asp Phe Lys Asp Arg Val Gln Ser
                340                 345                 350
Lys Ile Gly Ser Leu Asp Asn Ile Thr His Val Pro Gly Gly Gly Asn
            355                 360                 365
Lys Lys Ile Glu Thr His Lys Leu Thr Phe Arg Glu Asn Ala Lys Ala
    370                 375                 380
Lys Thr Asp His Gly Ala Glu Ile Val Tyr Lys Ser Pro Val Val Ser
385                 390                 395                 400
Gly Asp Thr Ser Pro Arg His Leu Ser Asn Val Ser Ser Thr Gly Ser
                405                 410                 415
Ile Asp Met Val Asp Ser Pro Gln Leu Ala Thr Leu Ala Asp Glu Val
                420                 425                 430
Ser Ala Ser Leu Ala Lys Gln Gly Leu
            435                 440
```

SEQ ID NO:22 contains two N-terminal inserts and three microtubule-binding domains (2N3R) as follows:

```
Met Ala Glu Pro Arg Gln Glu Phe Glu Val Met Glu Asp His Ala Gly
1               5                   10                  15
Thr Tyr Gly Leu Gly Asp Arg Lys Asp Gln Gly Gly Tyr Thr Met His
                20                  25                  30
Gln Asp Gln Glu Gly Asp Thr Asp Ala Gly Leu Lys Glu Ser Pro Leu
            35                  40                  45
Gln Thr Pro Thr Glu Asp Gly Ser Glu Glu Pro Gly Ser Glu Thr Ser
    50                  55                  60
Asp Ala Lys Ser Thr Pro Thr Ala Glu Asp Val Thr Ala Pro Leu Val
65                  70                  75                  80
Asp Glu Gly Ala Pro Gly Lys Gln Ala Ala Ala Gln Pro His Thr Glu
                85                  90                  95
Ile Pro Glu Gly Thr Thr Ala Glu Glu Ala Gly Ile Gly Asp Thr Pro
                100                 105                 110
```

-continued

```
Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Sly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
            195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Her Arg Leu Gln Thr Ala Pro Val Pro Met Pro Asp Leu Lys Asn Val
                245                 250                 255

Lys Ser Lys Ile Gly Her Thr Glu Asn Leu Lys His Gln Pro Gly Gly
            260                 265                 270

Gly Lys Val Gln Ile Val Tyr Lys Pro Val Asp Leu Ser Lys Val Thr
            275                 280                 285

Ser Lys Cys Gly Ser Leu Gly Asn Ile His His Lys Pro Gly Gly Gly
    290                 295                 300

Gln Val Glu Val Lys Ser Glu Lys Leu Asp Phe Lys Asp Arg Val Gln
305                 310                 315                 320

Ser Lys Ile Gly Ser Leu Asp Asn Ile Thr His Val Pro Gly Gly Gly
                325                 330                 335

Asn Lys Lys Ile Glu Thr His Lys Leu Thr Phe Arg Glu Asn Ala Lys
            340                 345                 350

Ala Lys Thr Asp His Gly Ala Glu Ile Val Tyr Lys Ser Pro Val Val
            355                 360                 365

Ser Gly Asp Thr Ser Pro Arg His Leu Ser Asn Val Ser Ser Thr Gly
    370                 375                 380

Ser Ile Asp Met Val Asp Ser Pro Gln Leu Ala Thr Leu Ala Asp Glu
385                 390                 395                 400

Val Ser Ala Ser Leu Ala Lys Gln Gly Leu
                405                 410
```

SEQ ID NO:23 contains one N-terminal insert and four microtubule-binding domains (1N4R) as follows:

```
Met Ala Glu Pro Arg Gln Glu Phe Glu Val Met Glu Asp His Ala Gly
1                5                  10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Ala Glu Glu Ala Gly Ile Gly
65                  70                  75                  80

Asp Thr Pro Ser Leu Glu Asp Glu Ala Ala Gly His Val Thr Gln Ala
                85                  90                  95
```

-continued

```
Arg Met Val Ser Lys Ser Lys Asp Gly Thr Gly Ser Asp Asp Lys Lys
                100                 105                 110

Ala Lys Gly Ala Asp Gly Lys Thr Lys Ile Ala Thr Pro Arg Gly Ala
            115                 120                 125

Ala Pro Pro Gly Gln Lys Gly Gln Ala Asn Ala Thr Arg Ile Pro Ala
        130                 135                 140

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
        195                 200                 205

Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240

Pro Gly Gly Gly Lys Val Gln Ile Ile Asn Lys Lys Leu Asp Leu Ser
                245                 250                 255

Asn Val Gln Ser Lys Cys Gly Ser Lys Asp Asn Ile Lys His Val Pro
            260                 265                 270

Gly Gly Gly Ser Val Gln Ile Val Tyr Lys Pro Val Asp Leu Ser Lys
        275                 280                 285

Val Thr Ser Lys Cys Gly Ser Leu Gly Asn Ile His His Lys Pro Gly
    290                 295                 300

Gly Gly Gln Val Glu Val Lys Ser Glu Lys Leu Asp Phe Lys Asp Arg
305                 310                 315                 320

Val Gln Ser Lys Ile Gly Ser Leu Asp Asn Ile Thr His Val Pro Gly
                325                 330                 335

Gly Gly Asn Lys Lys Ile Glu Thr His Lys Leu Thr Phe Arg Glu Asn
            340                 345                 350

Ala Lys Ala Lys Thr Asp His Gly Ala Glu Ile Val Tyr Lys Ser Pro
        355                 360                 365

Val Val Ser Gly Asp Thr Ser Pro Arg His Leu Ser Asn Val Ser Ser
    370                 375                 380

Thr Gly Ser Ile Asp Met Val Asp Ser Pro Gln Leu Ala Thr Leu Ala
385                 390                 395                 400

Asp Glu Val Ser Ala Ser Leu Ala Lys Gln Gly Leu
                405                 410
```

SEQ ID NO:24 contains zero N-terminal inserts and four microtubule-binding domains (0N4R) as follows:

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80
```

```
Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Ala Pro Lys Thr Pro Pro Ser Ser Gly
            115                 120                 125

Glu Pro Pro Lys Ser Gly Asp Arg Ser Gly Tyr Ser Ser Pro Gly Ser
        130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Ile Asn Lys Lys Leu
    210                 215                 220

Asp Leu Ser Asn Val Gln Ser Lys Cys Gly Ser Lys Asp Asn Ile Lys
225                 230                 235                 240

His Val Pro Gly Gly Gly Ser Val Gln Ile Val Tyr Lys Pro Val Asp
                245                 250                 255

Leu Ser Lys Val Thr Ser Lys Cys Gly Ser Leu Gly Asn Ile His His
            260                 265                 270

Lys Pro Gly Gly Gly Gln Val Glu Val Lys Ser Glu Lys Leu Asp Phe
        275                 280                 285

Lys Asp Arg Val Gln Ser Lys Ile Gly Ser Leu Asp Asn Ile Thr His
    290                 295                 300

Val Pro Gly Gly Gly Asn Lys Lys Ile Glu Thr His Lys Leu Thr Phe
305                 310                 315                 320

Arg Glu Asn Ala Lys Ala Lys Thr Asp His Gly Ala Glu Ile Val Tyr
                325                 330                 335

Lys Ser Pro Val Val Ser Gly Asp Thr Ser Pro Arg His Leu Ser Asn
            340                 345                 350

Val Ser Ser Thr Gly Ser Ile Asp Met Val Asp Ser Pro Gln Leu Ala
        355                 360                 365

Thr Leu Ala Asp Glu Val Ser Ala Ser Leu Ala Lys Gln Gly Leu
    370                 375                 380
```

SEQ ID NO:25 contains one N-terminal insert and three microtubule-binding domains (1N3R) as follows:

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Ala Glu Glu Ala Gly Ile Gly
65                  70                  75                  80

Asp Thr Pro Ser Leu Glu Asp Glu Ala Ala Gly His Val Thr Gln Ala
                85                  90                  95
```

-continued

```
Arg Met Val Ser Lys Ser Lys Asp Gly Thr Gly Ser Asp Lys Lys
            100                 105                 110

Ala Lys Gly Ala Asp Gly Lys Thr Lys Ile Ala Thr Pro Arg Gly Ala
            115                 120                 125

Ala Pro Pro Gly Gln Lys Gly Gln Ala Asn Ala Thr Arg Ile Pro Ala
            130                 135                 140

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
            195                 200                 205

Ser Ala Lys Ser Arg Leu Gln Thr Ala Pro Val Pro Met Pro Asp Leu
            210                 215                 220

Lys Asn Val Lys Ser Lys Ile Gly Ser Thr Glu Asn Leu Lys His Gln
225                 230                 235                 240

Pro Gly Gly Gly Lys Val Gln Ile Val Tyr Lys Pro Val Asp Leu Ser
            245                 250                 255

Lys Val Thr Ser Lys Cys Gly Ser Leu Gly Asn Ile His His Lys Pro
            260                 265                 270

Gly Gly Gly Gln Val Glu Val Lys Ser Glu Lys Leu Asp Phe Lys Asp
            275                 280                 285

Arg Val Gln Ser Lys Ile Gly Ser Leu Asp Asn Ile Thr His Val Pro
            290                 295                 300

Gly Gly Gly Asn Lys Lys Ile Glu Thr His Lys Leu Thr Phe Arg Glu
305                 310                 315                 320

Asn Ala Lys Ala Lys Thr Asp His Gly Ala Glu Ile Val Tyr Lys Ser
                325                 330                 335

Pro Val Val Ser Gly Asp Thr Ser Pro Arg His Leu Ser Asn Val Ser
            340                 345                 350

Ser Thr Gly Ser Ile Asp Met Val Asp Ser Pro Gln Leu Ala Thr Leu
            360                 365

Ala Asp Glu Val Ser Ala Ser Leu Ala Lys Gln Gly Leu
            370                 375                 380
```

SEQ ID NO:26 contains zero N-terminal inserts and three microtubule-binding domains (0N3R) as follows:

```
His Met Ala Met Ala Glu Pro Arg Gln Glu Phe Glu Val Met Glu Asp
1               5                   10                  15

His Ala Gly Thr Tyr Gly Leu Gly Asp Arg Lys Asp Gln Gly Gly Tyr
            20                  25                  30

Thr Met His Gln Asp Gln Glu Gly Asp Thr Asp Ala Gly Leu Lys Ala
            35                  40                  45

Glu Glu Ala Gly Ile Gly Asp Thr Pro Ser Leu Glu Asp Glu Ala Ala
        50                  55                  60

Gly His Val Thr Gln Ala Arg Met Val Ser Lys Ser Lys Asp Gly Thr
65                  70                  75                  80

Gly Ser Asp Asp Lys Lys Ala Lys Gly Ala Asp Gly Lys Thr Lys Ile
                85                  90                  95

Ala Thr Pro Arg Gly Ala Ala Pro Pro Gly Gln Lys Gly Gln Ala Asn
            100                 105                 110
```

```
Ala Thr Arg Ile Pro Ala Lys Thr Pro Pro Ala Pro Lys Thr Pro Pro
        115                 120                 125

Ser Ser Gly Glu Pro Pro Lys Ser Gly Asp Arg Ser Gly Tyr Ser Ser
    130                 135                 140

Pro Gly Ser Pro Gly Thr Pro Gly Ser Arg Ser Arg Thr Pro Ser Leu
145                 150                 155                 160

Pro Thr Pro Pro Thr Arg Glu Pro Lys Lys Val Ala Val Val Arg Thr
                165                 170                 175

Pro Pro Lys Ser Pro Ser Ser Ala Lys Ser Arg Leu Gln Thr Ala Pro
            185                 185                 190

Val Pro Met Pro Asp Leu Lys Asn Val Lys Ser Lys Ile Gly Ser Thr
        195                 200                 205

Glu Asn Leu Lys His Gln Pro Gly Gly Gly Lys Val Gln Ile Val Tyr
    210                 215                 220

Lys Pro Val Asp Leu Ser Lys Val Thr Ser Lys Cys Gly Ser Leu Gly
225                 230                 235                 240

Asn Ile His His Lys Pro Gly Gly Gly Gln Val Glu Val Lys Ser Glu
            245                 250                 255

Lys Leu Asp Phe Lys Asp Arg Val Gln Ser Lys Ile Gly Ser Leu Asp
            260                 265                 270

Asn Ile Thr His Val Pro Gly Gly Gly Asn Lys Lys Ile Glu Thr His
            275                 280                 285

Lys Leu Thr Phe Arg Glu Asn Ala Lys Ala Lys Thr Asp His Gly Ala
    290                 295                 300

Glu Ile Val Tyr Lys Ser Pro Val Val Ser Gly Asp Thr Ser Pro Arg
305                 310                 315                 320

His Leu Ser Asn Val Ser Ser Thr Gly Ser Ile Asp Met Val Asp Ser
            325                 330                 335

Pro Gln Leu Ala Thr Leu Ala Asp Glu Val Ser Ala Ser Leu Ala Lys
            340                 345                 350

Gln Gly Leu
    355
```

The tau protein of the present invention can be phosphorylated at one or more amino acid residues. In a preferred embodiment, the tau protein is fully phosphorylated. Amino acid residues in the full length tau protein, SEQ ID NO:21, that are phosphorylated include tyrosines at amino acid positions 18, 29, 197, 310, and 394; serines at amino acid positions 184, 185, 198, 199, 202, 208, 214, 235, 237, 238, 262, 293, 324, 356, 396, 400, 404, 409, 412, 413, and 422; and threonines at amino acids positions 175, 181, 205, 212, 217, 231, and 403. Phosphorylated amino acid residues in SEQ ID NO:22 include tyrosines at positions 18, 29, 197, 279, and 363; serines at positions 184, 185, 198, 199, 202, 208, 214, 235, 237, 238, 262, 293, 325, 365, 369, 373, 378, 381, 382, 391; and threonine at positions 175, 181, 205, 212, 217, 231, 372. Phosphorylated amino acid residues in SEQ ID NO:23 include tyrosines at positions 18, 29, 168, 281, and 365; serines at positions 155, 156, 169, 170, 173, 179, 185, 206, 208, 209, 233, 264, 295, 327, 367, 371, 375, 380, 383, 384, 393; and threonines at positions 146, 152, 176, 183, 188, 202, and 374. Phosphorylated amino acids in SEQ ID NO:24 include tyrosines at positions 18, 29, 139, 252, 336; serines at positions 126, 127, 140, 141, 144, 150, 156, 177, 179, 180, 204, 234, 235, 266, 298, 338, 342, 346, 351, 354, 355, 364, and threonines at positions 117, 123, 147, 154, 159, 173, and 345. Phosphorylated amino acid residues in SEQ ID NO: 25 include tyrosines at positions 18, 29, 168, 250, 334; serines at positions 155, 156, 169, 170, 173, 179, 185, 206, 208, 209, 233, 264, 296, 336, 340, 344, 349, 352, 353, 362; and threonines at positions 146, 152, 176, 183, 188, 202, 343. Phosphorylated amino acid residues in SEQ ID NO: 26 include tyrosines at positions 18, 29, 139, 221, and 305; serines at positions 126, 127, 140, 141, 144, 150, 156, 177, 179, 180, 204, 235, 267, 307, 311, 315, 320, 323, 324, 333; and threonine at positions 117, 123, 147, 154, 159, 173, and 314. Additional tyrosine, serine or threonine amino acids within the tau sequences may also be phosphorylated.

Unless otherwise indicated, reference to tau includes the natural human amino acid sequences (SEQ ID NO:21-26). Variants of such segments, analogs, and mimetics of the natural tau peptide that induce and/or crossreact with antibodies to the preferred epitopes of tau protein can also be used. Analogs, including allelic, species, and induced variants, typically differ from naturally occurring peptides at one, two, or a few positions, often by virtue of conservative substitutions. Analogs typically exhibit at least 80 or 90% sequence identity with natural peptides. Some analogs also include unnatural amino acids or modifications of N or C terminal amino acids at one, two, or a few positions.

In addition to wildtype or natural tau proteins, the use of tau proteins containing one or more amino acid substitutions are also contemplated. In a preferred embodiment of the present invention, the tau protein contains a proline to leucine mutation at amino acid position 301 (P301L) of SEQ ID NO:21. Other amino acid mutations of the tau protein are also contemplated. These mutations include a lysine to threonine mutation at amino acid residue 257 (K257T) in SEQ ID NO: 21; an isoleucine to valine mutation at amino acid position 260 (I260V) of SEQ ID NO:21; a glycine to valine mutation at amino acid position 272 (G272V) of SEQ ID NO:21; an asparagine to lysine mutation at amino acid position 279 (N279K) of SEQ ID NO:21; an asparagine to histidine mutation at amino acid position 296 (N296H) of SEQ ID NO:21; a proline to serine mutation at amino acid position 301 (P301S) of SEQ ID NO:21; a glycine to valine mutation at amino acid position 303 (G303V) of SEQ ID NO:21; a serine to asparagine mutation at position 305 (S305N) of SEQ ID NO:21; a glycine to serine mutation at amino acid position 335 (G335S) of SEQ ID NO:21; a valine to methionine mutation at position 337 (V337M) of SEQ ID NO:21; a glutamic acid to valine mutation at position 342 (E342V) of SEQ ID NO:21; a lysine to isoleucine mutation at amino acid position 369 (K369I) of SEQ ID NO:21; a glycine to arginine mutation at amino acid position 389 (G389R) of SEQ ID NO:21; and an arginine to tryptophan mutation at amino acid position 406 (R406W) of SEQ ID NO:21. In a preferred embodiment of the present invention, the tau mutant protein or peptide fragment is phosphorylated.

Immunogenic fragments of the tau protein useful for the present invention can be identified based on sequence antigenicity, hydrophilicity, and accessibility. In a preferred embodiment, the tau protein or its immunogenic epitopes may be phosphorylated at one or more amino acids. One preferred immunogenic epitope of the tau protein of this invention is Tau379-408 containing phosphorylated serine residues at positions 396 and 404. The sequence for Tau 379-408 [P-Ser$_{396,404}$] (SEQ ID NO:2) is shown in Table 1 as follows:

| SEQ ID NO: | NAME | SEQUENCE |
|---|---|---|
| SEQ ID NO: 1 | Tau 133-162 | DGTGSDDKKAKGADGKTKIATPRGAAPPGQ-NH$_2$ |
| SEQ ID NO: 2 | Tau 379-408 [P-Ser$_{396,404}$] | RENAKAKTDHGAEIVYKSPVVSGDTSPRHL-NH$_2$ |
| SEQ ID NO: 3 | Tau 192-221 [P-Ser$_{119,202,214}$,-Thr$_{205,212}$] | GDRSGYSSPGSPGTPGSRSRTPSLPTPPTR-NH$_2$ |
| SEQ ID NO: 4 | Tau221-250 [P-Thr$_{231}$,-Ser$_{235}$] | REPKKVAVVRTPPKSPSSAKSRLQTAPVPM-NH$_2$ |
| SEQ ID NO: 5 | Tau184-213 | SSGEPPKSGDRSQYSSPGSPGTPGSRSRT-NH$_2$ |
| SEQ ID NO: 6 | Tau1-30 | MAEPRQEFEVMEDHAGTYGLGDRKDQGGYT-NH$_2$ |
| SEQ ID NO: 7 | Tau30-60 | TMHQDQEGDTDAGLKESPLQTPTEDGSEEPG-NH$_2$ |
| SEQ ID NO: 8 | Tau60-90 | GSETSDAKSTPTAEDVTAPLVDEGAPGKQAA-NH$_2$ |
| SEQ ID NO: 9 | Tau90-120 | AAQPHTEIPEGTTAEEAGIGDTPSLEDEAAG-NH$_2$ |
| SEQ ID NO: 10 | Tau120-150 | GHVTQARMVSKSKDGTGSDDKKAKGADGKTK-NH$_2$ |
| SEQ ID NO: 11 | Tau150-180 | KIATPRGAAPPGQKGQANATRIPAKTPPAPK-NH$_2$ |
| SEQ ID NO: 12 | Tau180-210 | KTPPSSGEPPKSGDRSGYSPGSPGTPGSRS-NH$_2$ |
| SEQ ID NO: 13 | Tau210-240 | SRTPSLPTPPTREPKKVAVVRTPPKSPSSAK-NH$_2$ |
| SEQ ID NO: 14 | Tau240-270 | KSRLQTAPVPMPDLKNVKSKIGSTENLKHQP-NH$_2$ |
| SEQ ID NO: 15 | Tau270-300 | PGGGKVQIINKKLDLSNVQSKCGSKDNIKHV-NH$_2$ |
| SEQ ID NO: 16 | Tau300-330 | VPGGGSVQIVYKPVDLSKVTSKCGSLGNIHH-NH$_2$ |
| SEQ ID NO: 17 | Tau330-360 | HKPGGGQVEVKSEKLDFKDRVQSKIGSLDNI-NH$_2$ |
| SEQ ID NO: 18 | Tau360-390 | ITHVPGGGNKKIETHKLTFRENAKAKTDHGA-NH$_2$ |
| SEQ ID NO: 19 | Tau390-420 | AEIVYKSPVVSGDTSPRHLSNVSSTGSIDMV-NH$_2$ |
| SEQ ID NO: 20 | Tau411-441 | VSSTGSIDMVDSPQLATLADEVSASLAKQGL-NH$_2$ |

Additional immunogenic fragments of the present invention include any one SEQ ID NOs: 1 or 3-20 as shown in Table 1. The names of the peptides in Table 1 correspond to the amino acid position of these peptides in the longest isoform of tau, SEQ ID NO:21. Many of these sequences contain well established phospho-tau epitopes previously observed in AD and transgenic mouse models. Phosphorylated amino acid residues within each sequence in Table 1 are indicated in bold and shading. The C-terminus of each of SEQ ID NOs:1-20 above is preferably amidated as shown to preserve the immunogenicity of that region of the peptide.

In a preferred embodiment of the present invention, the tau peptides of the present invention can contain one or more D-amino acid residues. The amino acids being in D-form would have the effect of enhancing the stability of the peptide. These D-amino acids can be in the same order as the L-form of the peptide or assembled in a reverse order from the L-form sequence to maintain the overall topology of the native sequence (Ben-Yedidia et al., "A Retro-Inverso Peptide Analogue of Influenza Virus Hemagglutinin B-cell Epitope 91-108 Induces a Strong Mucosal and Systemic Immune Response and Confers Protection in Mice after Intranasal Immunization," *Mol Immunol*. 39:323 (2002); Guichard, et al., "Antigenic Mimicry of Natural L-peptides with Retro-Inverso-Peptidomimetics," *PNAS* 91:9765-9769 (1994); Benkirane, et al., "Antigenicity and Immunogenicity of Modified Synthetic Peptides Containing D-Amino Acid Residues," *J. Bio. Chem*. 268(35):26279-26285 (1993), which are hereby incorporated by reference in their entirety).

Therapeutic agents can be longer polypeptides that include, for example, an active fragment of tau peptide, together with other amino acids. For example, preferred agents include fusion proteins comprising a segment of tau linked to a promiscuous T-helper cell epitope which thereby promotes a B-cell response against the tau segment.

Other portions of the tau protein that are suitable for practicing the present invention include recombinant forms of the protein and fragments of the protein involved in the formation of paired helical filament (PHF). For example, PHF generated from tau, purified PHF from human AD brains or purified PHF-like protein from P301L mice are additional immunogenic peptides contemplated for use when practicing the present invention.

Immunogenic fragments that have a low β-sheet content and few T-cell epitopes are preferred, however, fragments that contain high β-sheet content or T-cell epitopes can be modified to reduce potential toxicity.

Tau, its fragments, and analogs can be synthesized by solid phase peptide synthesis or recombinant expression, or can be obtained from natural sources. Automatic peptide synthesizers are commercially available from numerous suppliers, such as Applied Biosystems (Foster City, Ca.). Recombinant expression systems can include bacteria, such as *E. coli*, yeast, insect cells, or mammalian cells. Procedures for recombinant expression are described by Sambrook et al., *Molecular Cloning: A Laboratory Manual* (C.S.H.P. Press, NY 2d ed., 1989), which is hereby incorporated by reference in its entirety.

In a variation of the present invention, an immunogenic peptide, such as a fragment of tau, can be presented by a virus or bacteria as part of an immunogenic composition. A nucleic acid encoding the immunogenic peptide is incorporated into a genome or episome of the virus or bacteria. Optionally, the nucleic acid is incorporated in such a manner that the immunogenic peptide is expressed as a secreted protein or as a fusion protein with an outer surface protein of a virus or a transmembrane protein of bacteria so that the peptide is displayed. Viruses or bacteria used in such methods should be nonpathogenic or attenuated. Suitable viruses include adenovirus, HSV, Venezuelan equine encephalitis virus and other alpha viruses, vesicular stomatitis virus, and other rhabdo viruses, vaccinia and fowl pox. Suitable bacteria include Salmonella and Shigella. Fusion of an immunogenic peptide to HBsAg of HBV is particularly suitable.

Immune responses against neurofibrillary tangles can also be induced by administration of nucleic acids encoding segments of tau peptide, and fragments thereof, other peptide immunogens, or antibodies and their component chains used for passive immunization. Such nucleic acids can be DNA or RNA. A nucleic acid segment encoding an immunogen is typically linked to regulatory elements, such as a promoter and enhancer, which allow expression of the DNA segment in the intended target cells of a patient. For expression in blood cells, as is desirable for induction of an immune response, promoter and enhancer elements from light or heavy chain immunoglobulin genes or the CMV major intermediate early promoter and enhancer are suitable to direct expression. The linked regulatory elements and coding sequences are often cloned into a vector. For administration of double-chain antibodies, the two chains can be cloned in the same or separate vectors.

A number of viral vector systems are available including retroviral systems (see, e.g., Lawrie et al., *Cur. Opin. Genet. Develop*. 3:102-109 (1993), which is hereby incorporated by reference in its entirety); adenoviral vectors (Bett et al., *J. Virol*. 67:5911 (1993), which is hereby incorporated by reference in its entirety); adeno-associated virus vectors (Zhou et al., *J. Exp. Med*. 179:1867 (1994), which is hereby incorporated by reference in its entirety), viral vectors from the pox family including vaccinia virus and the avian pox viruses, viral vectors from the alpha virus genus, such as those derived from Sindbis and Semliki Forest Viruses (Dubensky et al., *J. Virol*. 70:508-519 (1996), which is hereby incorporated by reference in its entirety), Venezuelan equine encephalitis virus (see U.S. Pat. No. 5,643,576 to Johnston et al., which is hereby incorporated by reference in its entirety) and rhabdoviruses, such as vesicular stomatitis virus (see WO 96/34625 to Rose, which is hereby incorporated by reference in its entirety) and papillomaviruses (Ohe, et al., *Human Gene Therapy* 6:325-333 (1995); WO 94/12629 to Woo et al.; and Xiao & Brandsma, *Nucleic Acids. Res*. 24:2630-2622 (1996), which are hereby incorporated by reference in their entirety).

DNA encoding an immunogen, or a vector containing the same, can be packaged into liposomes. Suitable lipids and related analogs are described by U.S. Pat. No. 5,208,036 to Eppstein et al., U.S. Pat. No. 5,264,618 to Felgner et al., U.S. Pat. No. 5,279,833 to Rose, and U.S. Pat. No. 5,283,185 to Epand et al., which are hereby incorporated by reference in their entirety. Vectors and DNA encoding an immunogen can also be adsorbed to or associated with particulate carriers, examples of which include polymethyl methacrylate polymers and polylactides and poly(lactide-co-glycolides).

Gene therapy vectors or naked DNA can be delivered in vivo by administration to an individual patient, typically by systemic administration (e.g., intravenous, intraperitoneal, nasal, gastric, intradermal, intramuscular, subdermal, or intracranial infusion) or topical application (see e.g., U.S. Pat. No. 5,399,346 to Anderson et al., which is hereby incorporated by reference in its entirety). Such vectors can further include facilitating agents such as bupivacine (U.S. Pat. No. 5,593,970 to Attardo et al., which is hereby incorporated by reference in its entirety). DNA can also be administered using a gene gun (Xiao & Brandsma, *Nucleic Acids. Res*. 24:2630-2622 (1996), which is hereby incorporated by reference in its entirety). The DNA encoding an immunogen is precipitated onto the surface of microscopic metal beads. The microprojectiles are accelerated with a shock wave or expanding helium gas, and penetrate tissues to a depth of several cell layers. For example, the Accel™ Gene Delivery Device manufactured by Agacetus, Inc. Middleton Wis. is suitable. Alternatively, naked DNA can pass through skin into the blood stream simply by spotting the DNA onto skin with chemical or mechanical irritation (see WO 95/05853 to Carson et al., which is hereby incorporated by reference in its entirety).

In a further variation, vectors encoding immunogens can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Antibodies that specifically bind to any of the six isoforms of the tau protein or fragment thereof, hyperphosphorylated tau, aggregated tau, or any region of the paired helical filaments may be therapeutically effective in the context of the present invention. Preferred antibodies are those which recognize the phosphorylated form of the tau protein isoforms set forth in SEQ ID NOs: 21-26 or the phosphorylated immunogenic fragments set forth in SEQ ID NOs: 1-20. Such antibodies can be monoclonal or polyclonal, full-length, single-chain antibodies, or nanobodies. Antibodies may be non-human, chimeric, or humanized antibodies. Preferred antibodies may bind specifically to the aggregated form of tau without binding to the dissociated form. Alternatively, an antibody may bind specifically to the dissociated form without binding to the aggregated form. An antibody may recognize other forms of tau that accumulates in AD brain and related disorders. These forms differ from the normal tau in terms of post-translational modification, glycation, proteolytic truncation, and racemization. Antibodies used in therapeutic methods usually have an intact constant region or at least a sufficient portion of the constant region to interact with an Fc receptor. Human isotype IgG1 is preferred because of it having the highest affinity of human isotypes for the FcRI receptor on phagocytic cells. Bispecific Fab fragments can also be used, in which one arm of the antibody has specificity for tau, and the other for an Fc receptor. Some antibodies bind to tau with a binding affinity greater than or equal to about $10^6$, $10^7$, $10^8$, $10^9$, or $10^{10}$ $M^{-1}$.

Polyclonal sera typically contain mixed populations of antibodies binding to several epitopes along the length of tau. However, polyclonal sera can be specific to a particular segment of tau, such as tau379-408. Monoclonal antibodies bind to a specific epitope within tau that can be a conformational or nonconformational epitope.

In some methods, multiple monoclonal antibodies having binding specificities to different epitopes are used. Such antibodies can be administered sequentially or simultaneously. Antibodies to neurofibrillary tangle components other than tau can also be used.

Administration of the tau protein, its immunogenic epitope, or an antibody recognizing the protein or epitope can be used as a therapy to treat Alzheimer's disease, or other tauopathy associated with the development of neurofibrillary tangles. Additionally, the administration of the tau protein, its immunogenic epitope or antibody recognizing the protein or epitope can also be used as a prophylactic treatment to prevent the onset of Alzheimer's disease, or other tauopathy associated with the neurofibrillary tangle.

Another aspect of the present invention relates to a pharmaceutical composition containing (one or more of) the immunogenic epitopes of the tau protein. In addition to the immunogenic epitope, the pharmaceutical composition also contains a pharmaceutical carrier and/or a suitable adjuvant as described below.

A further aspect of the invention relates to a phosphorylated tau protein and a pharmaceutical composition containing the phosphorylated tau protein. The phosphorylated tau protein can be the full-length protein, an isoform, fragment, or a recombinant form of the protein. Likewise the phosphorylated tau protein can also contain one or more amino acid mutations. In addition to the phosphorylated tau protein, the pharmaceutical composition also contains a pharmaceutical carrier and/or a suitable adjuvant as described below.

Patients amenable to treatment include individuals at risk of disease but not showing symptoms, as well as patients presently showing symptoms. In the case of Alzheimer's disease, virtually anyone is at risk of suffering from Alzheimer's disease. Therefore, the present methods can be administered prophylactically to the general population without the need for any assessment of the risk of the subject patient. The present methods are especially useful for individuals who do have a known genetic risk of Alzheimer's disease. Such individuals include those having relatives who have experienced this disease, and those whose risk is determined by analysis of genetic or biochemical markers. Genetic markers of risk toward Alzheimer's disease include mutations in the APP gene, particularly mutations at position 717 and positions 670 and 671 referred to as the Hardy and Swedish mutations respectively. Other markers of risk are mutations in the presenilin genes, PS1 and PS2, and ApoE4, family history of AD, hypercholesterolemia or atherosclerosis. Individuals presently suffering from Alzheimers disease can be recognized from characteristic dementia by the presence of risk factors described above. In addition, a number of diagnostic tests are available for identifying individuals who have AD. These include measurement of CSF tau and Aβ42 levels. Elevated tau and decreased Aβ42 levels signify the presence of AD. Individuals suffering from Alzheimer's disease can also be diagnosed by Alzheimer's Disease and Related Disorders Association criteria.

In asymptomatic patients, treatment can begin at any age (e.g., 10, 20, 30). Usually, however, it is not necessary to begin treatment until a patient reaches 40, 50, 60, or 70. Treatment typically entails multiple dosages over a period of time. Treatment can be monitored by assaying antibody, or activated T-cell or B-cell responses to the therapeutic agent over time. If the response falls, a booster dosage is indicated. In the case of potential Down's syndrome patients, treatment can begin antenatally by administering therapeutic agent to the mother or shortly after birth.

In prophylactic applications, pharmaceutical compositions or medicaments are administered to a patient susceptible to, or otherwise at risk of, Alzheimer's disease in an amount sufficient to eliminate or reduce the risk, lessen the severity, or delay the outset of the disease, including biochemical, histologic and/or behavioral symptoms of the disease, its complications and intermediate pathological phenotypes presented during development of the disease. In therapeutic applications, compositions or medicaments are administered to a patient suspected of, or already suffering from, such a disease in an amount sufficient to cure, or at least partially arrest, the symptoms of the disease (biochemical, histologic and/or behavioral), including its complications and intermediate pathological phenotypes in development of the disease. In some methods, administration of agent reduces or eliminates mild cognitive impairment in patients that have not yet developed characteristic Alzheimer's pathology. An amount adequate to accomplish therapeutic or prophylactic treatment is defined as a therapeutically- or prophylactically-effective dose. In both prophylactic and therapeutic regimes, agents are usually administered in several dosages until a sufficient immune response has been achieved. Typically, the immune response is monitored and repeated dosages are given if the immune response starts to wane.

Effective doses of the compositions of the present invention, for the treatment of the above described conditions vary depending upon many different factors, including means of administration, target site, physiological state of the patient, other medications administered, and whether treatment is prophylactic or therapeutic. Treatment dosages need to be titrated to optimize safety and efficacy. The amount of immunogen depends on whether adjuvant is also administered, with higher dosages being required in the absence of adjuvant. The amount of an immunogen for administration sometimes varies from 1-500 µg per patient and more usually from 5-500 µg per injection for human administration. Occasionally, a higher dose of 1-2 mg per injection is used. Typically about 10, 20, 50, or 100 µg is used for each human injection. The mass of immunogen also depends on the mass ratio of immunogenic epitope within the immunogen to the mass of immunogen as a whole. Typically, $10^{-3}$ to $10^{-55}$ micromoles of immunogenic epitope are used for each microgram of immunogen. The timing of injections can vary significantly from once a day, to once a year, to once a decade. On any given day that a dosage of immunogen is given, the dosage is greater than 1 µg/patient and usually greater than 10 µg/patient if adjuvant is also administered, and greater than 10 µg/patient and usually greater than 100 µg/patient in the absence of adjuvant. A typical regimen consists of an immunization followed by booster injections at time intervals, such as 6 week intervals. Another regimen consists of an immunization followed by booster injections 1, 2, and 12 months later. Another regimen entails an injection every two months for life. Alternatively, booster injections can be on an irregular basis as indicated by monitoring of immune response.

For passive immunization with an antibody, the dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once per every two weeks or once a month or once every 3 to 6 months. In some methods, two or more monoclonal antibodies with different binding specificities are administered simultaneously, in which case the dosage of each antibody administered falls within the ranges indicated. Antibody is usually administered on multiple occasions. Intervals between single dosages can be weekly, monthly, or yearly. In some methods, dosage is adjusted to achieve a plasma antibody concentration of 1-1000 µg/ml and in some methods 25-300 µg/ml. Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

Doses for nucleic acids encoding immunogens range from about 10 ng to 1 g, 100 ng to 100 mg, 1 µg to 10 mg, or 30-300 µg DNA per patient. Doses for infectious viral vectors vary from 10-100, or more, virions per dose.

Agents for inducing an immune response can be administered by parenteral, topical, intravenous, oral, subcutaneous, intraarterial, intracranial, intraperitoneal, intranasal, or intramuscular means for prophylactic and/or therapeutic treatment. The most typical route of administration of an immunogenic agent is subcutaneous although other routes can be equally effective. The next most common route is intramuscular injection. This type of injection is most typically performed in the arm or leg muscles. In some methods, agents are injected directly into a particular tissue where deposits have accumulated, for example intracranial injection. Intramuscular injection on intravenous infusion are preferred for administration of antibody. In some methods, particular therapeutic antibodies are injected directly into the cranium. In some methods, antibodies are administered as a sustained release composition or device, such as a Medipad™ device (Elan Pharm. Technologies, Dublin, Ireland).

Another aspect of the present invention is a combination therapy wherein a tau protein, its immunogenic epitope, or antibodies recognizing the tau protein or immunogenic epitope is administered in combination with other agents that are effective for treatment of related neurodegenerative diseases. In the case of amyloidogenic diseases such as, Alzheimers disease and Down's syndrome, immune modulation to clear amyloid-beta (Aβ) deposits is an emerging therapy. Immunotherapies targeting Aβ have consistently resulted in cognitive improvements. It is likely that tau and Aβ pathologies are synergistic. Therefore, a combination therapy targeting the clearance of both pathologies at the same time may be more effective than targeting each individually. In the case of Parkinson's Disease and related neurodegenerative diseases, immune modulation to clear aggregated forms of the α-synuclein protein is also an emerging therapy. A combination therapy which targets the clearance of both tau and α-synuclein proteins simultaneously may be more effective than targeting each individually.

Immunogenic agents of the present invention, such as peptides, are sometimes administered in combination with an adjuvant. A variety of adjuvants can be used in combination with a peptide, such as tau, to elicit an immune response. Preferred adjuvants augment the intrinsic response to an immunogen without causing conformational changes in the immunogen that affect the qualitative form of the response.

A preferred class of adjuvants is aluminum salts (alum), such as aluminum hydroxide, aluminum phosphate, and aluminum sulfate. Such adjuvants can be used with or without other specific immunostimulating agents, such as 3 De-O-acylated monophosphoryl lipid A (MPL) or 3-DMP, polymeric or monomeric amino acids, such as polyglutamic acid or polylysine. Such adjuvants can be used with or without other specific immunostimulating agents, such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'dipalmitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) Theramide™), or other bacterial cell wall components. Oil-in-water emulsions include (a) MF59 (WO 90/14837 to Van Nest et al., which is hereby incorporated by reference in its entirety), containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton Mass.), (b) SAF, containing 10% Squalene, 0.4% Tween 80, 5% pluronic-blocked polymer L121, and thr-MDP, either microfluidized into a submicron emulsion or vortexed to generate a larger particle size emulsion, and (c) RibiT adjuvant system (RAS), (Ribi ImmunoChem, Hamilton, Mont.) containing 2% squalene, 0.2% Tween 80, and one or more bacterial cell wall components from the group consisting of monophosphoryllipid A (MPL), trehalose dimycolate (TDM), and cell wall skeleton (CWS), preferably MPL+ CWS (Detox™). Other adjuvants include Complete Freund's Adjuvant (CFA) and Incomplete Freund's Adjuvant (IFA). Other adjuvants include cytokines, such as interleukins (IL-1, IL-2, and IL-12), macrophage colony stimulating factor (M-CSF), and tumor necrosis factor (TNF).

An adjuvant can be administered with an immunogen as a single composition, or can be administered before, concurrent with, or after administration of the immunogen. Immunogen and adjuvant can be packaged and supplied in the same vial or can be packaged in separate vials and mixed before use. Immunogen and adjuvant are typically packaged with a label, indicating the intended therapeutic application. If immunogen and adjuvant are packaged separately, the packaging typically includes instructions for mixing before use. The choice of an adjuvant and/or carrier depends on the stability of the immunogenic formulation containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, Complete Freund's adjuvant is not suitable for human administration. However, alum, MPL or Incomplete Freund's adjuvant (Chang et al., Advanced Drug Delivery Reviews 32:173-186 (1998), which is hereby incorporated by reference in its entirety) alone or optionally all combinations thereof are suitable for human administration.

Agents of the present invention are often administered as pharmaceutical compositions comprising an active therapeutic agent and a variety of other pharmaceutically acceptable components. See Remington's Pharmaceutical Science (15th ed., Mack Publishing Company, Easton, Pa., 1980), which is hereby incorporated by reference in its entirety. The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Pharmaceutical compositions can also include large, slowly metabolized macromolecules, such as proteins, polysaccharides like chitosan, polylactic acids, polyglycolic acids and copolymers (e.g., latex functionalized sepharose, agarose, cellulose, and the like), polymeric amino acids, amino acid copolymers, and lipid aggregates (e.g., oil droplets or liposomes). Additionally, these carriers can function as immunostimulating agents (i.e., adjuvants).

For parenteral administration, agents of the present invention can be administered as injectable dosages of a solution or suspension of the substance in a physiologically acceptable diluent with a pharmaceutical carrier that can be a sterile liquid such as water, oil, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin. Peanut oil, soybean oil, and mineral oil are all examples of useful materials. In general, glycols, such as propylene glycol or polyethylene glycol, are preferred liquid carriers, particularly for injectable solutions. Agents of the invention, particularly, antibodies, can be administered in the form of a depot injection or implant preparation which can be formulated in such a manner as to permit a sustained release of the active ingredient. An exemplary composition comprises monoclonal antibody at 5 mg/mL, formulated in aqueous buffer consisting of 50 mM L-histidine, 150 mM NaCl, adjusted to pH 6.0 with HCl.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles, such as polylactide, polyglycolide, or copolymer, for enhanced adjuvant effect (Langer, et al., Science 249:1527 (1990); Hanes, et al., Advanced Drug Delivery Reviews 28:97-119 (1997), which are hereby incorporated by reference in their entirety).

Additional formulations suitable for other modes of administration include oral, intranasal, and pulmonary formulations, suppositories, and transdermal applications.

For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

Topical application can result in transdermal or intradermal delivery. Topical administration can be facilitated by co-administration of the agent with cholera toxin or detoxified derivatives or subunits thereof or other similar bacterial toxins (See Glenn et al., Nature 391:851 (1998), which is hereby incorporated by reference in its entirety). Co-administration can be achieved by using the components as a mixture or as linked molecules obtained by chemical cross-linking or expression as a fusion protein.

Alternatively, transdermal delivery can be achieved using a skin path or using transferosomes (Paul et al., Eur. J. Immunol. 25:3521-24 (1995); Cevc et al., Biochem. Biophys. Acta 1368:201-15 (1998), which are hereby incorporated by reference in their entirety).

EXAMPLES

Example 1—Peptides

The peptide immunogen, Tau 379-408 [P-Ser$_{396,404}$] was synthesized at the Keck facility (Yale University), by the solid-phase technique on a p-methyl-benzhydrylamine resin, using a Biosearch SAM 2 synthesizer (Biosearch, Inc., San Rafael, Ca.). The peptide was cleaved from the resin with HF and then extracted with ether and acetic acid before lyophilization. Subsequently, it was purified by HPLC with the use of a reverse-phase support medium (Delta-Bondapak) on a 0.78×30 cm column with a 0-66% linear gradient of acetonitrile in 0.1% TFA.

Example 2—Expression and Purification of Recombinant Tau Protein pcDNA3.1(+) mutant tau P301L construct, expressing tau which has two N-terminal exons (58 residues) and contains all the microtubule (MT) binding repeats in the longest human tau isoform. The cDNA was subcloned in pET30a vector using standard methods. The plasmid DNA was prepared using the Qiagen protocol (Qiagen, Chatsworth, Calif.), and used to transform *Escherichia coli* BL21-DE3 competent cells. The clones were sequenced after transformation to verify the presence of the desired mutation and to confirm that the rest of the tau sequence was identical with the published human cDNA sequence.

Tau purification was performed as described (Connell et al., "Effects of FTDP-17 Mutations on the In Vitro Phosphorylation of Tau by Glycogen Synthase Kinase 3Beta Identified by Mass Spectrometry Demonstrate Certain Mutations Exert Long-Range Conformational Changes," *FEBS Lett.* 493:40-44 (2001), which is hereby incorporated by reference in its entirety). Transformed bacteria were grown in LB broth containing kanamycin. The expression plasmid within the transformed cells was then induced to express the tau protein of interest by adding IPTG. The bacterial suspension was then centrifuged and the pellets resuspended in 50 mM MES buffer pH 6.5, with protease inhibitors (Complete, Roche, Indianapolis, Ind.), sonicated, and centrifuged at 15,000×g at 4° C. for 25 min. The supernatant was added to equal volume of 0.5 M NaCl to separate out tau in its soluble form. This solution was boiled until a white precipitate formed, subsequently centrifuged at 4° C. for 2 h at 100,000×g, and then tau was precipitated out of the supernatant with ammonium sulphate. Following centrifugation at 4° C. for 30 min at 15,000×g, the supernatant was removed and the tau pellets resuspended in 50 mM MES, pH 6.5, containing 1 mM DTT and 50 mM NaCl. Following dialysis, the tau was purified with FPLC.

Example 3—Antibody Purification and FITC Labeling

A polystyrene mini column (Pierce, Rockford, Ill.) was loaded with 1 ml of Gamma bind plus sepharose matrix (Amersham Biosciences, UK) and allowed to settle. The column was washed extensively (at least 5 bed volumes) with binding buffer (0.01 M sodium phosphate, 0.15 M NaCl, and 0.01 M EDTA, pH 7.0) to return the pH to the neutral range. The column was then incubated with 1 ml of phosphate buffered saline (PBS) diluted mouse plasma for 5 min at room temperature. This was then re-applied once more over the column to increase the yield of bound antibodies. Unbound protein was washed from the column with the binding buffer. Elution buffer (250 µl, 0.5 M acetic acid, pH 3.0) was applied sequentially to the column and aliquots of elution fractions were collected. The samples were quantified using the BCA protein assay kit (Pierce) and were also resolved on a 10% SDS-PAGE gel. The appropriate fractions containing the cleanest separation of IgG from other serum proteins (typically fractions 5-8) were pooled and dialyzed over night at 4° C. in 0.1 M Tris buffer pH 7.4 to quickly neutralize the elution reagent's pH, before using the samples for further experiments.

For the labeling studies, fluorescein isothiocyanate (FITC; Sigma) was covalently conjugated to the IgG via primary amines. Briefly, 1 mg of IgG was dissolved in 100 mM sodium carbonate-bicarbonate buffer, pH 9.0, to a final reaction volume of 0.25 ml, and reacted with 5× molar ratio of FITC by adding 50 µl of FITC (1 mg/ml) very slowly in 5 µl aliquots. The FITC was solubilized in anhydrous dimethyl sulfoxide (DMSO). The reaction vial was then covered with aluminum foil, and incubated for 8 h at 4° C. with gentle stirring. Ammonium chloride was then added to 5 mM and the reaction was incubated at 4° C. for 2 h. Lastly, xylene cyanol was added to 0.1%, and to separate unbound FITC, the mixture was applied to a PD-10 (Sephadex G-25M; Amersham) column gel bed that had been equilibrated with PBS solution. Subsequently, the flow through was collected and the column was eluted with 2.5 ml of PBS, in 0.25 ml fractions. Two bands were visible during elution, and the conjugate was present in the first band (fractions 3-5), as determined by measuring the absorbance of each fraction at 280 nm and then at 495 nm (The, et al., "Conjugation of Fluorescein Isothiocyanate to Antibodies. II. A Reproducible Method," *Immunology* 18:875-881 (1970), which is hereby incorporated by reference in its entirety). The IgG was purified from a mouse with a high titer against the immunogen (Phos-tau) and purified mouse IgG (Sigma) from pooled mouse plasma was used in controls.

Example 4—Fibrillogenicity

Aliquots of the tau peptide immunogen prepared in 0.1 M Tris, pH 7.4 were incubated for different times, and their fibril formation compared to that of Aβ1-42. In vitro fibrillogenesis was evaluated by an assay based on the fluorescence emission by thioflavin T (ThT), as previously described in Sigurdsson, et al., "Immunization with a Non-Toxic/Non-Fibrillar Amyloid-β Homologous Peptide Reduces Alzheimer's Disease Associated Pathology in Transgenic Mice," *Am J Pathol.* 159:439-447 (2001); Sigurdsson, et al., "An Attenuated Immune Response is Sufficient to Enhance Cognition in an Alzheimer's Disease Mouse Model Immunized with Amyloid-beta Derivatives," *J Neurosci.* 24:6277-6282 (2004), which are hereby incorporated by reference in their entirety. ThT binds specifically to β-sheet structure and this binding produces a shift in its emission spectrum and a fluorescent enhancement proportional to the amount of amyloid formed. Following the incubation period, 50 mM glycine, pH 9.2, and 2 µM ThT was added to a final volume of 200 µl containing 3 µg of the immunogen or the P301L tau peptide (with or without equimolar concentration of antibodies purified from the immunized mice). Fluorescence was measured at excitation 435 nm and emission 485 nm on a SpectraMax M2 multi-detection plate reader (Molecular Devices, Sunnyvale, Calif.).

Example 5—Neurotoxicity

Potential neurotoxicity of the tau derivative (10 µM) (SEQ ID NO:2) was evaluated at 6 days in a human neuroblastoma cell line (SK-N-SH) using the standard MTT assay as described by the manufacturer (Roche, Pleasanton, Ca.). Aβ1-40 and Aβ1-42 were used as control peptides.

Example 6—Animals Used in Studies

The studies were performed in the transgenic (Tg) P301L mouse model that develops neurofibrillary tangles in several brain regions and spinal cord (Taconic, Germantown, N.Y.) (Lewis, et al., "Neurofibrillary Tangles, Amyotrophy and Progressive Motor Disturbance in Mice Expressing Mutant (P301L) Tau Protein," *Nat Genet*. 25:402-405 (2000), which is hereby incorporated by reference in its entirety). While this model is not ideal for AD, it is an excellent model to study the consequences of tangle development and for screening therapy that may prevent the generation of these aggregates. Another advantage of these animals is the relatively early onset of pathology. In the homozygous line, behavioral abnormalities associated with tau pathology can be observed at least as early as 3 months, but the animals remain relatively healthy at least until 8 months of age. In other words, at 8 months, the animals ambulate, feed themselves, and can perform the behavioral tasks sufficiently well to allow the treatment effect to be monitored.

Example 7—Vaccine Administration

Phos-tau peptide was mixed with Adju-Phos adjuvant (Brenntag Biosector, Denmark) at a concentration of 1 mg/ml and the solution was rotated overnight at 4° C. prior to administration to allow the peptide to adsorb onto the aluminum phosphate particles. The mice received a subcutaneous injection of 100 µl followed by a second injection 2 weeks later and then monthly thereafter. In the first study, vaccination started at 2 months of age and continued until the animals were 5 months of age at which time the animals were perfused and their organs collected for analysis. In the latter study, the mice were immunized starting at 2 months of age and continued until the animals were 8 months. The mice went through a battery of sensorimotor tests at 5 months and again at 8 months of age prior to sacrifice. Control mice received the adjuvant alone.

Example 8—Intracarotid Injection of FITC-Labeled Antibodies

Mice were anesthetized with 2% isoflurane and maintained with 1.5% isoflurane in 70% $N_2O$ and 30% $O_2$. After exposing the carotid sheath, left common carotid artery (CCA), external carotid artery (ECA), and internal carotid artery (ICA) were exposed via a midline incision. A silk suture was tied to the distal end of the ECA, and the left CCA, ICA, and pterygopalatine artery (PPA) were temporarily tied. A 30 G needle connected to PE-10 tubing (Becton Dickinson, San Diego, Calif.) was attached to a 1 ml syringe, mounted on a pump, and the FITC-IgG conjugate was then administered over a period of 10-15 min through the needle punctured upward into the common carotid. Subsequently, the needle was slowly withdrawn and glue was applied to the site of injection to prevent postoperative bleeding. One hour later, the mice were perfused transaortically with PBS and periodate-lysine-paraformaldehyde (PLP) and postfixed in PLP overnight. The brains were then placed overnight in a phosphate buffer solution containing 20% glycerol and 2% DMSO. Subsequently, serial coronal 40 µm sections of the brain were prepared and subject to fluorescent microscopy.

Example 9—Antibody Response

The mice were bled prior to the commencement of the study and a week following each injection. The antibody response to the vaccine was determined by serial dilution of plasma using an ELISA assay as described previously (Sigurdsson, et al., "Immunization with a Non-Toxic/Non-Fibrillar Amyloid-) Homologous Peptide Reduces Alzheimer's Disease Associated Pathology in Transgenic Mice," *Am J Pathol*. 159:439-447 (2001); Sigurdsson, et al., "An Attenuated Immune Response is Sufficient to Enhance Cognition in an Alzheimer's Disease Mouse Model Immunized with Amyloid-beta Derivatives," *J Neurosci*. 24:6277-6282 (2004), which are hereby incorporated by reference in their entirety), where the immunogen was coated onto Immulon™ microtiter wells (Thermo Fischer Scientific, Waltham, Mass.,). For detection, goat anti-mouse IgG linked to a horseradish peroxidase (Amersham, Piscataway, N.J.) was used at 1:3000 dilution. Tetramethyl benzidine (Pierce) was the substrate.

Example 10—Histology

Mice were anesthetized with sodium pentobarbital (120 mg/kg, i.p.), perfused transaortically with PBS and the brains processed as previously described (Sigurdsson, et al., "Immunization with a Non-Toxic/Non-Fibrillar Amyloid-β Homologous Peptide Reduces Alzheimer's Disease Associated Pathology in Transgenic Mice," *Am J Pathol*. 159:439-447 (2001); Sigurdsson, et al., "An Attenuated Immune Response is Sufficient to Enhance Cognition in an Alzheimer's Disease Mouse Model Immunized with Amyloid-beta Derivatives," *J Neurosci*. 24:6277-6282 (2004); Sigurdsson E., "Histological Staining of Amyloid-beta in Mouse Brains," *Methods Mol Biol*. 299:299-308 (2005), which are hereby incorporated by reference in their entirety). Briefly, the right hemisphere was immersion fixed overnight in periodate-lysine-paraformaldehyde (PLP), whereas the left hemisphere was snap-frozen for tau protein analysis (see Western Blots below). Following fixation, the brain was moved to a phosphate buffer solution containing 20% glycerol and 2% dimethylsulfoxide (DMSO) and stored at 4° C. until sectioned. Serial coronal brain sections (40 µm) were cut and every tenth section was stained with two tau antibodies that recognize abnormal tau protein (PHF1, MC1). The series were placed in ethylene glycol cryoprotectant and stored at −20° C. until used.

Tau antibody staining was performed as described in Sigurdsson, et al., "Immunization with a Non-Toxic/Non-Fibrillar Amyloid-β Homologous Peptide Reduces Alzheimer's Disease Associated Pathology in Transgenic Mice," *Am J Pathol*. 159:439-447 (2001); Sigurdsson, et al., "An Attenuated Immune Response is Sufficient to Enhance Cognition in an Alzheimer's Disease Mouse Model Immunized with Amyloid-beta Derivatives," *J Neurosci*. 24:6277-6282 (2004), which are hereby incorporated by reference in their entirety. Briefly, sections were incubated in the tau primary antibodies, MC1 and PHF1, at a 1:50 to 1:100 dilution. A mouse on mouse immunodetection kit (Vector Laboratories, Burlingame, Calif.) was used, in which the anti-mouse IgG secondary antibody was used at a 1:2000 dilution.

Mice that received intracarotid injection of FITC-labeled purified mouse IgG were perfused one hour following the injection with PBS until the perfusate was clear and subsequently with PLP for 10 minutes followed by further PLP fixation overnight. The brain was then placed overnight in the glycerol/DMSO phosphate buffer and then immediately sectioned, mounted, and coverslipped using fluorescence compatible mounting media (Dako). Adjacent sections were stained free-floating with PHF1 or MC1 anti-tau antibodies followed by reaction with Texas red labeled anti-mouse IgG.

Sections were counterstained with 4'-6-diamidino-2-phenylindole (DAPI) that labels nuclei. In contrast to the regular immunohistochemistry described above, blocking solution was not used prior to applying the primary antibody.

Example 11—Image Analysis

Analysis of tissue sections was quantified with a Bioquant image analysis system. The software uses hue, saturation, and intensity to segment objects in the image field. Thresholds were established with accurately identified objects on a standard set of slides and these segmentation thresholds remained constant throughout the analysis session. After establishing the threshold parameter, the image field was digitized with a frame grabber. The Bioquant software corrects for heterogeneity in background illumination (blank field correction) and calculates the measurement parameter for the entire field. For quantitative image analysis of immunohistochemistry, the granular layer of the dentate gyrus was initially selected which consistently contained intraneuronal tau aggregates (pretangles and tangles). This observation concurs with the original characterization of this model (Lewis, et al., "Neurofibrillary Tangles, Amyotrophy and Progressive Motor Disturbance in Mice Expressing Mutant (P301L) Tau Protein," *Nat Genet.* 25:402-405 (2000), which is hereby incorporated by reference in its entirety). The motor cortex and brain stem in these animals were also analyzed, because tau pathology in those regions may relate to the motor abnormalities observed in this model. All procedures were performed by an individual blind to the experimental conditions of the study. Sample numbers were randomized before the start of the tissue processing, and the code was broken only after the analysis was complete. For each antibody stain (PHF1, MC1), every tenth section from the mouse brain was sampled. In the dentate gyrus, the measurement was the percent of area in the measurement field at ×200 magnification occupied by reaction product with the tip of the dentate gyrus at the left edge of the field. Four to five sections were analyzed per animal. In the motor cortex, the measurement was the percent of neuronal staining in the field at ×100 magnification with the thickest region of the cingulum positioned at the lower left edge of the field. In the brain stem, the measurement was the percent of neuronal staining in the field at ×100 magnification with the center of the top edge of the field positioned below the Aqueduct of Sylvius. Five sections were analyzed per animal in those two brain regions.

Example 12—Western Blotting

Brains were homogenized in Tris-buffered saline (TBS; 10 mM Tris/150 mM NaCl (pH 7.4)) containing protease inhibitors (1 tablet in 10 ml TBS; Complete mini protease inhibitor cocktail tablet; Roche) and phosphatase inhibitors (1 mM NaF, 0.4 µM $Na_3VO_4$, and 0.5 µM okadaic acid). After initial preclearance centrifugation at 20,800×g for 5 min, the post nuclear supernatants were centrifuged at 100,000×g for 60 min, and the supernatants were collected. The resulting pellets were resuspended with an equal volume of homogenization buffer containing 0.1% SDS (pH 8.0) to generate high speed soluble samples.

Equal amounts of protein (BCA assay) were loaded and the samples were electrophoresed on 10% SDS-PAGE gels and transferred to nitrocellulose membranes. All blots were blocked (5% nonfat milk and 0.1% Tween-20 in TBS), then incubated with various antibodies over night. Subsequently, the blots were washed and incubated for 1 h at room temperature with peroxidase-conjugated, goat anti-rabbit or anti-mouse IgG (1:2000, Amersham), followed with washing and detection of bound antibodies (ECL; Pierce). Immunoreactivity of tau proteins was analyzed from scanned films using UN-SCAN-IT software. To compare the relative amount of tau protein, the densities of the immunoreactive bands corresponding to phospho-tau were normalized and reported, relative to the amounts of total tau protein.

Example 13—Antibodies for Tau Histology and Blots

PHF1 mAb was used at 1:500 for immunoblots and 1:50 for immunohistochemistry. PHF1 mAb recognizes phosphorylated serines 396 and 404 located within the microtubule-binding repeat on the C-terminal of PHF tau protein (Otvos, et al., "Monoclonal Antibody PHF-1 Recognizes Tau Protein Phosphorylated at Serine Residues 396 and 404," *J Neurosci Res.* 39:669-673 (1994), which is hereby incorporated by reference in its entirety). MC1 tau antibody was used as well (Jicha, et al., "Sequence Requirements for Formation of Conformational Variants of Tau Similar to those found in Alzheimer's Disease," *J Neurosci Res.* 55:713-723 (1999), which is hereby incorporated by reference in its entirety). Both these antibodies recognize the neurofibrillary tangles in the P301L mouse model (Lewis, et al., "Neurofibrillary Tangles, Amyotrophy and Progressive Motor Disturbance in Mice Expressing Mutant (P301L) Tau Protein," *Nat Genet.* 25:402-405 (2000), which is hereby incorporated by reference in its entirety). MC1 is a conformation dependent IgG1 antibody that is similar to Alz-50 (IgM). Its reactivity depends on both the $NH_2$ terminus (amino acids 7-9), and an amino acid sequence of tau (amino acids 313-322) in the third microtubule binding domain that is both necessary and sufficient for in vitro formation of filamentous aggregates of tau similar to those seen in AD (Jicha, et al., "Sequence Requirements for Formation of Conformational Variants of Tau Similar to those found in Alzheimer's Disease," *J Neurosci Res.* 55:713-723 (1999), which is hereby incorporated by reference in its entirety). The pathological conformation of tau recognized by MC1 may precede the aggregation of tau into filaments and the resultant neurofibrillary degeneration seen in AD (Jicha, et al., "Sequence Requirements for Formation of Conformational Variants of Tau Similar to those found in Alzheimer's Disease," *J Neurosci Res.* 55:713-723 (1999), which is hereby incorporated by reference in its entirety). 3G6 monoclonal antibody that recognizes total tau and anti-actin polyclonal antibody (1:2000; Sigma) were used as controls on Western blots.

Example 14—Behavioral Studies

Several tests were performed in the mice to determine: 1) If the tau-targeting therapy prevented or reversed the age-related sensorimotor abnormalities observed in the P301L mice; and 2) If the immunization had any behavioral effects per se. Cognitive analysis of these homozygous animals has not been previously reported, and it was determined that their sensorimotor defects would not enable them to properly navigate the radial arm maze, which has been used extensively to assess the cognitive status of Tg2576 mice that deposit Aβ within the brain (Sigurdsson, et al., "An Attenuated Immune Response is Sufficient to Enhance Cognition in an Alzheimer's Disease Mouse Model Immunized with Amyloid-beta Derivatives," *J Neurosci.* 24:6277-6282 (2004); Asuni, et al., "Vaccination of Alzheimer's Model Mice with Abeta Derivative in Alum Adjuvant Reduces Abeta Burden without Microhemorrhages," *Eur J Neurosci.* 24: 2530-2542 (2006), which are hereby incorporated by reference in their entirety). Hence, an object recognition test that requires less navigation was used. The tests utilized include: 1) locomotor activity; 2) motor and reflex behaviors: a) traverse beam test, b) accelerating rotarod; and 3) memory test: object recognition. Prior to sensorimotor testing, the mice were adapted to the room with lights on for 15 min.

Example 15—Locomotor Activity

Computerized recording of the activity of the animals over a designated period of time was performed. Exploratory locomotor activity was recorded in a circular open field activity chamber (70 cm in diameter). A video camera mounted above the chamber automatically recorded horizontal movements in the open field in each dimension (i.e., x, y, and two z planes). Total distance was measured in centimeters (cm) traveled and is defined as sequential movement interruptions of the animal (white) measured relative to the background (black). The duration of the behavior was timed for 15 min. Results are reported based on distance traveled (cm), mean resting time, and velocity (mean and maximum) of the animal.

Example 16—Rotarod

The animals were placed onto the rod (diameter 3.6 cm) apparatus to assess differences in motor coordination and balance by measuring fore- and hindlimb motor coordination and balance (Rotarod 7650 accelerating model; Ugo Basile, Biological Research Apparatus, Varese, Italy). This procedure was designed to assess motor behavior without a practice confound. The animals were habituated to the apparatus by receiving training sessions of two trials, sufficient to reach a baseline level of performance. Then, the mice were tested three additional times, with increasing speed. During habituation, the rotarod was set at 1.0 rpm, which was gradually raised every 30 sec, and was also wiped clean with 30% ethanol solution after each session. A soft foam cushion was placed beneath the apparatus to prevent potential injury from falling. Each animal was tested for three sessions, with each session separated by 15 min, and measures were taken for latency to fall or invert (by clinging) from the top of the rotating barrel.

Example 17—Traverse Beam

This task tests balance and general motor coordination and function integration. Mice were assessed by measuring their ability to traverse a graded narrow wooden beam to reach a goal box (Torres, et al., "Behavioural, Histochemical and Biochemical Consequences of Selective Immunolesions in Discrete Regions of the Basal Forebrain Cholinergic System," *Neuroscience* 63:95-122 (1994), which is hereby incorporated by reference in its entirety). The mice were placed on a 1.1 cm wide beam that is 50.8 cm long and suspended 30 cm above a padded surface by two identical columns. Attached at each end of the beam is a shaded goal box. Mice were placed on the beam in a perpendicular orientation to habituate and were then monitored for a maximum of 60 sec. The number of foot slips each mouse had before falling or reaching the goal box were recorded for each of four successive trials. Errors are defined as footslips and were recorded numerically. To prevent injury from falling, a soft foam cushion was always kept underneath the beam. Animals that fell off were placed back in their position prior to the fall.

Example 18—Object Recognition

The spontaneous object recognition test that was utilized measures deficits in short term memory, and was conducted in a square-shaped open-field box (48 cm square, with 18 cm high walls constructed from black Plexiglas), raised 50 cm from the floor. The light intensity was set to 30 lx. On the day before the tests, mice were individually habituated in a session in which they were allowed to explore the empty box for 15 min. During training sessions, two novel objects were placed at diagonal corners in the open field and the animal was allowed to explore for 15 min. For any given trial, the objects in a pair were 10 cm high, and composed of the same material so that they could not readily be distinguished by olfactory cues. The time spent exploring each object was recorded by a tracking system (San Diego Instruments, San Diego, Calif.), and at the end of the training phase, the mouse was removed from the box for the duration of the retention delay (RD=3 h). Normal mice remember a specific object after a delay of up to 1 h and spend the majority of their time investigating the novel object during the retention trial. During retention tests, the animals were placed back into the same box, in which one of the previous familiar objects used during training was replaced by a second novel object, and allowed to explore freely for 6 min. A different object pair was used for each trial for a given animal, and the order of exposure to object pairs as well as the designated sample and novel objects for each pair were counterbalanced within and across groups. The time spent exploring the novel and familiar objects was recorded for the 6 min. The percentage Short Term Memory score is the time spent exploring any one of the two objects (training session) compared to the novel one (retention session).

The objective of these experiments was to evaluate the effects of the vaccination on selected sensorimotor and cognitive behaviors. The homozygous P301L mice have tangle pathology as early as 3 months of age and those animals were tested at 5- and 8 months of age.

Example 19—Data Analysis

All the data was analyzed with GraphPad Prism 4.3. The amount of tau aggregates on western blots, the immunoreactivity on brain sections within the dentate gyrus, motor cortex and brainstem, the locomotor activity measurements (distance, Vmax, Vmean, rest time) and the object recognition test were analyzed by an unpaired t-test. When the data failed at least two out of three normality tests (KS-, D'Agostino & Pearson omnibus-, and Shapiro-Wilk normality tests) non-parametric Mann-Whitney test was used. The test was two-tailed when gender differences were analyzed but otherwise one-tailed because it was predicted that the immunotherapy would clear tau pathology that would slow the progression of behavioral impairments. Neurotoxicity was analyzed by one-way ANOVA and Neuman Keuls post hoc test. The data from the traverse beam and rotarod were analyzed by two-way ANOVA repeated measures and a Bonferroni post hoc test. Correlation between behavioral outcome and tau pathology, as assessed by immunohistochemistry or Western blotting, was analyzed by Pearson r correlation or Spearman rank correlation if the data failed normality test.

Example 20—In Vitro Assays

To determine the therapeutic potential of tau-based immunotherapy, a phosphorylated immunogen, Tau379-408 [P-Ser$_{396,404}$] (SEQ ID NO:2), was designed that would lead to the generation of antibodies which would selectively detect highly phosphorylated tau protein as found in AD and tangle mouse models. The tau protein, like the Aβ peptide, has the propensity to form β-sheets which have been associated with toxicity. To examine potential in vivo toxicity of the immunogen, its fibrillogenicity and neurotoxicity were examined in vitro. Data from the Thioflavin T assay demonstrate the immunogen is not fibrillogenic (FIG. 1A). Likewise, data from the MTT assay indicate the immunogen is not neurotoxic to SK-N-SH neurons as compared with neurons treated with Aβ1-42 for 6 days (10 μM, 20% reduction in neuronal viability, p<0.01).

Example 21—Animal Studies

Figure 1B:
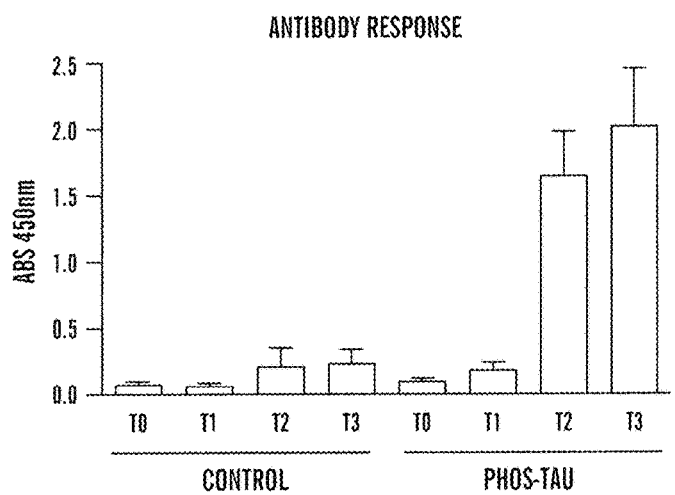
Figure 1C:
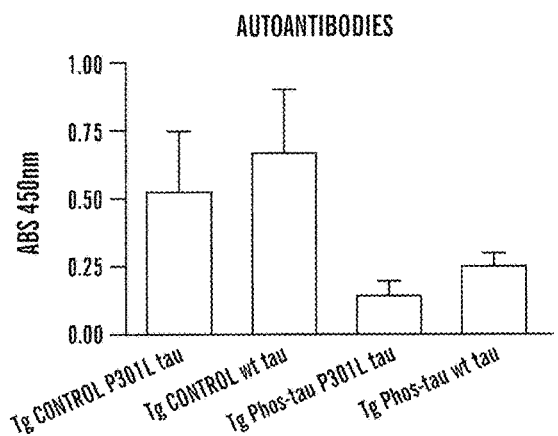
Figure 2A:
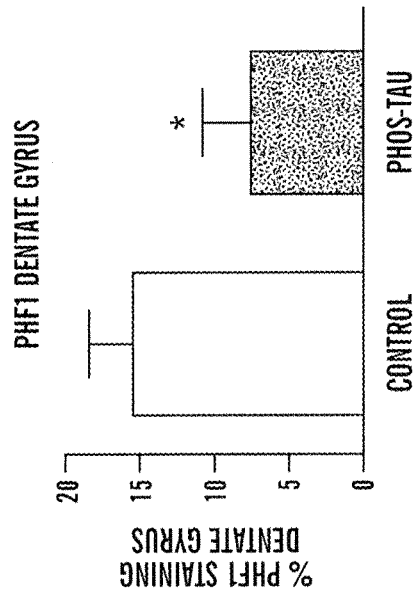
Figure 2B:
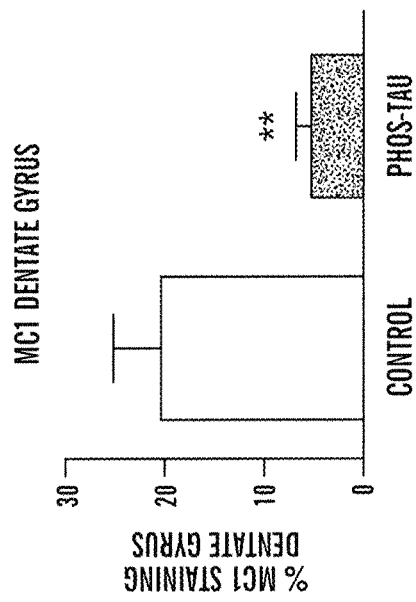
Figure 2E:
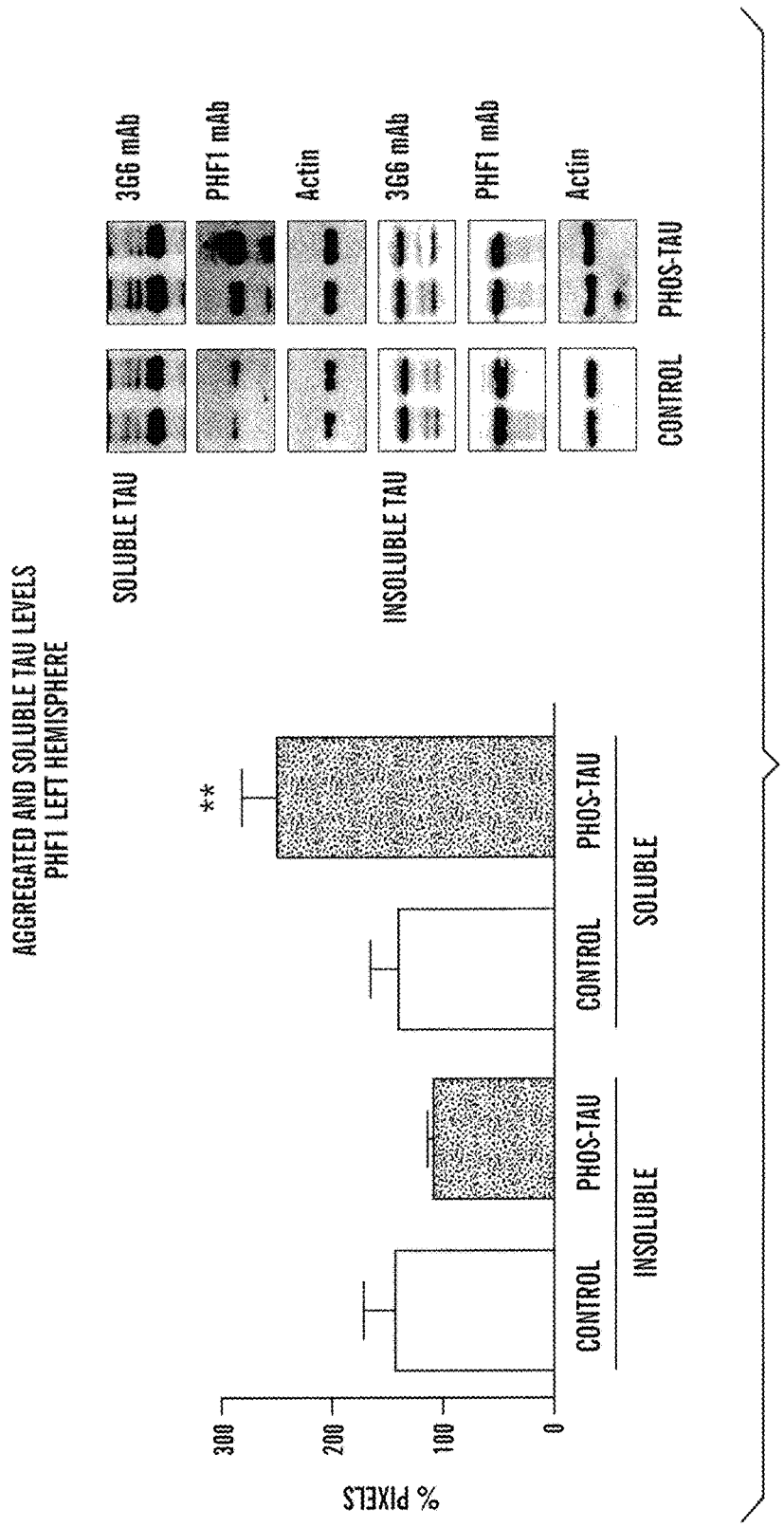
Figure 3A:
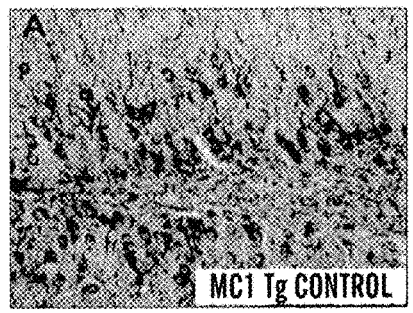
FIGS. 3A-H show that the immunotherapy reduces pathological tau in neurons. Representative examples of the histological regions that were analyzed in MC1- and PHF1-stained brain sections are shown. Neuronal tau aggregates were cleared in the dentate gyrus (DG), the motor cortex (MCx), and the brain stem (BS) in immunized mice compared to control mice. The dentate gyms develops extensive tau pathology at an early age in the homozygous P301L mice and tau pathology in the motor cortex and brain stem may relate to the motor deficits in this model.
Figure 3B:
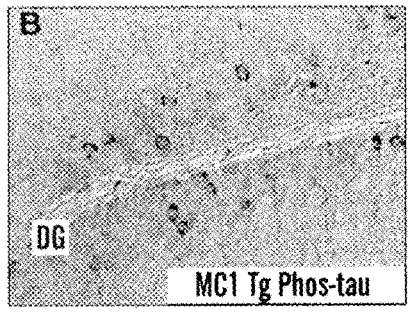
Figure 3C:
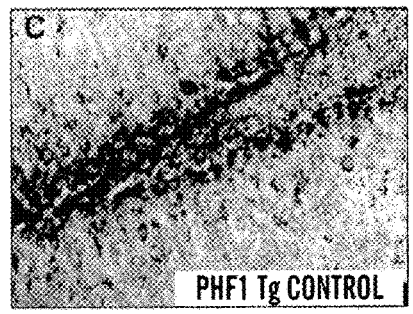
Figure 3D:
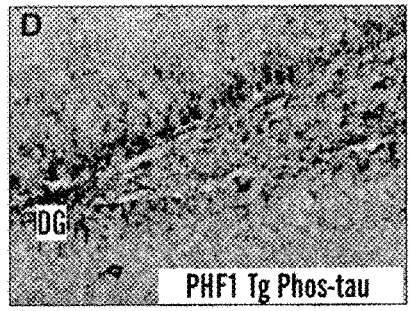
Figure 3E:
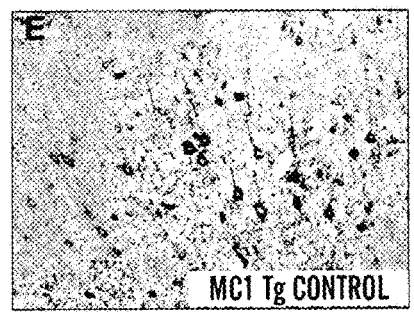
Figure 3F:
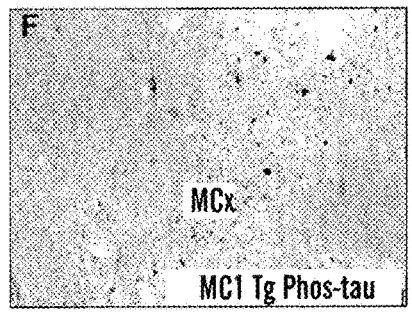
Figure 3G:
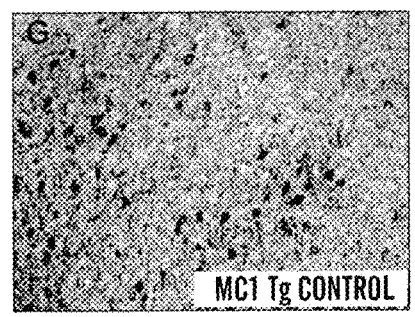
Figure 3H:
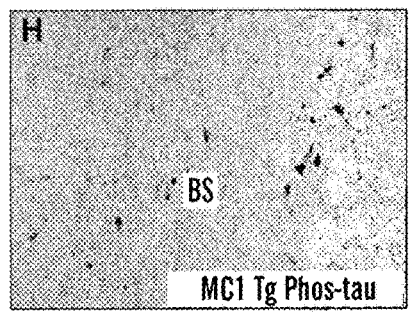

Treatment from 2-5 Months. Homozygous Tg P301L mice were immunized from 2 months of age with the Phos-tau peptide in aluminum adjuvant (n=12, 5 males and 7 females). Control Tg P301L animals received adjuvant alone (n=14, 8 males, 6 females). The mice elicited a robust antibody response against the immunogen, whereas minimal reactivity was observed in control mice (FIG. 1B). Surprisingly, autoantibodies that recognized recombinant tau (P301L and wild-type) were observed in controls and immunized mice (FIG. 1C). In the original description of a hemizygous line of this model, the most extensive pathology was observed in the brain stem and spinal cord (Lewis, et al., "Neurofibrillary Tangles, Amyotrophy and Progressive Motor Disturbance in Mice Expressing Mutant (P301L) Tau Protein," Nat Genet. 25:402-405 (2000), which is hereby incorporated by reference in its entirety). The homozygous line that was utilized also has extensive pathology in these regions but appears to have more pathology in the hippocampal and cortical regions than hemizygous animals which is as expected because of their homozygocity. Quantitative analysis of neuronal immunoreactivity in the dentate gyrus with two antibodies that selectively stain Alzheimer's tau protein revealed 74%—(p<0.01; FIG. 2A, FIG. 3A,B) and 52% (p<0.05, FIG. 2B, FIG. 3C,D) reduction in MC1- and PHF1 immunoreactivity, respectively. MC recognizes earlier stage of tau pathology than PHF (Jicha, et al., "Sequence Requirements for Formation of Conformational Variants of Tau Similar to those found in Alzheimer's Disease," J Neurosci Res. 55:713-723 (1999), which is hereby incorporated by reference in its entirety), and these intermediates should be more easily cleared than higher order aggregates which may explain the greater reduction in MC1—compared to PHF1 immunoreactivity. To confirm this finding in other brain regions that may better relate to the motor abnormalities in the model, neuronal MC1 staining was quantified in the motor cortex and brain stem, and immunoreactivity was reduced by 96% (p<0.0001, FIG. 2C, FIG. 3E,F) and 93% (p=0.01, FIG. 2D, FIG. 3G, H), respectively, compared to control Tg mice. No significant correlation was observed between antibody levels against the immunogen, recombinant wild-type tau or P301L tau versus the immunohistochemical analysis. Western blot analysis did not show as robust treatment effect as observed with immunohistochemistry (FIG. 2E). Densitometric analysis of the PHF1 blots revealed a strong trend for reduction in insoluble tau (28% reduction, p=0.09) and a significant increase in soluble tau (77% increase, p=0.01) in the immunized mice compared to control Tg mice. No significant changes were observed on MC1 blots although there was a strong trend for an increase in soluble tau (167% increase, p=0.10). Further analysis of the ratio of soluble tau to insoluble tau indicated a significant increase in the immunized group on PHF1 blots (89% increase, p=0.01), suggesting a mobilization of tau from its insoluble form to soluble form in these treated animals. Furthermore, a positive correlation was observed between antibody levels against the immunogen versus band density in PHF1 blots (insoluble tau: r=−0.60, p<0.01; ratio of soluble to insoluble tau, r=0.46, p<0.03).

Gender Differences.

More extensive tau pathology in females than males has been described in a hemizygous line of the P301L model (Lewis, et al., "Neurofibrillary Tangles, Amyotrophy and Progressive Motor Disturbance in Mice Expressing Mutant (P301L) Tau Protein," Nat Genet. 25:402-405 (2000), which is hereby incorporated by reference in its entirety) and this was considered in group assignments of the homozygous line of the P301L mice utilized. When gender differences in tau pathology as assessed by immunohistochemistry were compared, the female controls had more tau pathology in all areas analyzed than male controls but no gender differences were observed between immunized mice (Table 2). When the immunohistochemical data based on gender was reanalyzed, a greater treatment effect was observed among the females than males (Table 2).

TABLE 2

Immunohistochemical Analysis:
Treatment Effect within Gender and Gender Differences.

| | Dentate Gyrus (MC1) | | Dentate Gyrus (PHF1) | |
|---|---|---|---|---|
| | M | F | M | F |
| 2-5 months | | | | |
| Tg Control | 8.03 ± 2.44 | 37.05 ± 6.37+++ | 8.91 ± 3.62 | 23.96 ± 1.19++ |
| Tg Phos-tau | 6.94 ± 3.03 | 4.13 ± 1.26**** | 13.72 ± 6.89 | 2.78 ± 2.15*** |
| 2-8 months | | | | |
| Tg Control | 7.39 ± 3.40 | 30.21 ± 2.17+++ | 9.46 ± 6.78 | 24.54 ± 5.19 |
| Tg Phos-tau | 3.00 ± 1.89 | 17.18 ± 4.19**/++ | 7.32 ± 5.67 | 15.08 ± 6.38* |

TABLE 2-continued

Immunohistochemical Analysis:
Treatment Effect within Gender and Gender Differences.

| | Motor Cortex (MC1) | | Brain Stem (MC1) | |
|---|---|---|---|---|
| | M | F | M | F |
| 2-5 months | | | | |
| Tg Control | 0.89 ± 0.33 | 2.74 ± 0.48[++] | 0.38 ± 0.12 | 4.72 ± 1.89[++] |
| Tg Phos-tau | 0.09 ± 0.07* | 0.06 ± 0.03*** | 0.12 ± 0.04* | 0.19 ± 0.16** |
| 2-8 months | | | | |
| Tg Control | 2.09 ± 1.60 | 2.83 ± 1.54 | 1.88 ± 1.37 | 5.12 ± 1.29 |
| Tg Phos-tau | 0.08 ± 0.07** | 0.36 ± 0.12* | 0.23 ± 0.18* | 1.39 ± 0.31**/[++] |

Treatment Effect within Gender: Greater effect of the immunization was observed between females (8 out of 8 groups) than males (4 out of 8 groups).
*,,* $p \leq 0.05, 0.01, 0.001$. Significantly different from control mice within the same gender.
Gender Differences: Significant gender differences were observed between some of the groups.
In the 2-5 months study, males (n = 8) and female (n = 6) controls differed in all the areas analyzed but not phos-tau immunized males (n = 5) and females (n = 7).
In the 2-8 months study (6 males and 6 females per group), this difference was not as group specific with differences observed in the dentate gyrus (MC1) within both treatment groups and in the brain stem in the phos-tau immunized mice.
[+],[++],[+++] $p \leq 0.05, 0.01, 0.001$. Significantly different from males within the same treatment group.

A similar gender-related pattern was observed on Western blots (Table 3A), particularly in the ratio of soluble to insoluble tau (Table 3B), but gender specific treatment effect was not pronounced on the blots.

TABLE 3A-B

Western Blot Analysis
Treatment Effect within Gender and GenderDifferences,

A. Percentage density relative to total tau values.

| | Insoluable Tau PHF1 | | Soluble Tau PHF1 | | Insoluble Tau MC1 | | Soluble Tau MC1 | |
|---|---|---|---|---|---|---|---|---|
| | M | F | M | F | M | F | M | F |
| 2-5 months | | | | | | | | |
| Tg Control | 184 ± 35 | 96 ± 33 | 122 ± 15 | 169 ± 57 | 12 ± 3 | 17 ± 3 | 7 ± 1 | 3 ± 1[+] |
| Tg Phos-tau | 116 ± 12 | 95 ± 13 | 282 ± 46** | 218 ± 52 | 18 ± 6 | 27 ± 8 | 20 ± 9 | 7 ± 2* |
| 2-8 months | | | | | | | | |
| Tg Control | 39 ± 11 | 96 ± 24 | 111 ± 15 | 55 ± 6[++] | 11 ± 3 | 15 ± 6 | 54 ± 14 | 12 ± 4[++] |
| Tg Phos-tau | 38 ± 13 | 68 ± 14 | 77 ± 14 | 62 ± 5 | 11 ± 2 | 32 ± 21 | 56 ± 13 | 9 ± 3[++] |

B. Ratio of values in A (soluble/insoluble).

| | Ratio (soluble/insoluble) PHF1 | | Ratio (soluble/insoluble) MC1 | |
|---|---|---|---|---|
| | M | F | M | F |
| 2-5 months | | | | |
| Tg Control | 0.83 ± 0.14 | 2.04 ± 0.41[++] | 0.76 ± 0.15 | 0.16 ± 0.04[++] |
| Tg Phos-tau | 2.72 ± 0.62** | 2.36 ± 0.50 | 1.55 ± 0.90 | 0.36 ± 0.11 |
| 2-8 months | | | | |
| Tg Control | 4.26 ± 1.19 | 1.00 ± 0.38[+] | 5.73 ± 1.64 | 2.07 ± 0.88 |
| Tg Phos-tau | 2.98 ± 0.61 | 1.31 ± 0.45 | 5.20 ± 1.39 | 0.83 ± 0.34[++] |

Treatment Effect within Gender: (A) Greater effect of the immunization was observed between males in levels of soluble PHF1 tau and in females in levels of soluble MC1. In addition, the ratio of soluble/insoluble tau differed between treated- and control mice in PHF1 blots for males.
*, ** $p \leq 0.05, 0.01$. Significantly different from control mice within the same gender.
Gender Differences: Significant gender differences were observed between some of the groups but these differences were not as prevalent as in the immunohistochemical analysis.
In the 2-5 months study, males (n = 8) and female (n = 6) controls differed in soluble tau levels (MC1) as well as tau ratio (soluble/insoluble; PHF1 and MC1) but not phos-tau immunized males (n = 5) and females (n = 7). A similar pattern was observed in the immunohistochemical analysis with differences only observed in control goups.
In the 2-8 months study (6 males and 6 females per goup), this difference was not as group specific with differences observed in soluble tau (MC1, PHF1) as well as tau ratio (soluble/insoluble; PHF1) within controls. In the phos-tau immunized mice, gender differences were detected in soluble tau (MC1) as well as tau ratio (soluble/insoluble; MC1).
[+], [++] $p < 0.05, 0.01$. Significantly different from males within the same treatment group.

Treatment from 2-8 Months.

Figure 4B:
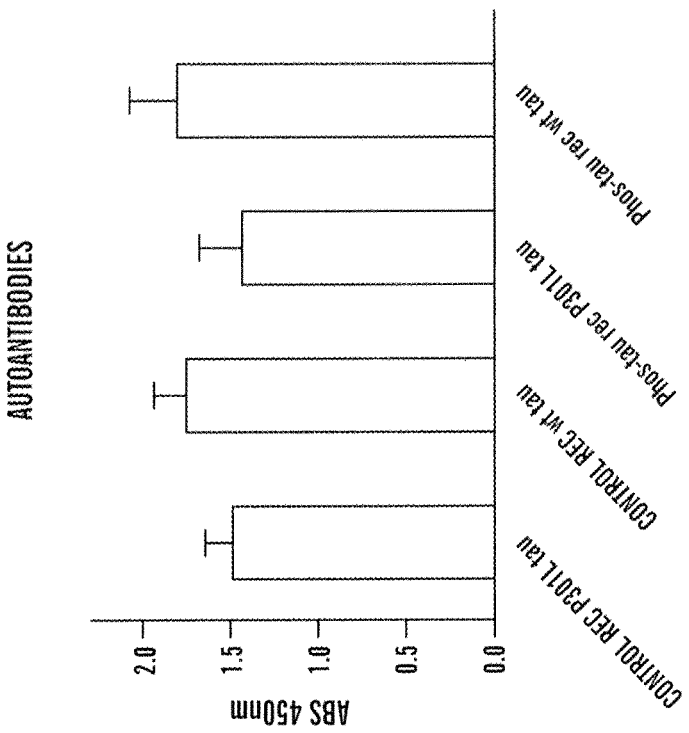
FIGS. 4A-B show that in mice treated from 2 to 8 months of age, the immunogenicity of the vaccine is confirmed but high levels of autoantibodies are detected. Homozygous transgenic (Tg) P301L mice were immunized from 2 months of age with phospho tau peptide (Tau379-408 [P-Ser$_{396,404}$]; n=12). Control Tg P301L animals received aluminum adjuvant alone (n=12). Sensorimotor performance was assessed at 5- and 8 months of age.
Figure 4A:
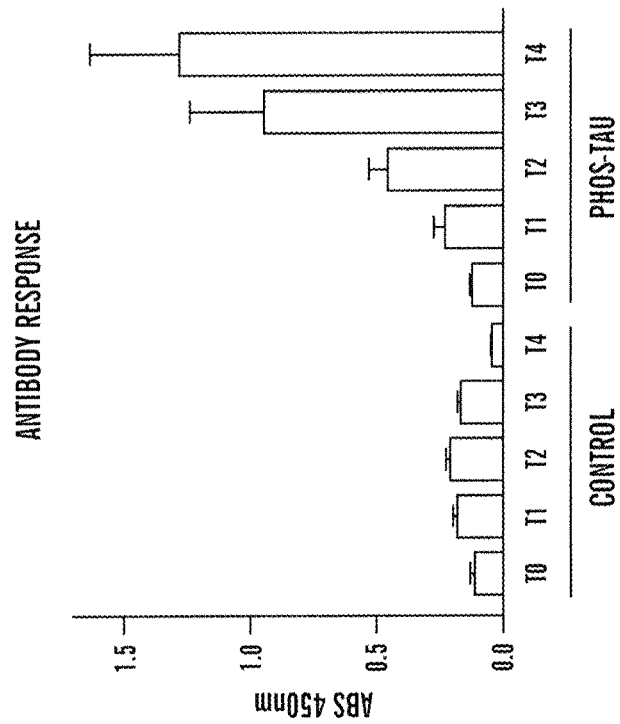

Following these promising findings, a longitudinal study was performed in another set of 2 month old homozygous P301L mice (n=12 per group, 6 males and 6 females per group). Again, a robust antibody response was elicited against the Phos-tau derivative and some, although much less reactivity was observed in control mice (FIG. 4A). Again, the plasma obtained at the end of the study in both the controls and immunized mice contained autoantibodies that recognized recombinant tau (P301L and wild-type; FIG. 4B). In these 8 month old animals, the level of these autoantibodies was substantially higher than in the 5 month old mice in the previous study (see FIG. 1C). It is well known that autoantibodies increase with age and applicants have observed a similar phenomenon in the Tg2576 mouse model of cerebral Aβ amyloidosis, although those animals are usually well into their second year when appreciable levels of autoantibodies are detected (Sigurdsson, et al., "An Attenuated Immune Response is Sufficient to Enhance Cognition in an Alzheimer's Disease Mouse Model Immunized with Amyloid-beta Derivatives," *J Neurosci*. 24:6277-6282 (2004); Asuni, et al., "Vaccination of Alzheimer's Model Mice with Abeta Derivative in Alum Adjuvant Reduces Abeta Burden without Microhemorrhages," *Eur J Neurosci*. 24: 2530-2542 (2006), which are hereby incorporated by reference in their entirety).

Figures 5A, 5B:
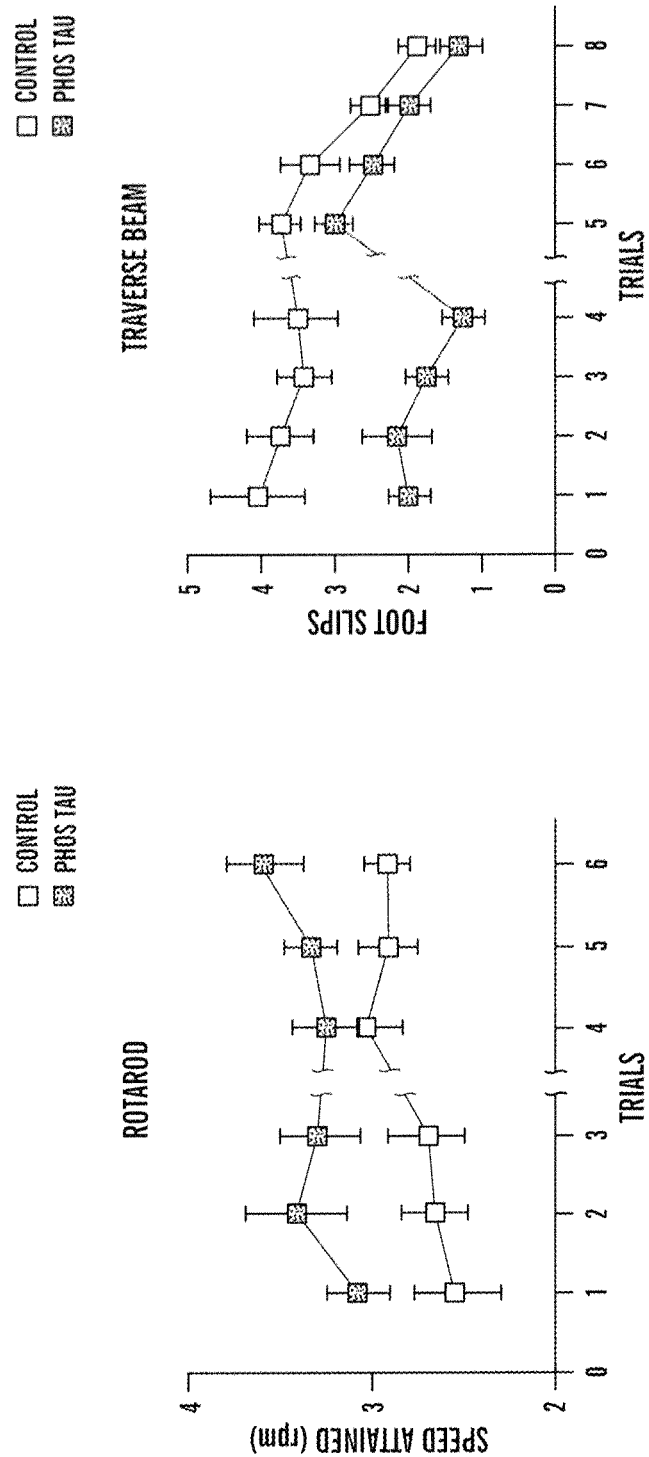
FIGS. 5A-D show that immunotherapy from 2 to 8 months of age slows the progression of behavioral abnormalities in P301L mice.
Figures 5C, 5D:
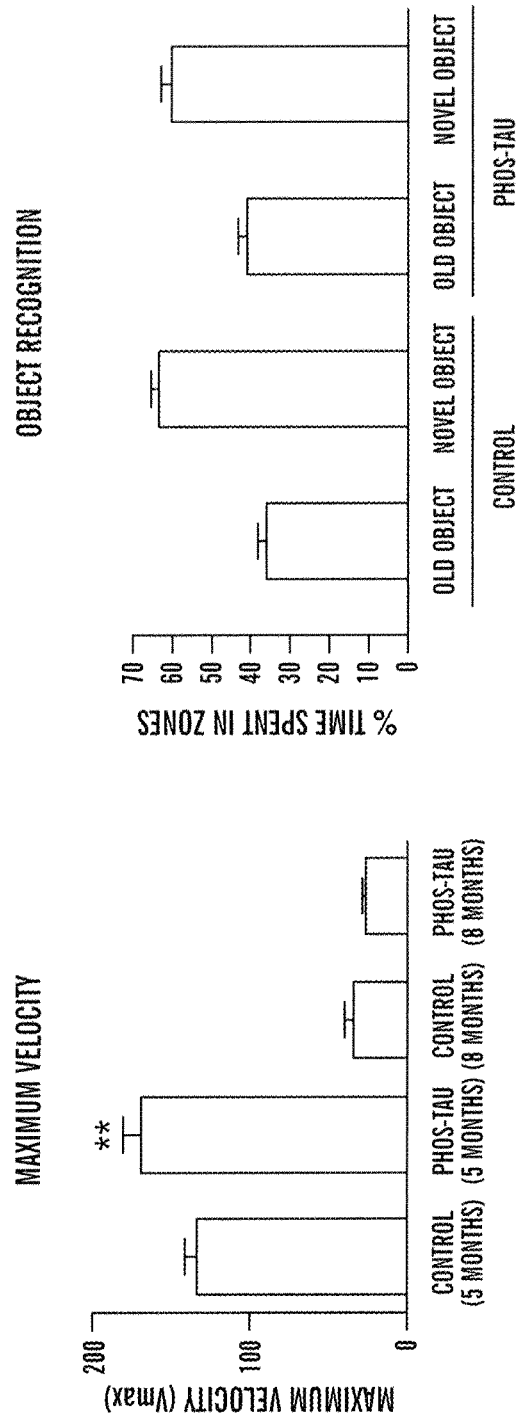

At 5 months of age, these animals underwent their first behavioral testing to determine if the therapy was associated with functional improvements. The immunization increased the time the animals were able to stay on the accelerating rotarod (p<0.02, FIG. 5A), and reduced the number of foot slips in the traverse beam task (p<0.001, FIG. 5B). Also, the vaccinated mice attained higher maximum velocity (Vmax: p=0.004, FIG. 5C) in the locomotor activity test but were not significantly different from Tg controls in the distance traveled, average speed (Vmean), or the resting time. These animals continued to receive monthly immunizations and were retested on the same behavioral tests at 8 months of age. The mice were subsequently killed for biochemical and histological analysis of tau pathology. At 8 months of age, the treated animals continued to perform better than Tg controls on the rotarod and traverse beam although the differences between the groups were not as substantial as during the earlier comparison (Rotarod: p<0.05, FIG. 5A; Traverse Beam: p=0.05, FIG. 5B). The locomotor activity of the groups was similar at this time point (Vmax in FIG. 5C). Overall, the groups performed worse at 8 months compared to 5 months. Because of the relatively poor mobility of the animals at this age, cognitive assessment was only performed with an object recognition test. This test indicated that both the immunized mice and their controls were cognitively normal, with the animals spending 60-70% of their time exploring the novel object (FIG. 5D), which is similar to wild-type mouse performance.

Figure 6B:
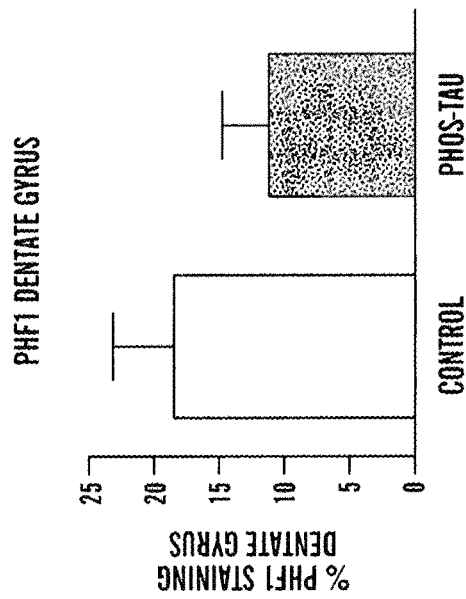
FIGS. 6A-D demonstrate that immunotherapy from 2 to 8 months reduces brain tau pathology.
Figure 6A:
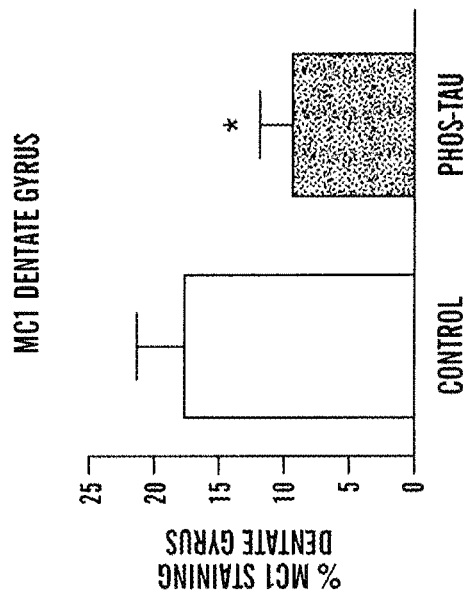
Figure 6C:
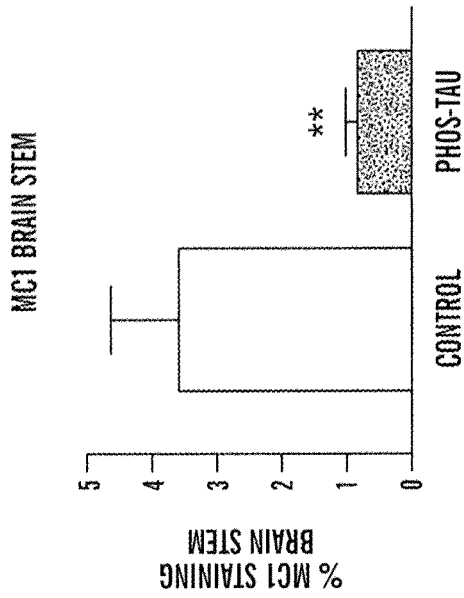
Figure 6D:
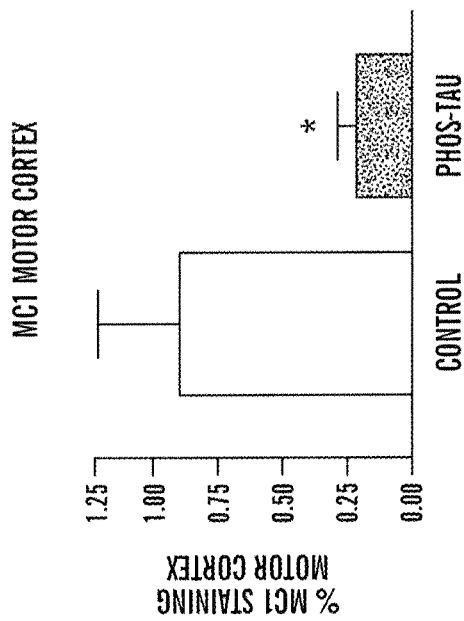
Figure 7A:
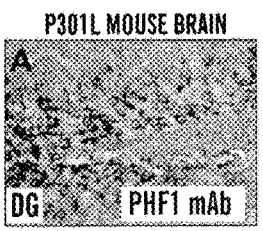
FIGS. 7A-L show that purified antibodies from immunized mice stain tau aggregates/tangles in neuronal cell bodies in P301L mice similar to the PHF1 antibody. Adjacent coronal brain sections are depicted through the dentate gyms (FIGS. 7A-D), motor cortex (FIGS. 7E-H), and brain stem (FIGS. 7I-L), immediately below the Aqueduct of Sylvius in a P301L transgenic mouse with tau pathology.
Figure 7B:
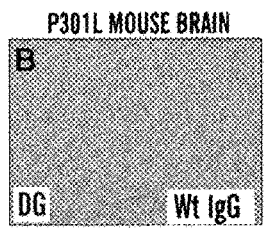
Figure 7C:
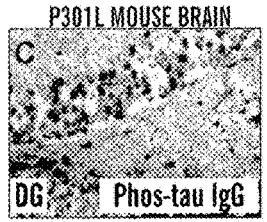
Figure 7D:
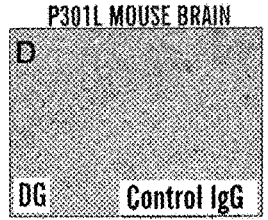
Figure 7E:
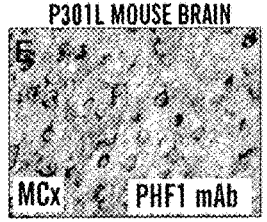
Figure 7F:
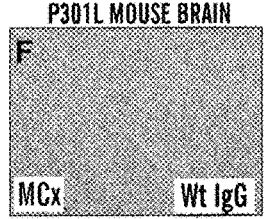
Figure 7G:
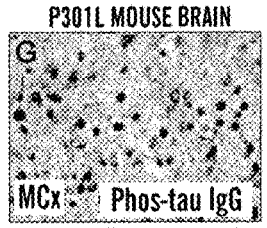
Figure 7H:
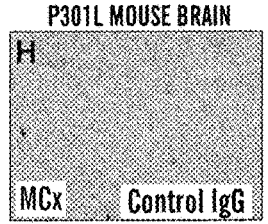
Figure 7I:
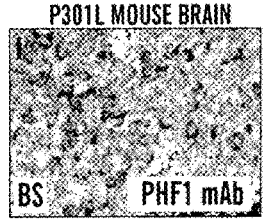
Figure 7J:
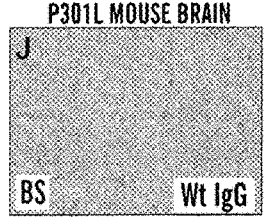
Figure 7K:
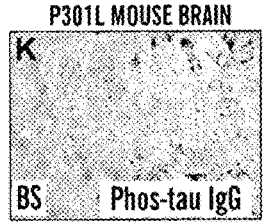
Figure 7L:
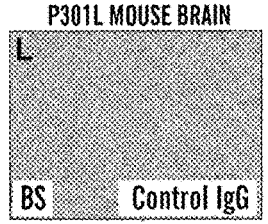

Quantitative analysis of tau immunoreactivity in the dentate gyrus revealed a 47% reduction (p<0.05, FIG. 6A) in MC1 staining and a strong trend (40% reduction, p=0.12, FIG. 6B) for reduced PHF1 immunoreactivity. As at 5 months of age, MC1 neuronal staining was more robustly reduced in the motor cortex (76%, p=0.02, FIG. 6C) and brain stem (78%, p=0.005, FIG. 6D) than in the dentate gyrus. Biochemical analysis of the whole left hemisphere of the brain did not reveal significant differences in pelletable tau or soluble tau on PHF1 or MC1 blots. Hence as expected, no correlation was observed between antibody levels against the immunogen vs. band density on PHF1- or MC1 blots of brain homogenate.

Interestingly, performance on behavioral assays that require extensive motor coordination (traverse beam and rotarod) correlated with tau pathology in corresponding brain areas (motor cortex and brain stem; Table 4).

TABLE 4

Behavioral assays at 8 months that correlated significantly with subsequent immunohistochemical analysis.

|  | Motor Cortex (MC1) | Brain Stem (MC1) |
| --- | --- | --- |
| Traverse Beam (8 months) | r = 0.47 p = 0.01 | r = 0.47 p = 0.01 |
| Rotarod (8 months) | r = −0.37 p = 0.04 | r = −0.45 p = 0.02 |

Of the behavioral assays performed at 5 and 8 months in the 2-8 months study, only the performance of the mice on the traverse beam and rotarod at 8 months showed any correlation with the subsequent immunohistochemical analysis. Notably, the only correlation was found between assays that require extensive motor coordination (traverse beam and rotarod) and corresponding brain areas (motor cortex and brain stem). r = Spearman r, p-value (one-tailed).

In addition, antibody levels against the immunogen, but not the recombinant tau proteins (wild-type and P301L), at the time of sacrifice (T4) correlated with tau pathology in the brain stem (MC1, r=−0.48, p<0.01), and dentate gyrums (MC1, r=−0.37, p=0.04, PHF1, r=−0.44, p=0.02), and there was a trend for a similar correlation in the motor cortex (MC1, r=−0.23, p=0.14).

Gender Differences.

As in the treatment study that lasted from 2-5 months, significant gender differences in immunohistochemical tau pathology were also observed in the 2-8 months study group. Again, females had more pathology than males although only in one brain region in controls (MC1: dentate gyrus) and in two brain regions in immunized mice (MC1: dentate gyms and brain stem; Table 2). In contrast, in the 2-5 months study group, the males and females in the control group differed in all the brain regions analyzed but no gender differences were observed in the immunized mice (Table 2). As in the 2-5 month group, greater treatment effect was observed among the females than males when the immunohistochemical data based on gender was reanalyzed (Table 2). A similar gender-related pattern was observed on Western blots with the females having more insoluble tau and less soluble tau than their male counterparts (Table 3). However, gender specific treatment effect was not observed at this time point.

Interestingly, although these gender differences in tau pathology were clearly observed, this pattern was not seen in the behavioral analysis. The only significant difference between males and females within the same group was observed in the rotarod at 5 months (p<0.05), with the females performing better (3.6±0.2 rpm) than the males (2.8±0.1 rpm).

Example 22—Antibody Characterization

Figure 8A:
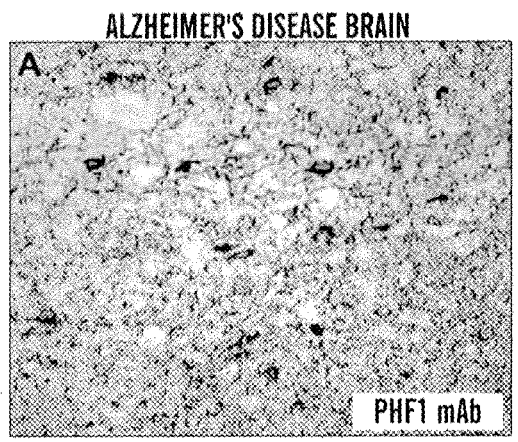
FIGS. 8A-C show purified antibodies from immunized mice stain tau aggregates/tangles in neuronal cell bodies in Alzheimer's disease similar to the PHF1 antibody.
Figure 8B:
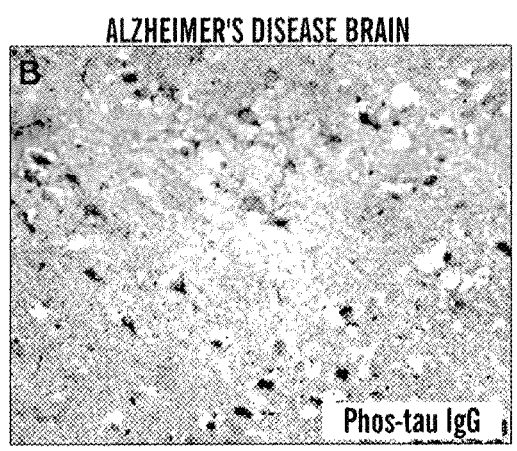
Figure 8C:
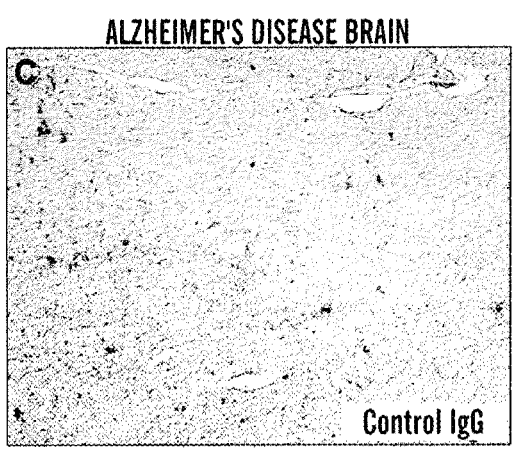
Figure 9A:
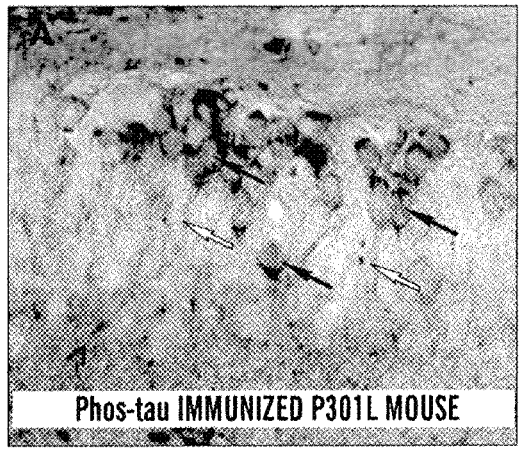
FIGS. 9A-B show intracerebral antibodies that label neurons are detected in the immunized P301L mice.
Figure 9B:
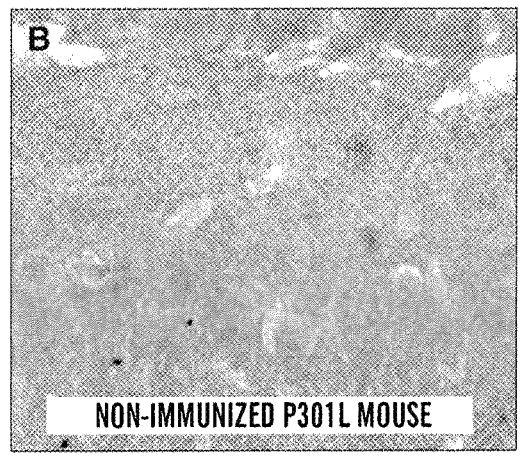

The high levels of autoantibodies observed in the animals complicates characterization of the antibodies that were generated towards the immunogen. Purified antibodies from several of the immunized mice stained specifically tau aggregates/tangles in neuronal cell bodies of P301L mice similar to the PHF-antibody and did not react with tau in wild-type mice (FIG. 7). But a similar staining pattern could be observed with antibodies purified from control animals with high levels of tau autoantibodies although most of them resulted in minimal or no staining in P301L or wild-type mice (FIG. 7). These findings indicate that the immunized mice generate antibodies that specifically recognize pathological tau aggregates in the P301L mouse, but some animals may contain autoantibodies with these properties. Likewise, the antibodies from the immunized mice stained tangle pathology in Alzheimer's brain (FIG. 8). By staining selected mouse brain sections with secondary antibody against mouse IgG, intracerebral antibodies that label neurons were detected in the P301L mice (FIG. 9).

Figure 10:
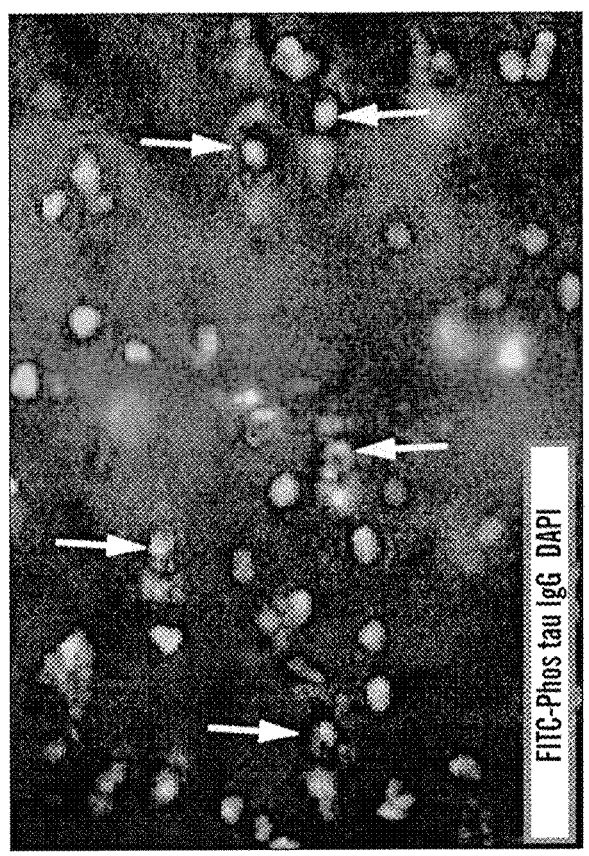
FIG. 10 shows a coronal brain section through the brachium of the inferior colliculus revealing FITC labeled neurons (arrows). Counterstain with DAPI (blue) shows nuclei of the neurons. Some FITC labeling was observed in a control P301L mouse of the same age that was injected with tagged antibodies from a control Tg mouse but neurons were not detected. No appreciable FITC fluorescence is observed in a wild-type mouse of the same age that received intracarotid injection of antibodies from an immunized mouse or a control mouse.
Figure 11A:
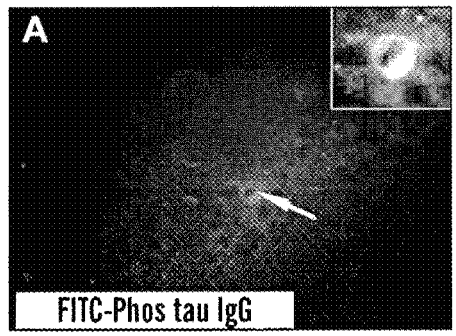
FIGS. 11A-F show neurons that label with the injected FITC-tagged antibody from an immunized mouse stain with MC1 and PHF1 antibodies.
Figure 11D:
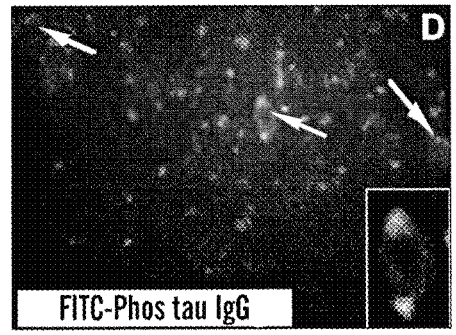
Figure 11B:
Figure 11E:
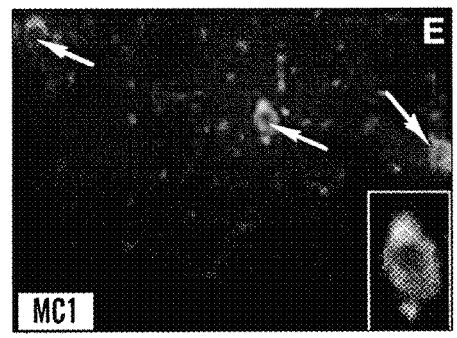
Figure 11C:
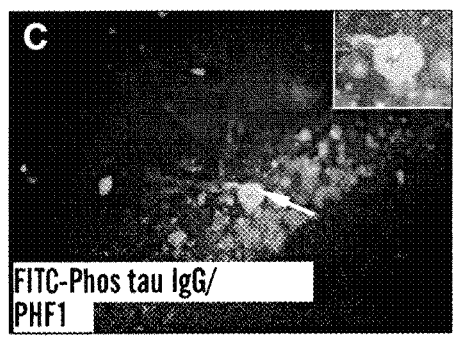
Figure 11F:
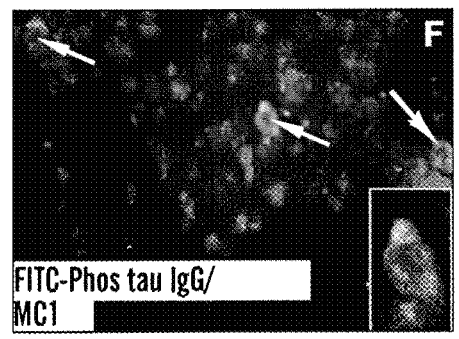

To confirm that anti-tau antibodies would gain access into the brain, purified IgG antibodies from an immunized mouse that had generated very high levels of antibodies against the immunogen were FITC-tagged. The FITC-labeled IgG was subsequently injected into the carotid artery of 8 month old P301L mice and their brains were harvested one hour later for analysis of antibody uptake. Several neurons in various brain regions showed typical green FITC fluorescence (FIG. 10), and, when the sections were incubated with PHF1 or MC1, these antibodies colocalized with the FITC-labeled IgG (FIG. 11). Carotid injection in another set of 8 month old P301L mice of FITC-labeled purified IgG from a control mouse that received only the alum adjuvant, resulted in some FITC fluorescence within the brain although it did not appear to be neuronal and it did not colocalize with PHF1 or MC1 staining. The identical approach in wild-type mice with the same antibodies did not lead to FITC fluorescence within the brain, indicating that leakage of the blood brain barrier (BBB) in the P301L model may at least in part explain treatment efficacy.

These results demonstrate that: 1) vaccination of P301L mice with a phospho-tau epitope leads to the generation of antibodies that enter the brain; 2) these antibodies bind to abnormal tau like a monoclonal antibody (PHF1) against a similar epitope; 3) this type of immunotherapy reduces the extent of aggregated tau in the brain and slows the progression of the behavioral phenotype of these animals; and 4) as expected, the therapeutic effect decreases as the functional impairments advance in these animals.

Regarding the mechanism of tau-based immunotherapy, it is well established that about 0.1% of circulating IgG is found within the CNS (Nerenberg, et al., "Radioimmunoassays for Ig Classes G, A, M, D, and E in Spinal Fluids: Normal Values of Different Age Groups," *J Lab Clin Med.* 86:887-898 (1975), which is hereby incorporated by reference in its entirety), and it may enter through regions that are deficient in BBB (Broadwell, et al., "Serum Proteins Bypass the Blood-Brain Fluid Barriers for Extracellular Entry to the Central Nervous System," *Exp Neurol.* 120: 245-263 (1993), which is hereby incorporated by reference in its entirety), as has been shown for an antibody targeting Aβ (Banks, et al., "Passage of Amyloid Beta Protein Antibody across the Blood-Brain Barrier in a Mouse Model of Alzheimer's Disease," *Peptides* 23:2223-2226 (2002), which is hereby incorporated by reference in its entirety). Also, IgG can cross the BBB via adsorptive-mediated transcytosis (Zlokovic, et al., "A Saturable Mechanism for Transport of Immunoglobulin G Across the Blood-Brain Barrier of the Guinea Pig," *Exp Neurol.* 107:263-270 (1990), which is hereby incorporated by reference in its entirety). The BBB is thought to be compromised in various neurological disorders such as AD, suggesting that a substantially greater percentage of circulating IgG can be found within the CNS. Increased permeability of the BBB has been observed in plaque depositing AD model mice (Poduslo, et al., "Permeability of Proteins at the Blood-Brain Barrier in the Normal Adult Mouse and Double Transgenic Mouse Model of Alzheimer's Disease," *Neurobiol Dis.* 8:555-567 (2001); LaRue, et al., "Method for Measurement of the Blood-Brain Barrier Permeability in the Perfused Mouse Brain: Application to Amyloid-beta Peptide in Wild type and Alzheimer's Tg2576 Mice," *Journal of Neuroscience Methods* 138:233-242 (2004), which are hereby incorporated by reference in their entirety), but has not been assessed in tangle AD model mice. However, the present observations indicate that the BBB is likely to be impaired in the P301L model. Besides antibody uptake into the brain, it is also well established that antibody secreting cells from the periphery can enter the brain and secrete the antibodies locally (Knopf, et al., "Antigen-Dependent Intrathecal Antibody Synthesis in the Normal Rat Brain: Tissue Entry and Local Retention of Antigen-Specific B Cells," *Journal of Immunology* 161:692-701 (1998), which is hereby incorporated by reference in its entirety). In the mouse immunotherapy studies, targeting Aβ, IgG has been routinely found within the brain associated with extracellular Aβ deposits and phagocytic microglia (Schenk D., "Amyloid-beta Immunotherapy for Alzheimer's Disease: The End of the Beginning," *Nat Rev Neurosci.* 3:824-828 (2002), which is hereby incorporated by reference in its entirety), and in the present study neuronal antibodies have been detected within the brain by immunohistochemistry. In addition, FITC-labeled IgG was detected in brains of P301L mice but not in wild-type mice following intracarotid injection which indicates that antibodies can enter the brain from the periphery in the P301L model. It is interesting to note that the levels of autoantibodies against tau increased with age, suggesting that age-related impairments of the BBB associated with the progression of brain pathology in these animals may expose the tau proteins as an antigen to the immune system.

Transport of antibodies within the CNS has not been thoroughly investigated, but IgG transport within and across cells in the periphery is essential for effective humoral immunity. Also, several studies have shown that antibodies can be found within neurons, which supports the feasibility of the present approach (for example, see Fabian, et al., "Intraneuronal IgG in the Central Nervous System," *J Neurol Sci.* 73:257-267 (1986); Fabian, et al., "Intraneuronal IgG in the Central Nervous System: Uptake by Retrograde Axonal Transport," *Neurology* 37:1780-1784 (1987); Liu, et al., "Immunohistochemical Localization of Intracellular Plasma Proteins in the Human Central Nervous System," *Acta Neuropathol (Berl).* 78:16-21 (1989); Dietzschold, et al., "Delineation of Putative Mechanisms Involved in Antibody-Mediated Clearance of Rabies Virus from the Central Nervous System," *Proc Natl Acad Sci USA* 89:7252-7256 (1992) (published erratum appears in *Proc Natl Acad Sci USA* 89(19):9365 (1992)); Aihara, et al., "Immunocytochemical Localization of Immunoglobulins in the Rat Brain: Relationship to the Blood-Brain Barrier," *J Comp Neurol.* 342:481-496 (1994); Mohamed, et al., "Immunoglobulin Fc Gamma Receptor Promotes Immunoglobulin Uptake, Immunoglobulin-Mediated Calcium Increase, and Neurotransmitter Release in Motor Neurons," *J Neurosci Res.* 69:110-116 (2002), which are hereby incorporated by reference in their entirety). The antibodies may enter the cells via pinocytosis, e.g. receptor-mediated endocytosis or fluid-phase endocytosis (Lobo, et al., "Antibody Pharmacokinetics and Pharmacodynamics," *J Pharm Sci.* 93:2645-2668 (2004), which is hereby incorporated by reference in its entirety). In cells that do not have surface antigens recognized by the antibody, receptor-mediated uptake may occur via Fcγ or FcRn receptors (Lobo, et al., "Antibody Pharmacokinetics and Pharmacodynamics," *J Pharm Sci.* 93:2645-2668 (2004), which is hereby incorporated by reference in its entirety), and Fcγ receptors have been located on neurons (Mohamed, et al., "Immunoglobulin Fc Gamma Receptor Promotes Immunoglobulin Uptake, Immunoglobulin-Mediated Calcium Increase, and Neurotransmitter Release in Motor Neurons," *J Neurosci Res.* 69:110-116 (2002); Andoh, et al., "Direct Action of Immunoglobulin G on Primary Sensory Neurons Through Fc Gamma Receptor I," *FASEB J.* 18:182-184 (2004), which are hereby incorporated in their entirety by reference). Indeed, it has been demonstrated that central neurons that project to the periphery, such as motor neurons, take up IgG at their synapses by retrograde axonal transport through receptors for the Fc portion of IgG (Fabian, et al., "Intraneuronal IgG in the Central Nervous System: Uptake by Retrograde Axonal Transport," *Neurology* 37:1780-1784 (1987); Mohamed, et al., "Immunoglobulin Fc Gamma Receptor Promotes Immunoglobulin Uptake, Immunoglobulin-Mediated Calcium Increase, and Neurotransmitter Release in Motor Neurons," *J Neurosci Res.* 69:110-116 (2002), which are hereby incorporated by reference in their entirety). One strong possibility is that circulating anti-tau antibodies in the CNS may recognize and cross-link abnormally conformed neuronal plasma membrane associated tau. As a matter of fact, tau has been shown to be associated with neural plasma membrane components in addition to microtubules, and there is evidence that this interaction is influenced by phosphorylation of tau at sites that are modified in paired helical filaments (PHFs) (Ditella, et al., "Microfilament-Associated Growth Cone Component Depends Upon Tau for Its Intracellular-Localization," *Cell Motility and the Cytoskeleton* 29:117-130 (1994); Brandt, et al., "Interaction of Tau with the Neural Plasma-Membrane Mediated by Tau Amino-Terminal Projection Domain," *J. Cell Biol.* 131: 1327-1340 (1995); Ekinci, et al., "Phosphorylation of Tau Alters its Association with the Plasma Membrane," *Cellular and Molecular Neurobiology* 20:497-508 (2000); Maas, et al., "Interaction of Tau with the Neural Membrane Cortex is Regulated by Phosphorylation at Sites that are Modified in Paired Helical Filaments," *J Biol Chem.* 275:15733-15740 (2000), which are hereby incorporated by reference in their entirety). In addition, tau interacts with actin (Correas, et al., "The Tubulin-Binding Sequence of Brain Microtubule-Associated Proteins, Tau and Map-2, is also Involved in Actin Binding," *Biochemical Journal* 269:61-64 (1990), which is hereby incorporated by reference in its entirety)) and spectrin (Carlier, et al., "Interaction Between Microtubule-Associated Protein Tau and Spectrin," *Biochimie* 66: 305-311 (1984), which is hereby incorporated by reference in its entirety), which may provide another link to the neural membrane.

Clearance of extracellular tangles may reduce associated pathology, and, because of the numerous reports of cellular uptake of antibodies some of which are cited above, intracellular tangles and pre-tangles may also be cleared, which could prevent neuronal damage. Recent findings from a related field support the validity of the present approach and subsequent observations. Like tau in AD, α-synuclein aggregates intracellularly within the brain in Parkinson's disease, and immunization with α-synuclein in mice with this pathology clears these aggregates (Masliah, et al., "Effects of Alpha-Synuclein Immunization in a Mouse Model of Parkinson's Disease," *Neuron* 46:857-868 (2005), which is hereby incorporated by reference in its entirety).

Less effort has been spent on developing therapy targeting pathological tau conformers than their Aβ counterparts. With regard to immunotherapy, Aβ plaque clearance in the AN 1792 trial did not appear to affect tangle pathology (Nicoll, et al., "Neuropathology of Human Alzheimer Disease after Immunization with Amyloid-beta Peptide: A Case Report," *Nat Med.* 9:448-452 (2003); Ferrer, et al., "Neuropathology and Pathogenesis of Encephalitis Following Amyloid-beta Immunization in Alzheimer's Disease," *Brain Pathol.* 14:11-20 (2004); Masliah, et al., "Abeta Vaccination Effects on Plaque Pathology in the Absence of Encephalitis in Alzheimer Disease," *Neurology* 64:129-131 (2005), which are hereby incorporated by reference in their entirety). However, Aβ immunotherapy in a mouse model cleared early tau pathology but not hyperphosphorylated tau aggregates (Oddo, et al., "Abeta Immunotherapy Leads to Clearance of Early, but not Late, Hyperphosphorylated Tau Aggregates via the Proteasome," *Neuron* 43:321-332 (2004), which is hereby incorporated by reference in its entirety). These findings emphasize the need for therapy targeting pathological tau conformers. In Aβ plaque mouse models, it may not be necessary to clear plaques to observe a cognitive benefit (Sigurdsson E., "Immunotherapy for Conformational Diseases," *Current Pharmaceutical Design* 12:2569-2585 (2006), which is hereby incorporated by reference in its entirety). This concept may also apply to tau pathology, because suppression of transgenic tau in a tangle mouse model has been shown to improve memory although neurofibrillary tangles remained (Santacruz, et al., "Tau Suppression in a Neurodegenerative Mouse Model Improves Memory Function," *Science* 309:476-481 (2005), which is hereby incorporated by reference in its entirety). In that same model, region-specific dissociation of neuronal loss and neurofibrillary pathology has been observed (Spires, et al., "Region-Specific Dissociation of Neuronal Loss and Neurofibrillary Pathology in a Mouse Model of Tauopathy," *Am J Patrol.* 168:1598-1607 (2006), which is hereby incorporated by reference in its entirety) which suggests toxic effects of early stage pathological tau conformers that cannot easily be detected, analogous to Aβ oligomers. A similar lack of correlation of tau pathology with neuronal death was previously reported in another tangle model, hTau, that overexpresses unmutated human tau on a mouse tau knockout background (Andorfer, et al., "Cell-Cycle Reentry and Cell Death in Transgenic Mice Expressing Nonmutant Human Tau Isoforms," *J Neurosci.* 25: 5446-5454 (2005), which is hereby incorporated by reference in its entirety). Considering these discrepancies, it is interesting that although the model employed here has age-related progression in tau pathology and functional impairments, immunohistochemical analysis revealed a similar degree of tau pathology at 5 and 8 months and the animals performed at a comparable level on the Rotarod and the Traverse Beam at these different ages. However, their locomotor activity was substantially less at 8 months compared to 5 months. It is also of note that a significant correlation was observed between performance on the Rotarod and the Traverse Beam and tau pathology in two out of the three brain areas analyzed, namely the motor cortex and the brain stem (see Table 3) both of which have a prominent role in motor coordination, which indicates a direct relationship between the main pathological feature of this model and associated functional impairments.

The immunotherapy approach used here was substantially more effective in the early stages of functional impairments in the animals (at 5 months) than at a later time point (at 8 months). These findings indicate that clearance of early stage pathological tau conformers may be of a therapeutic benefit. These smaller aggregates should also be easier to clear than late stage neurofibrillary tangles. As previously reported in the original heterozygous line of this model (Lewis, et al., "Neurofibrillary Tangles, Amyotrophy and Progressive Motor Disturbance in Mice Expressing Mutant (P301L) Tau Protein," *Nat Genet.* 25:402-405 (2000), which is hereby incorporated by reference in its entirety), the homozygous females had more extensive neurofibrillary pathology than the males as observed by immunohistochemistry (see Table 2). It was, therefore, surprising that the immunotherapy was more effective in the females. Similar gender differences in therapeutic outcome in other transgenic models of tau pathology have not been reported. A possible explanation is that more of the aggregated tau in the females is available for antibody-mediated disassembly because of its higher levels within the neurons. In the male animals, the lower amount of pathological tau may be more easily sequestered and thereby less accessible for antibody binding. A related possibility is that because of its higher levels and presumably more rapid assembly, the tau aggregates in the females may be more soluble and hence more easily removed. The Western blot data did not correlate exactly with the immunohistochemical findings. However, similar gender differences were detected and a more robust treatment effect was observed with both types of analysis in the 5 month old group compared to the 8 month old animals. Any discrepancy may at least in part be related to the artificial antibody epitopes that are generated in the blots. It is well established that both the MC1- and PHF1 antibodies show greater specificity towards pathological tau on histological sections than in Western blots (Greenberg, et al., "Hydrofluoric Acid-Treated Tau PHF Proteins Display the Same Biochemical Properties as Normal Tau," *J Biol Chem.* 267:564-569 (1992); Rye, et al., "The Distribution of Alz-50 Immunoreactivity in the Normal Human Brain," *Neuroscience* 56:109-127 (1993); Jicha, et al., "Alz-50 and MC-1, a New Monoclonal Antibody Raised to Paired Helical Filaments, Recognize Conformational Epitopes on Recombinant Tau," *Journal of Neuroscience Research* 48:128-132 (1997); Weaver, et al., "Conformational Change as one of the Earliest Alterations of Tau in Alzheimer's Disease," *Neurobiol Aging* 21:719-727 (2000), which are hereby incorporated by reference in their entirety).

It should be emphasized that these tau immunotherapy studies were performed in transgenic mice that are homozygous for the tau mutation P301L. These animals have a very aggressive phenotype with tau pathology detected within a few months of age and with related severe functional impairments observed a few months later. The present approach should be more effective in transgenic animals with a phenotype progression that more resembles the human condition, and eventually in humans with frontotemporal dementia and/or AD in which pathology develops over years or decades instead of months.

Overall, the present findings support the feasibility of immunotherapy targeting pathological tau conformers that may benefit AD patients and individuals with frontotemporal dementia caused by tau mutations.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

The invention claimed is:

1. A pharmaceutical composition comprising:
   (A) a recombinantly-produced antibody or a binding portion thereof that is capable of specifically binding to a misfolded and/or aggregate form of Tau protein and does not equivalently bind to normal Tau protein, wherein said recombinantly-produced antibody comprises the amino acid sequence of a binding portion of an antibody elicited by immunization with a polypeptide fragment of Tau protein consisting of Tau 379-408 that possesses phosphoserine residues at Tau position 396 and at Tau position 404 (SEQ ID NO:2); and
   (B) a pharmaceutically acceptable carrier or diluent.

2. The pharmaceutical composition of claim 1, wherein said recombinantly-produced antibody or said binding portion thereof binds to one or more phosphorylated residues of said misfolded and/or aggregate form of Tau protein.

3. The pharmaceutical composition of claim 1, wherein said recombinantly-produced antibody is a chimeric or humanized antibody.

4. The pharmaceutical composition of claim 1, wherein said composition contains an amount of said antibody or binding portion thereof effective to promote the clearance of Tau aggregates from the brain of a recipient subject.

5. The pharmaceutical composition of claim 4, wherein said recipient subject exhibits a symptom of Alzheimer's disease or other tauopathy.

6. The pharmaceutical composition of claim 1, wherein said composition contains an amount of said recombinantly-produced antibody or binding portion thereof effective for the treatment of Alzheimer's disease or other tauopathy of a recipient subject.

7. The pharmaceutical composition of claim 6, wherein said recipient subject exhibits a symptom of Alzheimer's disease or said other tauopathy.

8. The pharmaceutical composition of claim 1, wherein said composition additionally comprises a second antibody or binding portion thereof.

9. The pharmaceutical composition of claim 8, wherein said second antibody or binding portion thereof binds to one or more additional epitopes of said misfolded and/or aggregate form of Tau protein.

10. The pharmaceutical composition of claim 8, wherein said second antibody or binding portion thereof binds to one or more epitopes of amyloid-beta (Aβ).

11. The pharmaceutical composition of claim 10, wherein said composition contains an amount of said second antibody or binding portion thereof effective for the treatment of an amyloidogenic disease of a recipient subject.

12. The pharmaceutical composition of claim 8, wherein said second antibody or binding portion thereof binds to one or more epitopes of α-synuclein.

13. The pharmaceutical composition of claim 12, wherein said composition contains an amount of said second antibody or binding portion thereof effective for the treatment of a neurodegenerative disease of a recipient subject.

14. The pharmaceutical composition of claim 13, wherein said neurodegenerative disease is Parkinson's Disease.

15. The pharmaceutical composition of claim 1, wherein said recombinantly-produced antibody or binding portion thereof is a bispecific Fab fragment portion, one arm of which has said specificity for binding to said Tau epitope, and a second arm of which has specificity for binding to an Fc receptor.

* * * * *

UNITED STATES PATENT AND TRADEMARK OFFICE
CERTIFICATE OF CORRECTION

PATENT NO. : 9,777,056 B2
APPLICATION NO. : 14/833679
DATED : October 3, 2017
INVENTOR(S) : Einar M. Sigurdsson and Ayodeji Asuni Page 1 of 1

It is certified that error appears in the above-identified patent and that said Letters Patent is hereby corrected as shown below:

In the Specification

Column 1, Line 22:
Please delete "The subject matter of this application was made with support from the United States Government under NIH/NIA, Grant No. AG20197. The U.S. Government may have certain rights."

And insert --This invention was made with government support under AG020197 awarded by the National Institutes of Health. The government has certain rights in the invention.--.

Signed and Sealed this
Twenty-second Day of April, 2025

Coke Morgan Stewart
*Acting Director of the United States Patent and Trademark Office*